US012128228B2

(12) United States Patent
Friedland et al.

(10) Patent No.: US 12,128,228 B2
(45) Date of Patent: Oct. 29, 2024

(54) BLOOD PUMPS

(71) Applicant: MAGENTA MEDICAL LTD, Kadima (IL)

(72) Inventors: Ori Friedland, Tel Aviv (IL); Yuval Zipory, Modi'in Makkabbim-Re'ut (IL); Yuri Sudin, Modi'in Makkabbim-Re'ut (IL); Ayelet Haimy, Kochav Yair (IL); Ehud Schwammenthal, Raanana (IL); Yosi Tuval, Even Yehuda (IL); Tak Gee Cheung, San Mateo, CA (US)

(73) Assignee: MAGENTA MEDICAL LTD, Kadima (IL)

( * ) Notice: Subject to any disclaimer, the term of this patent is extended or adjusted under 35 U.S.C. 154(b) by 467 days.

(21) Appl. No.: 17/608,312

(22) PCT Filed: May 20, 2020

(86) PCT No.: PCT/IB2020/054759
§ 371 (c)(1),
(2) Date: Nov. 2, 2021

(87) PCT Pub. No.: WO2020/234785
PCT Pub. Date: Nov. 26, 2020

(65) Prior Publication Data
US 2022/0218976 A1 Jul. 14, 2022

Related U.S. Application Data

(60) Provisional application No. 62/851,769, filed on May 23, 2019, provisional application No. 62/870,822, (Continued)

(51) Int. Cl.
*A61M 60/13* (2021.01)
*A61B 17/12* (2006.01)
(Continued)

(52) U.S. Cl.
CPC ..... *A61M 60/531* (2021.01); *A61B 17/12181* (2013.01); *A61M 60/13* (2021.01);
(Continued)

(58) Field of Classification Search
CPC .............. A61M 60/531; A61M 60/833; A61M 60/867; A61M 60/546; A61M 60/13; A61M 60/178; A61M 60/216; A61B 17/12181
(Continued)

(56) References Cited

U.S. PATENT DOCUMENTS 4,822,345 A 4/1989 Danforth
4,886,506 A 12/1989 Lovgren et al.
(Continued)

FOREIGN PATENT DOCUMENTS

AU 2013205145 A1 5/2013
AU 2013257469 B2 3/2016
(Continued)

OTHER PUBLICATIONS

Advisory Action for U.S. Appl. No. 15/888,771 mailed May 4, 2022.
(Continued)

*Primary Examiner* — Erin M Piateski
(74) *Attorney, Agent, or Firm* — Dorsey & Whitney LLP

(57) ABSTRACT

Apparatus and methods are described for use with a venous system of a subject that includes one or more tributary vessels that flow into a vein at junctions. A blood-pump-catheter (70) includes a material (36) configured to be placed at a downstream location that is downstream of the junctions and to at least partially occlude blood flow through the vein. The material defines a blood-outlet opening (31). A blood pump (24) pumps blood from a region of the vein that is adjacent to the junctions, and through the blood-outlet
(Continued)

opening (31). A blood-flow pathway (60) directs upstream venous blood flow from an upstream location that is upstream of the junctions, to downstream of the material (36), without the upstream venous blood flow being pumped by the pump (24). Other applications are also described.

20 Claims, 29 Drawing Sheets

Related U.S. Application Data filed on Jul. 5, 2019, provisional application No. 62/890,177, filed on Aug. 22, 2019, provisional application No. 62/983,786, filed on Mar. 2, 2020.

(51) Int. Cl.
*A61M 60/178* (2021.01)
*A61M 60/216* (2021.01)
*A61M 60/531* (2021.01)
*A61M 60/546* (2021.01)
*A61M 60/833* (2021.01)
*A61M 60/857* (2021.01)
*A61M 60/867* (2021.01)

(52) U.S. Cl.
CPC ........ *A61M 60/178* (2021.01); *A61M 60/216* (2021.01); *A61M 60/546* (2021.01); *A61M 60/833* (2021.01); *A61M 60/867* (2021.01)

(58) Field of Classification Search
USPC .......................................................... 600/16
See application file for complete search history.

(56) References Cited

U.S. PATENT DOCUMENTS

| | | |
|---|---|---|
| 4,919,647 A | 4/1990 | Nash |
| 4,954,055 A | 9/1990 | Raible et al. |
| 5,040,944 A | 8/1991 | Cook |
| 5,300,112 A | 4/1994 | Barr |
| 5,613,935 A | 3/1997 | Jarvik |
| 5,713,730 A | 2/1998 | Nose et al. |
| 5,749,855 A | 5/1998 | Reitan |
| 5,772,693 A | 6/1998 | Brownlee |
| 5,876,385 A | 3/1999 | Ikari et al. |
| 5,964,694 A | 10/1999 | Siess et al. |
| 6,086,527 A | 7/2000 | Talpade |
| 6,135,729 A | 10/2000 | Aber |
| 6,136,025 A | 10/2000 | Barbut et al. |
| 6,176,848 B1 | 1/2001 | Rau et al. |
| 6,183,220 B1 | 2/2001 | Ohara et al. |
| 6,247,892 B1 | 6/2001 | Kazatchkov et al. |
| 6,482,228 B1 | 11/2002 | Norred |
| 6,533,716 B1 | 3/2003 | Schmutz-Rode et al. |
| 6,592,567 B1 | 7/2003 | Levin et al. |
| 6,616,624 B1 | 9/2003 | Kieval |
| 6,884,210 B2 | 4/2005 | Nose et al. |
| 7,004,925 B2 | 2/2006 | Navia et al. |
| 7,011,620 B1 | 3/2006 | Siess |
| 7,070,555 B2 | 7/2006 | Siess |
| 7,144,364 B2 | 12/2006 | Barbut et al. |
| 7,159,593 B2 | 1/2007 | Mccarthy et al. |
| 7,201,772 B2 | 4/2007 | Schwammenthal et al. |
| 7,335,192 B2 | 2/2008 | Keren et al. |
| 7,341,570 B2 | 3/2008 | Keren et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,503 B2 | 3/2011 | Goodson et al. |
| 7,927,068 B2 | 4/2011 | McBride et al. |
| 8,007,254 B2 | 8/2011 | Larose et al. |
| 8,012,121 B2 | 9/2011 | Goodson et al. |
| 8,079,948 B2 | 12/2011 | Shifflette |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,449,443 B2 | 5/2013 | Rodefeld et al. |
| 8,512,262 B2 | 8/2013 | Gertner |
| 8,538,535 B2 | 9/2013 | Ariav et al. |
| 8,579,858 B2 | 11/2013 | Reitan et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,849,398 B2 | 9/2014 | Evans |
| 8,992,163 B2 | 3/2015 | McBride et al. |
| 9,028,216 B2 | 5/2015 | Schumacher et al. |
| 9,067,006 B2 | 6/2015 | Toellner |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,217,442 B2 | 12/2015 | Wiessler et al. |
| 9,314,558 B2 | 4/2016 | Er |
| 9,327,067 B2 | 5/2016 | Zeng et al. |
| 9,339,596 B2 | 5/2016 | Roehn |
| 9,358,329 B2 | 6/2016 | Fitzgerald et al. |
| 9,393,384 B1 | 7/2016 | Kapur et al. |
| 9,402,942 B2 | 8/2016 | Hastie et al. |
| 9,416,783 B2 | 8/2016 | Schumacher et al. |
| 9,572,915 B2 | 2/2017 | Heuring et al. |
| 9,597,205 B2 | 3/2017 | Tuval |
| 9,675,740 B2 | 6/2017 | Zeng et al. |
| 9,750,860 B2 | 9/2017 | Schumacher |
| 9,750,861 B2 | 9/2017 | Hastie et al. |
| 9,764,113 B2 | 9/2017 | Tuval et al. |
| 9,771,801 B2 | 9/2017 | Schumacher et al. |
| 9,895,475 B2 | 2/2018 | Toellner et al. |
| 9,903,384 B2 | 2/2018 | Roehn |
| 9,907,891 B2 | 3/2018 | Wiessler et al. |
| 9,913,937 B2 | 3/2018 | Schwammenthal et al. |
| 9,964,115 B2 | 5/2018 | Scheckel |
| 10,039,874 B2 | 8/2018 | Schwammenthal et al. |
| 10,052,419 B2 | 8/2018 | Er |
| 10,107,299 B2 | 10/2018 | Scheckel |
| 10,172,985 B2 | 1/2019 | Simon et al. |
| 10,179,197 B2 | 1/2019 | Kaiser et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | McBride et al. |
| 10,231,838 B2 | 3/2019 | Chin et al. |
| 10,245,363 B1 | 4/2019 | Rowe |
| 10,299,701 B2 | 5/2019 | Blanton et al. |
| 10,299,918 B2 | 5/2019 | Tuval |
| 10,342,904 B2 | 7/2019 | Schumacher |
| 10,342,906 B2 | 7/2019 | D'Ambrosio et al. |
| 10,363,350 B2 | 7/2019 | Schwammenthal et al. |
| 10,413,646 B2 | 9/2019 | Wiessler et al. |
| 10,478,538 B2 | 11/2019 | Scheckel et al. |
| 10,478,539 B2 | 11/2019 | Pfeffer et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |
| 10,765,789 B2 | 9/2020 | Zeng et al. |

(56) References Cited

U.S. PATENT DOCUMENTS

| | | |
|---|---|---|
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,857,272 B2 | 12/2020 | Liebing |
| 10,864,309 B2 | 12/2020 | McBride et al. |
| 10,864,310 B2 | 12/2020 | Schwammenthal et al. |
| 10,865,801 B2 | 12/2020 | McBride et al. |
| 10,874,783 B2 | 12/2020 | Pfeffer et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,905,808 B2 | 2/2021 | Tuval et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,727 B2 | 6/2021 | Tuval et al. |
| 11,033,729 B2 | 6/2021 | Scheckel et al. |
| 11,040,187 B2 | 6/2021 | Wiessler et al. |
| RE48,649 E | 7/2021 | Siess |
| 11,116,960 B2 | 9/2021 | Simon et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,168,705 B2 | 11/2021 | Liebing |
| 11,197,690 B2 | 12/2021 | Fantuzzi et al. |
| 11,219,755 B2 | 1/2022 | Siess et al. |
| 11,229,786 B2 | 1/2022 | Zeng et al. |
| 11,253,692 B2 | 2/2022 | Schumacher |
| 11,253,693 B2 | 2/2022 | Pfeffer et al. |
| 11,260,215 B2 | 3/2022 | Scheckel et al. |
| 11,266,824 B2 | 3/2022 | Er |
| 11,268,521 B2 | 3/2022 | Toellner |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,291,824 B2 | 4/2022 | Schwammenthal et al. |
| 11,298,525 B2 | 4/2022 | Jahangir |
| 11,305,105 B2 | 4/2022 | Corbett et al. |
| 11,313,228 B2 | 4/2022 | Schumacher et al. |
| 11,338,124 B2 | 5/2022 | Pfeffer et al. |
| 11,351,358 B2 | 6/2022 | Nix et al. |
| 11,364,373 B2 | 6/2022 | Corbett et al. |
| 11,421,701 B2 | 8/2022 | Schumacher et al. |
| 11,434,922 B2 | 9/2022 | Roehn |
| 11,484,701 B2 | 11/2022 | Schwammenthal et al. |
| 11,648,387 B2 | 5/2023 | Schwammenthal et al. |
| 11,648,391 B2 | 5/2023 | Schwammenthal et al. |
| 11,648,392 B2 | 5/2023 | Tuval et al. |
| 11,806,117 B2 | 11/2023 | Tuval et al. |
| 2002/0107536 A1 | 8/2002 | Hussein |
| 2003/0055486 A1 | 3/2003 | Adams et al. |
| 2003/0149473 A1 | 8/2003 | Chouinard et al. |
| 2003/0208097 A1 | 11/2003 | Aboul-Hosn et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0219028 A1 | 11/2004 | Demarais et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0055082 A1 | 3/2005 | Ben et al. |
| 2005/0079274 A1 | 4/2005 | Palasis et al. |
| 2005/0119682 A1 | 6/2005 | Nguyen et al. |
| 2005/0137680 A1 | 6/2005 | Ortiz et al. |
| 2006/0062672 A1 | 3/2006 | McBride et al. |
| 2006/0064059 A1 | 3/2006 | Gelfand et al. |
| 2006/0106449 A1 | 5/2006 | Ben |
| 2006/0135961 A1 | 6/2006 | Rosenman et al. |
| 2006/0245959 A1 | 11/2006 | Larose et al. |
| 2007/0100435 A1 | 5/2007 | Case et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0293808 A1 | 12/2007 | Williams et al. |
| 2008/0103591 A1 | 5/2008 | Siess |
| 2008/0114339 A1 | 5/2008 | McBride et al. |
| 2008/0132748 A1 | 6/2008 | Shifflette |
| 2008/0154236 A1 | 6/2008 | Elkins et al. |
| 2008/0183280 A1 | 7/2008 | Agnew et al. |
| 2009/0024195 A1 | 1/2009 | Rezai et al. |
| 2009/0062597 A1 | 3/2009 | Shifflette |
| 2009/0093796 A1 | 4/2009 | Pfeffer et al. |
| 2009/0131785 A1 | 5/2009 | Lee et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0030259 A1 | 2/2010 | Pavcnik et al. |
| 2010/0130810 A1 | 5/2010 | Mohl |
| 2011/0004046 A1 | 1/2011 | Campbell et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0282274 A1 | 11/2011 | Fulton |
| 2011/0301662 A1 | 12/2011 | Bar-yoseph et al. |
| 2011/0319906 A1 | 12/2011 | Rudakov et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0172654 A1 | 7/2012 | Bates |
| 2012/0224970 A1 | 9/2012 | Schumacher et al. |
| 2012/0232457 A1 | 9/2012 | Kandarpa |
| 2012/0237357 A1 | 9/2012 | Schumacher et al. |
| 2012/0301318 A1 | 11/2012 | Er |
| 2012/0328460 A1 | 12/2012 | Horvath et al. |
| 2013/0053623 A1 | 2/2013 | Evans et al. |
| 2013/0053732 A1 | 2/2013 | Heuser |
| 2013/0079874 A1 | 3/2013 | Doss et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2014/0018840 A1 | 1/2014 | Morgan et al. |
| 2014/0025041 A1 | 1/2014 | Fukuoka et al. |
| 2014/0051908 A1 | 2/2014 | Khanal et al. |
| 2014/0128659 A1 | 5/2014 | Heuring et al. |
| 2014/0275722 A1 | 9/2014 | Zimmermann et al. |
| 2014/0275726 A1 | 9/2014 | Zeng |
| 2014/0350658 A1 | 11/2014 | Benary et al. |
| 2015/0018597 A1 | 1/2015 | Fierens et al. |
| 2015/0119633 A1 | 4/2015 | Haselby et al. |
| 2015/0141739 A1 | 5/2015 | Hsu et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0343136 A1 | 12/2015 | Nitzan et al. |
| 2015/0343186 A1 | 12/2015 | Nitzan et al. |
| 2016/0022890 A1* | 1/2016 | Schwammenthal .......... A61M 60/422 600/16 |
| 2016/0051741 A1 | 2/2016 | Schwammenthal et al. |
| 2016/0053768 A1 | 2/2016 | Schumacher et al. |
| 2016/0136343 A1 | 5/2016 | Anagnostopoulos |
| 2016/0184500 A1 | 6/2016 | Zeng |
| 2016/0279310 A1 | 9/2016 | Scheckel et al. |
| 2017/0049946 A1 | 2/2017 | Kapur et al. |
| 2017/0071769 A1 | 3/2017 | Mangiardi |
| 2017/0100527 A1 | 4/2017 | Schwammenthal et al. |

(56) References Cited

U.S. PATENT DOCUMENTS

| | | | |
|---|---|---|---|
| 2017/0197021 | A1 | 7/2017 | Nitzan et al. |
| 2018/0126130 | A1 | 5/2018 | Nitzan et al. |
| 2018/0149165 | A1 | 5/2018 | Siess et al. |
| 2018/0169313 | A1 | 6/2018 | Schwammenthal et al. |
| 2018/0303993 | A1 | 10/2018 | Schwammenthal et al. |
| 2019/0046702 | A1 | 2/2019 | Siess et al. |
| 2019/0175340 | A1 | 6/2019 | Tuval |
| 2019/0175806 | A1 | 6/2019 | Tuval et al. |
| 2019/0209758 | A1 | 7/2019 | Tuval et al. |
| 2019/0239998 | A1 | 8/2019 | Tuval et al. |
| 2019/0269840 | A1 | 9/2019 | Tuval et al. |
| 2020/0069857 | A1 | 3/2020 | Schwammenthal et al. |
| 2020/0254162 | A1 | 8/2020 | Schwammenthal et al. |
| 2020/0288988 | A1 | 9/2020 | Goldvasser |
| 2021/0236797 | A1 | 8/2021 | D'Ambrosio et al. |
| 2021/0268261 | A1 | 9/2021 | Tuval et al. |
| 2023/0233837 | A1 | 7/2023 | Schwammenthal et al. |
| 2023/0233841 | A1 | 7/2023 | Tuval et al. |

FOREIGN PATENT DOCUMENTS

| | | | |
|---|---|---|---|
| CA | 2701809 | A1 | 4/2009 |
| CN | 1219136 | A | 6/1999 |
| DE | 1033690 | B | 7/1958 |
| DE | 10336902 | B3 | 8/2004 |
| EP | 1339443 | A1 | 9/2003 |
| EP | 1651290 | A1 | 5/2006 |
| EP | 1827531 | A1 | 9/2007 |
| EP | 1871441 | A2 | 1/2008 |
| EP | 2047872 | A1 | 4/2009 |
| EP | 2047873 | A1 | 4/2009 |
| EP | 2217300 | A1 | 8/2010 |
| EP | 2218469 | A1 | 8/2010 |
| EP | 2234658 | A2 | 10/2010 |
| EP | 2282070 | A1 | 2/2011 |
| EP | 2298374 | A1 | 3/2011 |
| EP | 2299119 | A1 | 3/2011 |
| EP | 2301598 | A1 | 3/2011 |
| EP | 2308524 | A1 | 4/2011 |
| EP | 2314331 | A1 | 4/2011 |
| EP | 2345440 | A1 | 7/2011 |
| EP | 2366412 | A2 | 9/2011 |
| EP | 2376788 | A1 | 10/2011 |
| EP | 2408489 | A1 | 1/2012 |
| EP | 2424587 | A1 | 3/2012 |
| EP | 2475415 | A1 | 7/2012 |
| EP | 2607712 | A1 | 6/2013 |
| EP | 2040639 | B1 | 2/2014 |
| EP | 2662099 | B1 | 9/2014 |
| EP | 2427230 | B1 | 12/2014 |
| EP | 2396050 | B1 | 1/2015 |
| EP | 2835141 | A1 | 2/2015 |
| EP | 2840954 | A1 | 3/2015 |
| EP | 2841122 | A1 | 3/2015 |
| EP | 2841124 | A1 | 3/2015 |
| EP | 2860849 | A1 | 4/2015 |
| EP | 2868331 | A2 | 5/2015 |
| EP | 2868332 | A1 | 5/2015 |
| EP | 2999496 | A2 | 3/2016 |
| EP | 3000492 | A1 | 3/2016 |
| EP | 3000493 | A1 | 3/2016 |
| EP | 3055922 | A1 | 8/2016 |
| EP | 3062730 | A1 | 9/2016 |
| EP | 3108909 | A1 | 12/2016 |
| EP | 3127562 | A1 | 2/2017 |
| EP | 3216467 | A1 | 9/2017 |
| EP | 3222302 | A1 | 9/2017 |
| EP | 3287154 | A1 | 2/2018 |
| EP | 3287155 | A1 | 2/2018 |
| EP | 3326567 | A1 | 5/2018 |
| EP | 3329951 | A1 | 6/2018 |
| EP | 3338825 | A1 | 6/2018 |
| EP | 3205360 | B1 | 8/2018 |
| EP | 3359214 | A1 | 8/2018 |
| EP | 3359215 | A1 | 8/2018 |
| EP | 3398624 | A1 | 11/2018 |
| EP | 3398625 | A1 | 11/2018 |
| EP | 3407930 | A1 | 12/2018 |
| EP | 3446729 | A1 | 2/2019 |
| EP | 3446730 | A1 | 2/2019 |
| EP | 3606575 | A1 | 2/2020 |
| EP | 3737436 | A1 | 11/2020 |
| EP | 3897814 | A1 | 10/2021 |
| JP | 2012505038 | A | 3/2012 |
| JP | 2016509950 | A | 4/2016 |
| WO | 90/13321 | | 11/1990 |
| WO | 1994/01148 | A1 | 1/1994 |
| WO | 9744071 | A1 | 11/1997 |
| WO | 9934847 | A2 | 7/1999 |
| WO | 2001083016 | A2 | 5/2000 |
| WO | 0107787 | A1 | 2/2001 |
| WO | 2002/070039 | A2 | 3/2001 |
| WO | 0183016 | A2 | 11/2001 |
| WO | 2002038085 | | 5/2002 |
| WO | 03/006096 | | 1/2003 |
| WO | 03103745 | A2 | 12/2003 |
| WO | 2004073796 | A2 | 9/2004 |
| WO | 2005020848 | A2 | 3/2005 |
| WO | 2007112033 | A2 | 10/2007 |
| WO | 2007127477 | A2 | 11/2007 |
| WO | 2008005747 | A2 | 1/2008 |
| WO | 2008055301 | A1 | 5/2008 |
| WO | 2009010963 | A2 | 1/2009 |
| WO | 2009091965 | A1 | 7/2009 |
| WO | 2009129481 | A1 | 10/2009 |
| WO | 2010133567 | A1 | 11/2010 |
| WO | 2010150208 | A2 | 12/2010 |
| WO | 2011035926 | A1 | 3/2011 |
| WO | 2011047884 | A1 | 4/2011 |
| WO | 2011076441 | A1 | 6/2011 |
| WO | 2012007141 | A1 | 1/2012 |
| WO | 2013032849 | A1 | 3/2013 |
| WO | 2013148697 | A1 | 10/2013 |
| WO | 2013183060 | A2 | 12/2013 |
| WO | 2014141284 | A2 | 9/2014 |
| WO | 2015063277 | A2 | 5/2015 |
| WO | 2015177793 | A2 | 11/2015 |
| WO | 2016185473 | A1 | 11/2016 |
| WO | 2017053361 | A1 | 3/2017 |
| WO | 2017081561 | A1 | 5/2017 |
| WO | 2018033920 | A1 | 2/2018 |
| WO | 2018061001 | A2 | 4/2018 |
| WO | 2018061002 | A2 | 4/2018 |
| WO | 2018078615 | A1 | 5/2018 |
| WO | 2018096531 | A1 | 5/2018 |
| WO | 2018158636 | A1 | 9/2018 |
| WO | 2018172848 | A2 | 9/2018 |
| WO | 2018220589 | A1 | 12/2018 |
| WO | 2019079342 | A1 | 4/2019 |
| WO | 2019125899 | A1 | 6/2019 |
| WO | 2019138350 | A2 | 7/2019 |
| WO | 2019158996 | A1 | 8/2019 |
| WO | 2021159147 | A1 | 8/2021 |

OTHER PUBLICATIONS

Communication Pursuant to Article 94(3) for European Patent Application No. 20179137.3 mailed Nov. 9, 2021.
Examination Report for Canadian Application No. 2,948, 121 mailed Dec. 15, 2021.
Examination Report for Indian Application No. 201917018650 mailed Dec. 9, 2021.
Final Office Action for U.S. Appl. No. 15/888,771 mailed Dec. 9, 2021.
Final Office Action for U.S. Appl. No. 16/859,100 mailed Jul. 13, 2022.
Issue Notification for U.S. Appl. No. 15/574,948 mailed Mar. 16, 2022.
Issue Notification for U.S. Appl. No. 16/682,016 mailed Mar. 23, 2022.
Issue Notification for U.S. Appl. No. 16/682,269 mailed Mar. 23, 2022.

(56) References Cited

OTHER PUBLICATIONS

Non-Final Office Action for U.S. Appl. No. 15/888,771 mailed May 25, 2022.
Non-Final Office Action for U.S. Appl. No. 16/677,893 mailed Jan. 11, 2022.
Non-Final Office Action for U.S. Appl. No. 16/677,893 mailed Jul. 1, 2022.
Non-Final Office Action for U.S. Appl. No. 16/682,269 mailed Sep. 20, 2021.
Non-Final Office Action for U.S. Appl. No. 16/859,100 mailed Apr. 29, 2022.
Notice of Allowance for U.S. Appl. No. 15/574,948 mailed Jan. 27, 2022.
Notice of Allowance for U.S. Appl. No. 15/888,771 mailed Jun. 28, 2022.
Notice of Allowance for U.S. Appl. No. 16/682,016 mailed Feb. 23, 2022.
Notice of Allowance for U.S. Appl. No. 16/682,269 mailed Feb. 23, 2022.
Office Action for Japanese Application No. 2019-520097 mailed Oct. 26, 2021.
Examination Report for Australian Application No. 2021225141 mailed Oct. 10, 2022.
Extended European Search Report for European Patent Application No. 23174906.0 mailed Aug. 21, 2023.
Issue Notification for U.S. Appl. No. 16/859,100 mailed Apr. 26, 2023.
Issue Notification for U.S. Appl. No. 16/859,492 mailed Apr. 26, 2023.
Issue Notification for U.S. Appl. No. 17/320,742 mailed Apr. 26, 2023.
Non-Final Office Action for U.S. Appl. No. 16/677,893 mailed May 9, 2023.
Non-Final Office Action for U.S. Appl. No. 17/487,145 mailed Mar. 1, 2023.
Notice of Acceptance for Australian Application No. 2017364359 mailed Nov. 17, 2022.
Notice of Allowance for U.S. Appl. No. 16/859,100 mailed Mar. 7, 2023.
Notice of Allowance for U.S. Appl. No. 16/859,492 mailed Mar. 15, 2023.
Notice of Allowance for U.S. Appl. No. 17/320,742 mailed Mar. 22, 2023.
Notice of Allowance for U.S. Appl. No. 17/487,145 mailed Aug. 15, 2023.
Office Action for Canadian Application No. 3,039,302 mailed Mar. 21, 2023.
Office Action for Canadian Application No. 3,080,800 mailed Mar. 21, 2023.
Office Action for Canadian Application No. 3,126,978 mailed May 1, 2023.
Office Action for Canadian Application No. 3,126,978 mailed Nov. 1, 2022.
Office Action for Canadian Application No. 3,137,274 mailed Mar. 29, 2023.
U.S. Appl. No. 15/312,034, filed Nov. 17, 2016.
U.S. Appl. No. 15/888,771, filed Feb. 5, 2018.
U.S. Appl. No. 18/130,205, filed Apr. 4, 2023.
U.S. Appl. No. 18/130,534, filed Apr. 4, 2023.
U.S. Appl. No. 18/130,698, filed Apr. 4, 2023.
U.S. Appl. No. 62/727,605, filed Sep. 6, 2018.
Corrected Notice of Allowance for U.S. Appl. No. 18/130,534 mailed Nov. 24, 2023.
Issue Notification for U.S. Appl. No. 16/677,893 mailed Jan. 10, 2024.
Issue Notification for U.S. Appl. No. 17/487,145 mailed Nov. 22, 2023.
Issue Notification for U.S. Appl. No. 18/130,534 mailed Dec. 6, 2023.
Non-Final Office Action for U.S. Appl. No. 18/130,205 mailed Dec. 20, 2023.
Non-Final Office Action for U.S. Appl. No. 18/130,698 mailed Dec. 15, 2023.
Notice of Allowance for U.S. Appl. No. 16/677,893 mailed Oct. 19, 2023.
Notice of Allowance for U.S. Appl. No. 18/130,534 mailed Oct. 30, 2023.
Office Action for Chinese Application No. 202080038424.0 mailed Dec. 18, 2023.
Supplemental Notice of Allowance for U.S. Appl. No. 17/487,145 mailed Nov. 3, 2023.
U.S. Appl. No. 18/388,383, filed Nov. 9, 2023.
U.S. Appl. No. 18/422,309, filed Jan. 25, 2024.
U.S. Appl. No. 18/510,983, filed Nov. 16, 2023.
Communication for European Application No. 15753493.4 mailed Jul. 17, 2019.
Corrected Notice of Allowance for U.S. Appl. No. 15/312,034 mailed Feb. 12, 2020.
Corrected Notice of Allowance for U.S. Appl. No. 15/423,368 mailed Apr. 17, 2019.
European Search Report for European Application No. 13800935 mailed Jan. 12, 2016.
European Search Report for European Application No. 14762232.8 mailed Sep. 28, 2016.
Extended European Search Report for European Application No. 19212211.7 mailed Mar. 31, 2020.
Extended European Search Report for European Application No. 19215724.6 mailed Apr. 1, 2020.
Extended European Search Report for European Application No. 19216488.7 mailed Apr. 1, 2020.
Extended European Search Report for European Application No. 19216593.4 mailed Apr. 6, 2020.
Extended European Search Report for European Application No. 20179137.3 mailed Oct. 9, 2020.
Final Office Action for U.S. Appl. No. 14/931,363 mailed Jun. 1, 2017.
Final Office Action for U.S. Appl. No. 15/312,034 mailed Jan. 17, 2019.
Final Office Action for U.S. Appl. No. 15/574,948 mailed Aug. 26, 2020.
Final Office Action for U.S. Appl. No. 15/888,771 mailed Apr. 28, 2020.
Final Office Action for U.S. Appl. No. 16/273,898 mailed Nov. 5, 2020.
Final Office Action for U.S. Appl. No. 16/278,323 mailed May 22, 2020.
International Search Report and Written Opinion from International Application No. PCT/IB2020/054759 mailed Nov. 13, 2020.
International Search Report and Written Opinion from International Application No. PCT/IL2015/050532 mailed Jan. 27, 2016.
International Search Report and Written Opinion from International Application No. PCT/IL2016/050525 mailed Oct. 14, 2016.
International Search Report and Written Opinion from International Application No. PCT/IL2017/051092 mailed Jan. 16, 2018.
International Search Report and Written Opinion from International Application No. PCT/IL2017/051273 mailed Apr. 17, 2018.
International Search Report and Written Opinion from International Application No. PCT/IL2019/050334 mailed Jun. 17, 2019.
International Search Report and Written Opinion from International Application No. PCT/IL2013/050495 mailed Nov. 22, 2013.
International Search Report and Written Opinion from International Application No. PCT/IL2014/050289 mailed Sep. 11, 2014.
Invitation to Pay Additional Fees for International Application No. PCT/IB2020/054759 mailed Jul. 30, 2020.
Invitation to pay additional fees for International Application No. PCT/IL2015/050532 dated Nov. 17, 2015.
Issue Notification for U.S. Appl. No. 14/931,363 mailed Feb. 21, 2018.
Issue Notification for U.S. Appl. No. 15/312,034 mailed Feb. 19, 2020.
Issue Notification for U.S. Appl. No. 15/423,368 mailed May 8, 2019.

(56) References Cited

OTHER PUBLICATIONS

Issue Notification for U.S. Appl. No. 16/022,445 mailed Jul. 10, 2019.
Issue Notification for U.S. Appl. No. 16/035,871 mailed Dec. 29, 2020.
Issue Notification for U.S. Appl. No. 16/273,898 mailed Oct. 13, 2021.
Issue Notification for U.S. Appl. No. 16/278,323 mailed Nov. 24, 2020.
Issue Notification for U.S. Appl. No. 16/281,385 mailed Jun. 16, 2021.
Issue Notification for U.S. Appl. No. 16/335,786 mailed Jun. 2, 2021.
Issue Notification for U.S. Appl. No. 16/345,389 mailed May 26, 2021.
Non-Final Office Action for U.S. Appl. No. 14/405,144 mailed Feb. 22, 2016.
Non-Final Office Action for U.S. Appl. No. 14/405,144 mailed Jul. 14, 2016.
Non-Final Office Action for U.S. Appl. No. 14/567,439 mailed Nov. 16, 2016.
Non-Final Office Action for U.S. Appl. No. 14/774,081 mailed May 24, 2017.
Non-Final Office Action for U.S. Appl. No. 14/774,081 mailed Oct. 12, 2017.
Non-Final Office Action for U.S. Appl. No. 14/931,363 mailed Feb. 15, 2017.
Non-Final Office Action for U.S. Appl. No. 14/931,363 mailed Oct. 3, 2016.
Non-Final Office Action for U.S. Appl. No. 15/423,368 mailed Jun. 6, 2018.
Non-Final Office Action for U.S. Appl. No. 15/574,948 mailed Jan. 13, 2020.
Non-Final Office Action for U.S. Appl. No. 15/888,771 mailed Jun. 1, 2021.
Non-Final Office Action for U.S. Appl. No. 15/888,771 mailed Oct. 4, 2019.
Non-Final Office Action for U.S. Appl. No. 16/022,445 mailed Aug. 9, 2018.
Non-Final Office Action for U.S. Appl. No. 16/035,871 mailed Jan. 22, 2020.
Non-Final Office Action for U.S. Appl. No. 16/22,445 mailed Aug. 9, 2018.
Non-Final Office Action for U.S. Appl. No. 16/273,898 mailed Feb. 17, 2021.
Non-Final Office Action for U.S. Appl. No. 16/273,898 mailed Jun. 18, 2020.
Non-Final Office Action for U.S. Appl. No. 16/278,323 mailed May 22, 2020.
Non-Final Office Action for U.S. Appl. No. 16/281,385 mailed Oct. 14, 2020.
Non-Final Office Action for U.S. Appl. No. 16/335,786 mailed Sep. 17, 2020.
Non-Final Office Action for U.S. Appl. No. 16/345,389 mailed Oct. 26, 2020.
Non-Final Office Action for U.S. Appl. No. 16/682,016 mailed Sep. 20, 2021.
Notice of Allowance for U.S. Appl. No. 14/567,439 mailed Jun. 2, 2017.
Notice of Allowance for U.S. Appl. No. 14/774,081 mailed Apr. 11, 2018.
Notice of Allowance for U.S. Appl. No. 14/931,363 mailed Dec. 12, 2017.
Notice of Allowance for U.S. Appl. No. 14/931,363 mailed Oct. 12, 2017.
Notice of Allowance for U.S. Appl. No. 15/312,034 mailed Jan. 15, 2020.
Notice of Allowance for U.S. Appl. No. 15/312,034 mailed Jun. 27, 2019.
Notice of Allowance for U.S. Appl. No. 15/423,368 mailed Apr. 4, 2019.
Notice of Allowance for U.S. Appl. No. 15/423,368 mailed Nov. 13, 2018.
Notice of Allowance for U.S. Appl. No. 16/022,445 mailed Mar. 18, 2019.
Notice of Allowance for U.S. Appl. No. 16/035,871 mailed Aug. 28, 2020.
Notice of Allowance for U.S. Appl. No. 16/035,871 mailed Dec. 4, 2020.
Notice of Allowance for U.S. Appl. No. 16/273,898 mailed Jun. 30, 2021.
Notice of Allowance for U.S. Appl. No. 16/278,323 mailed Oct. 29, 2020.
Notice of Allowance for U.S. Appl. No. 16/281,385 mailed Mar. 8, 2021.
Notice of Allowance for U.S. Appl. No. 16/335,786 mailed Feb. 22, 2021.
Notice of Allowance for U.S. Appl. No. 16/345,389 mailed Feb. 16, 2021.
Office Action for Australian Application No. 2015262870 mailed Apr. 29, 2019.
Office Action for Australian Application No. 2019202647 mailed Jun. 26, 2019.
Office Action for Australian Application No. 2020201055 mailed Sep. 15, 2020.
Office Action for Chinese Application No. 201380037335.4 mailed Mar. 22, 2017.
Office Action for Chinese Application No. 201380037335.4 mailed Oct. 17, 2016.
Office Action for Chinese Application No. 201380037335.4 mailed Sep. 20, 2017.
Office Action for Chinese Application No. 201810418034.0 mailed Aug. 4, 2020.
Office Action for Chinese Application No. 201810418034.0 mailed Dec. 24, 2020.
Office Action for Chinese Application No. 201810418034.0 mailed Nov. 1, 2019.
Office Action for Chinese Application No. 201811196500.1 mailed Aug. 28, 2020.
Office Action for Chinese Application No. 201910109564.1 mailed Feb. 1, 2021.
Office Action for European Application No. 13800935 mailed Sep. 30, 2016.
Office Action for Japanese Application No. 2015/562562 mailed Jan. 29, 2019.
Office Action for Japanese Application No. 2015-562562 mailed Jun. 13, 2018.
Office Action for Japanese Application No. 2015562562 mailed Oct. 27, 2017.
Office Action for Japanese Application No. 2016/568548 mailed Mar. 18, 2019.
Office Action for Japanese Application No. 2020-009045 mailed Feb. 1, 2021.
Restriction Requirement for U.S. Appl. No. 14/567,439 mailed Aug. 23, 2016.
Restriction Requirement for U.S. Appl. No. 14/774,081 mailed Mar. 9, 2017.
Restriction Requirement for U.S. Appl. No. 14/931,363 mailed Jul. 22, 2016.
Restriction Requirement for U.S. Appl. No. 15/888,771 mailed Apr. 15, 2019.
Restriction Requirement for U.S. Appl. No. 16/035,871, mailed Sep. 27, 2019.
Restriction Requirement for U.S. Appl. No. 16/677,893 mailed Sep. 22, 2021.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/423,368, filed Feb. 2, 2017.
U.S. Appl. No. 15/574,948, filed Nov. 17, 2017.
U.S. Appl. No. 16/022,445, filed Jun. 28, 2018.
U.S. Appl. No. 16/273,898, filed Feb. 12, 2019.

(56) References Cited

OTHER PUBLICATIONS

U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,323, filed Feb. 18, 2019.
U.S. Appl. No. 16/281,264, filed Feb. 21, 2019.
U.S. Appl. No. 16/281,385, filed Feb. 21, 2019.
U.S. Appl. No. 16/345,389, filed Apr. 26, 2019.
U.S. Appl. No. 16/677,893, filed Nov. 8, 2019.
U.S. Appl. No. 16/682,016, filed Nov. 13, 2019.
U.S. Appl. No. 16/750,354, filed Jan. 23, 2020.
U.S. Appl. No. 16/859,100, filed Apr. 27, 2020.
U.S. Appl. No. 16/859,492, filed Apr. 27, 2020.
U.S. Appl. No. 17/487,145, filed Sep. 28, 2021.
U.S. Appl. No. 61/656,244, filed Jun. 6, 2012.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,715, filed May 2, 2018.
U.S. Appl. No. 62/681,868, filed Jun. 7, 2018.
U.S. Appl. No. 62/727,605, filed Sep. 6, 2021.
U.S. Appl. No. 62/401,403 mailed Sep. 29, 2016.
Agarwal, et al., "Newer-generation ventricular assist devices.", Best Practice & Research Clinical Anesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure and Sodium Excretion During Renal Vein Constriction", American Physiological Society, 1980, pp. F279-F282.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, vol. 9, 2007, pp. 872-878.
Damman, et al., "Increased Central Venous Pressure Is Associated With Impaired Renal Function and Mortality in a Broad Spectrum of Patients With Cardiovascular Disease", Journal of American College of Cardiology, vol. 53, 2009, pp. 582-588.
Doty, et al., "The Effect of Increased Renal Venous Pressure on Renal Function", The Journal of Trauma,, vol. 47(6), Dec. 1999, pp. 1000-1003.
Felker, et al., "Anemia as a Risk Factor and Therapeutic Target in Heart Failure", Journal of the American College of Cardiology, vol. 44, 2004, pp. 959-966.
Firth, et al., "Raised Venous Pressure: A Direct Cause of Sodium Retention in Oedema?", The Lancet, May 7, 1988, pp. 1033-1036.
Forman, et al., "Incidence, Predictors at Admission, and Impact of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Gomes, et al., "Heterologous Valve Implantation in the Infra-Renal Vena Cava for Treatment of the Iliac Venous Valve Regurgitation Disease: Experimental Study", Rev Bras Cir Cardiovasc, vol. 17(4), 2002, pp. 367-369.

Haddy, et al., "Effect of Elevation of Intraluminal Pressure on Renal Vascular Resistance", Circulation Research Journal of the American Heart Association, vol. 4, 1956, pp. 659-663.
Heywood, et al., "High prevalence of renal dysfunction and its impact on outcome in 118,465 patients hospitalized with acute decompensated heart failure", a report from the ADHERE database. J Cardiac Fail, vol. 13, 2007, pp. 422-430.
Hillege, et al., "Renal Function as a Predictor of Outcome in a Broad Spectrum of Patients With Heart Failure", Circulation Journal of the American Heart Association, vol. 113, 2006, pp. 671-678.
Hillege, et al., "Renal Function, Neurohormonal Activation, and Survival in Patients With Chronic Heart Failure", Circulation Journal of the American Heart Association, vol. 102, 2000, pp. 203-210.
Hsu, et al., "Review of recent patents on foldable ventricular assist devices", Recent Patents on Biomedical Engineering, 5.3, 2012, pp. 208-222.
Ikari, "The Physics of Guiding Catheter; The IKARI Guiding Catheter in TRI", available at httu:i /www.docstoc.com/docs/148136553/The-[KARI-catheter---anovel-guide-for-TRI--, uploaded on Mar. 8, 2013.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation: First-in-Man Application of a Novel Approach to Tricuspid Regurgitation", European Heart Journal, (1-7 as printed), Feb. 15, 2011, pp. 1207-1213.
McAlister, et al., "Renal Insufficiency and Heart Failure: Prognostic and Therapeutic Implications From a Prospective Cohort Study", Circulation Journal of the American Heart Association, 109, 2004, pp. 1004-1009.
Mullens, et al., "Elevated Intra-Abdominal Pressure in Acute Decompensated Heart Failure. A Potential Contributor to Worsening Renal Function", Journal of the American College of Cardiology, vol. 51, 2008, pp. 300-306.
Mullens, et al., "Importance of Venous Congestion for Worsening of Renal Function in Advanced Decompensated Heart Failure", Journal of American College of Cardiology, vol. 53, 2009, pp. 589-596.
Mullens, et al., "Prompt Reduction in Intra-Abdominal Pressure Following Large-Volume Mechanical Fluid Removal Improves Renal Insufficiency In Refractory Decompensated Heart Failure", Journal of Cardiac Failure, vol. 14, 2008, pp. 508-514.
Notarius, et al., "Central Venous Pressure During Exercise: Role of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Reul, et al., "Blood pumps for circulatory support", Perfusion-Sevenoaks, 15.4, 2000, pp. 295-312.
Schmitz-Rode, et al., "An Expandable Percutaneous Catheter Pump for Left Ventricular Support", Journal of the American College of Cardiology, vol. 45, 2005, pp. 1856-1861.
Semple, et al., "Effect of Increased Renal Venous Pressure on Circulatory "Autoregulation" of Isolated Dog Kidneys", Circulation Research Journal of the American Heart Association, vol. 7, 1959, pp. 643-648.
Song, et al., "Axial flow blood pumps", ASAIO journal, 49, 2003, pp. 355-364.
Tang, et al., "Anemia in Chronic Heart Failure: Prevalence, Etiology, Clinical Correlates, and Treatment Options", Circulation Journal of the American Heart Association, vol. 113, 2006, pp. 2454-2461.
Throckmorton, et al., "Design of a protective cage for an intra vascular axial flow blood pump to mechanically assist the failing Fontan", Artificial organs, 33.8, 2009, pp. 611-621.

(56) References Cited

OTHER PUBLICATIONS

Thunberg, et al., "Ventricular assist devices today and tomorrow", Journal of cardiothoracic and vascular anesthesia, 24.4, 2010, pp. 656-680.

Timms, "A review of clinical ventricular assist devices", Medical engineering & physics, 33.9, 2011, pp. 1041-1047.

Uthoff, et al., "Central venous pressure at emergency room presentation predicts cardiac rehospitalization in patients with decompensated heart failure", European Journal of Heart Failure, 12, 2010, pp. 469-476.

Wencker, "Acute Cardio-Renal Syndrome: Progression From Congestive Heart Failure to Congestive Kidney Failure", Current Heart Failure Reports, vol. 4, 2007, pp. 134-138.

Winton, "The Control of Glomerular Pressure by Vascular Changes Within the Mammalian Kidney, Demonstrated by the Actions of Adrenaline", Journal of Physiology, vol. 73, Nov. 1931, pp. 151-162.

Winton, "The Influence of Venous Pressure on the Isolated Mammalian Kidney", Journal of Physiology, vol. 72(1), Jun. 6, 1931, pp. 49-61.

Wood, "The Mechanism of the Increased Venous Pressure With Exercise in Congestive Heart Failure", Journal of Clinical Investigation, vol. 41(11), 1962, pp. 2020-2024.

Wu, et al., "Design and simulation of axial flow maglev blood pump", International Journal of Information Engineering and Electronic Business, 3.2, 2011, p. 42.

Yancy, et al., "Clinical Presentation, Management, and in-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, vol. 47(1), 2006, pp. 76-84.

Examination Report for European Application No. 20179137.3 mailed Jan. 5, 2023.

Issue Notification for U.S. Appl. No. 15/888,771 mailed Oct. 12, 2022.

Non-Final Office Action for U.S. Appl. No. 16/677,893 mailed Dec. 28, 2022.

Non-Final Office Action for U.S. Appl. No. 16/859,492 mailed Oct. 14, 2022.

Non-Final Office Action for U.S. Appl. No. 17/320,742 mailed Dec. 7, 2022.

Office Action for Japanese Application No. 2022-31553 mailed Dec. 23, 2022.

Restriction Requirement for U.S. Appl. No. 16/859,492 mailed Jul. 28, 2022.

"Compendium of Technical and Scientific Information for the Hemopump Temporary Cardiac Assist System", Johnson & Johnson Interventional Systems, 1988, pp. 1-15.

Achour, et al., "Mechanical Left Ventricular Unloading Prior to Reperfusion Reduces Infarct Size in a Canine Infarction Model", Catheterization and Cardiovascular Interventions 64, 2005, pp. 182-192.

Butler, et al., "The Hemopump—A New Cardiac Prothesis Device", Reprinted from IEEE Transactions on Biomedical Engineering, vol. 37, No. 2, Feb. 1990, pp. 192-195.

Chan, et al., "Rapid manufacturing techniques in the development of an axial blood pump impeller", Proc. Instn Mech. Engrs vol. 217 Part H: J. Engineering in Medicine, 2003, pp. 469-475.

Dekker, et al., "Efficacy of a New Intraaortic Propeller Pump vs the Intraaortic Balloon Pump", Chest, vol. 123, Issue 6, Jun. 2003, pp. 2089-2095.

Flameng, "Temporary Cardiac Assist with an Axial Pump System", Steinkopff Verlag Darmstadt, 1991, 79 pages.

Frazier, et al., "First Human Use of the Hemopump, a Catheter-Mounted Ventricular Assist Device", Annual of Thoracic Surgeons, vol. 49, 1990, pp. 299-304.

Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.

Gunther, et al., "Experimentelle Radiologie", Life Sciences, Berichte Aus Der Rheinischwestfälischen Technischen Hochschule Aachen Ausgabe Feb. 2002, 9 pages.

Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.

Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.

Roundtree, et al., "The Hemopump Cardiac Assist System: Nursing Care of the Patient", Reprinted from Critical Care Nurse, Apr. 1991.

Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.

Siess, "System Analysis and Development of Intravascular Rotation Pumps for Cardiac Assist", Helmholtz-Institute—Chapter 3, Jun. 1998, 17 pages.

Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.

Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.

Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.

Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.

Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.

Wampler, "U.S. News & World Report", Captain Hemo, pp. 1-2, May 16, 1988.

Communication Pursuant to Article 94(3) EPC for European Patent Application No. 19216488.7 mailed Oct. 19, 2021.

Examination Report for Canadian Application No. 2,948,121 mailed Jul. 8, 2021.

Non-Final Office Action for U.S. Appl. No. 16/242,797 mailed Nov. 16, 2021.

Notice of Allowance for U.S. Appl. No. 15/574,948 mailed Nov. 18, 2021.

Office Action for Chinese Application No. 201780072633.5 mailed May 26, 2021.

Office Action for Japanese Application No. 2020-93277 mailed Jun. 23, 2021.

Examination Report for European Application No. 19716995.6 mailed Mar. 1, 2024.

Final Office Action for U.S. Appl. No. 18/130,205 mailed Jul. 16, 2024.

Non-Final Office Action for U.S. Appl. No. 18/510,983 mailed Jun. 5, 2024.

Notice of Allowance for U.S. Appl. No. 18/130,698 mailed Apr. 11, 2024.

Office Action for Canadian Application No. 3,137,274 mailed Jan. 15, 2024.

(56) References Cited

OTHER PUBLICATIONS

Office Action for Chinese Application No. 202110905794.6 mailed Feb. 1, 2024.
Office Action for Japanese Application No. 2021-563728 mailed Feb. 27, 2024.
Office Action for Japanese Application No. 2021-563728 mailed Jul. 10, 2024.
U.S. Appl. No. 17/320,742, filed May 14, 2021.

* cited by examiner

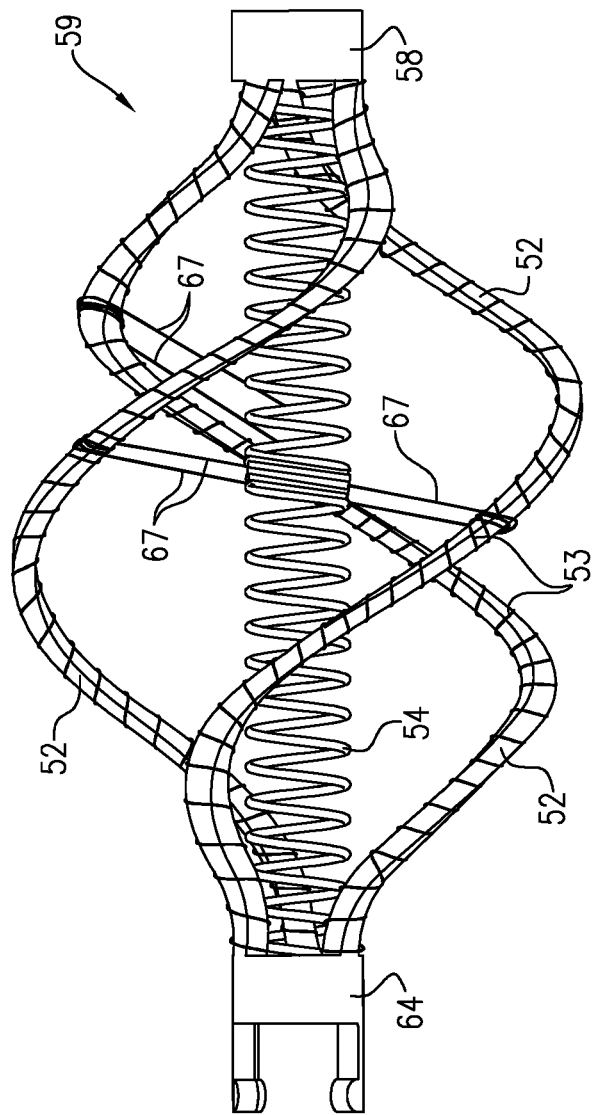

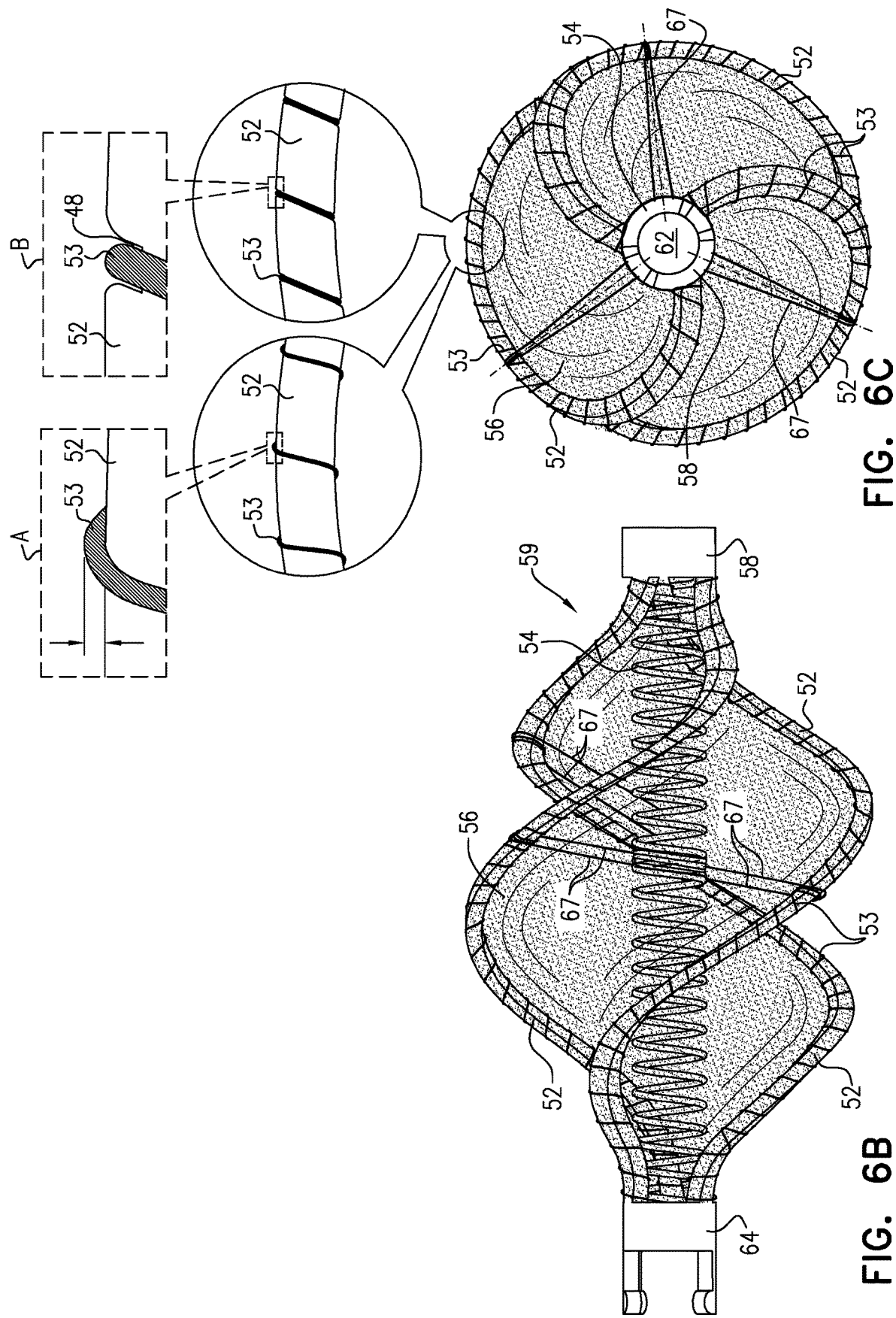

BLOOD PUMPS

CROSS-REFERENCES TO RELATED APPLICATIONS

The present application is a US national phase application of PCT Application No. PCT/IB2020/054759 to Friedland (published as WO 20/234785), filed May 20, 2020, which claims priority from:

U.S. Provisional Patent Application 62/851,769 to Friedland, entitled "Blood pumps," filed May 23, 2019;

U.S. Provisional Patent Application 62/870,822 to Friedland, entitled "Blood pumps," filed Jul. 5, 2019;

U.S. Provisional Patent Application 62/890,177 to Friedland, entitled "Blood pumps," filed Aug. 22, 2019; and U.S. Provisional Patent Application 62/983,786 to Friedland, entitled "Blood pumps," filed Mar. 2, 2020.

Each of the above-referenced applications is incorporated herein by reference.

FIELD OF EMBODIMENTS OF THE INVENTION

Some applications of the present invention generally relate to medical apparatus. Specifically, some applications of the present invention relate to apparatus and methods associated with placing a pump in a vein or an artery.

BACKGROUND

It is common for cardiac dysfunction or congestive heart failure to develop into kidney dysfunction, which, in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure may cause intracapsular pressure and, subsequently, interstitial peritubular pressure, to rise. A rise in peritubular pressure may impact tubular function (reduce sodium excretion), as well as diminish glomerular filtration, by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration), has been shown to reduce plasma creatinine levels.

Increased venous return resulting from activation of the "leg muscle pump" during physical activity such as walking may raise systemic venous pressure, particularly in heart failure patients, and may result in reflux into the renal veins.

Typically, in patients suffering from acute heart failure, elevated systemic venous pressures cause increased renal parenchymal pressure and increased intraabdominal pressure, factors that can contribute to deterioration of renal perfusion and function. In addition, high systemic venous pressures may impede lymphatic drainage of pulmonary interstitial fluid resulting in aggravation and prolongation of pulmonary congestion in patients with acute pulmonary edema.

SUMMARY OF EMBODIMENTS

In accordance with some applications of the present invention, the blood stream of a region of the vena cava that is adjacent to junctions of the vena cava with the renal veins is separated from the subject's vena-caval bloodstream upstream and downstream of the junctions. Blood is pumped from the region of the vena cava that is adjacent to the junctions to a suprarenal location within the vena cava, using a pump. The subject's blood is allowed to flow from an infrarenal location within the subject's vena cava to the suprarenal location, without being pumped by the pump, by directing the blood to bypass the pump.

For some applications, such methods include (a) at least partially occluding blood flow through a vein by placing a downstream occluding element (such as a material) at a downstream location that is downstream of junctions of the vein with one or more tributary vessels (e.g., one or more tributary veins), (b) pumping blood from a region of the vein that is adjacent to junctions of the vein with the tributary vessels through the downstream occluding element, using a pump, and (c) directing upstream venous blood flow from an upstream location that is upstream of junctions of the vein with the tributary vessels to downstream of the occluding element, without the upstream venous blood flow being pumped by the pump, by directing the upstream venous blood flow to bypass the pump.

Typically, such methods are performed using a blood-pump catheter, which includes a material that is configured to be placed at a downstream location that is downstream of junctions of the vein with the tributary vessel and to at least partially occlude blood flow through the vein at the downstream location. The material typically defines a blood-outlet opening. A blood pump is typically configured to pump blood from the region of the vein that is adjacent to junctions of the vein with the tributary vessels through the blood-outlet opening defined by the material. A blood-flow pathway (i.e., a blood-flow channel) typically passes between an inlet opening disposed at an upstream location that is upstream of junctions of the vein with the tributary vessel and an outlet opening that opens to a downstream side of the material. The blood-flow pathway is configured to direct upstream venous blood flow from the upstream location to downstream of the material, without the upstream venous blood flow being pumped by the pump. For some applications, the blood-flow pathway includes a funnel and one or more tubes. The funnel is configured to be disposed at an upstream location that is upstream of junctions of the vein with the tributary vessels, and the one or more tubes are configured to extend from the funnel to a downstream side of the material. The funnel and the one or more tubes are configured to direct upstream venous blood flow from the upstream location to downstream of the material, without the upstream venous blood flow being pumped by the pump.

In general, the scope of some applications of the present invention includes apparatus and methods for use with a venous system of a subject that includes tributary veins that flow into a main vein (e.g., renal veins that flow into the vena cava). Typically, such methods include separating bloodstream within the region of the main vein that is adjacent to junctions of the main vein with the tributary veins from bloodstream within the main vein upstream and downstream thereto, pumping blood from the region of the main vein that is adjacent to junctions of the vein with the tributary veins to a location within the main vein that is downstream of the tributary veins, using a pump, and allowing the subject's blood to flow from a location within the main vein that is upstream of the tributary veins to the location within the main vein that is downstream of the tributary veins without being pumped by the pump, by directing the blood to bypass the pump. The scope of some applications of the present invention further includes apparatus and methods for use with a venous system of a subject that includes tributary vessels (e.g., lymphatic vessels) that flow into a vein. Typically, such methods include separating flow within a region of the vein that is adjacent to junctions of the vein with the tributary vessels from bloodstream within the vein upstream and downstream thereto, pumping blood from the region of the vein that is adjacent to junctions of the vein with the tributary vessels to a location within the vein that is downstream of the region, using a pump, and allowing the subject's blood to flow from a location within the vein that is upstream of the tributary vessels to the location within the vein that is downstream of the tributary vessels without being pumped by the pump, by directing the blood to bypass the pump.

For some applications of the present invention, a blood-pump catheter includes an impeller configured to pump blood by rotating, and an impeller housing that is configured to be disposed around the impeller. A blood-pump-support frame is typically configured to be disposed upstream of impeller housing, and to at least partially align a longitudinal axis of the impeller housing with a local longitudinal axis of the blood vessel, by contacting the inner wall of the blood vessel. A material is configured to extend from the impeller housing to the blood-pump-support frame, such as to contact the vessel wall and to occlude the blood vessel in the region of the blood vessel that surrounds the impeller. For some applications, the material defines a blood-outlet opening, and the impeller is configured to pump blood through the blood-outlet opening.

For some applications, a blood-pump catheter is configured for use with a subject's descending aorta. The blood-pump catheter includes a material configured to be placed within the descending aorta and to separate the aorta into upstream and downstream compartments by at least partially occluding blood flow through the aorta. The material typically defines a blood-outlet opening. A blood pump (e.g., an impeller-based blood pump) is configured to pump blood in a downstream direction through the descending aorta, through the blood-outlet opening.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

The terms "downstream" and "upstream" and related terms should be interpreted as being defined with respect to the direction of antegrade blood flow through a subject's vasculature. Thus, by way of example, the suprarenal vena cava is downstream of the infrarenal vena cava, and the descending aorta is downstream of the aortic arch. When used with reference to a device, the term "upstream" should be interpreted as referring to a portion of the device that it configured to be disposed at a relatively upstream location, and the term "downstream" should be interpreted as referring to a portion of the device that it configured to be disposed at a relatively downstream location.

There is therefore provided, in accordance with some applications of the present invention, apparatus for use with a venous system of a subject that includes one or more tributary vessels that flow into a vein at junctions between the vein and the one or more tributary vessels, the apparatus including:
  a blood-pump-catheter including:
  a material configured to be placed at a downstream location that is downstream of the junctions and to at least partially occlude blood flow through the vein at the downstream location, the material defining a blood-outlet opening;
  a blood pump configured to pump blood from a region of the vein that is adjacent to the junctions, and through the blood-outlet opening defined by the material;
  a blood-flow pathway that passes between (a) a pathway-inlet opening disposed at an upstream location that is upstream of the junctions and (b) a pathway-outlet opening that opens to a downstream side of the material,
  the blood-flow pathway being configured to direct upstream venous blood flow from the upstream location to downstream of the material, without the upstream venous blood flow being pumped by the pump.

In some applications, the blood pump includes an elongate blood-pump tube, the elongate blood-pump tube defining a blood-inlet area which is disposed within an upstream portion of the elongate blood-pump tube, a blood-outlet area that is that is disposed within a downstream portion of the elongate blood-pump tube, and an impeller configured to pump blood into the blood-inlet area, through the elongate blood-pump tube, and out of the blood-outlet area.

In some applications, the blood pump includes an impeller that is disposed within a frame, the impeller being configured to pump blood by rotating within the frame.

In some applications, the blood-pump catheter is configured for use with one or more lymphatic vessels that flow into a vein, and the blood-pump catheter is configured to be placed within the vein, such that:
  the material is placed at a downstream location that is downstream of junctions of the vein with the one or more lymphatic vessels and such as to at least partially occlude blood flow through the vein at the downstream location, the blood pump is configured to pump blood from a region of the vein that is adjacent to the junctions of the vein with the one or more lymphatic vessels, and through the blood-outlet opening defined by the material, and the blood-flow pathway passes between (a) the pathway-inlet opening, the pathway-inlet opening being disposed at an upstream location that is upstream of the region of the vein that is adjacent to the junctions of the vein and the one or more lymphatic vessels and (b) the pathway-outlet opening, the pathway-outlet opening opening to the downstream side of the material, the blood-flow pathway being configured to direct upstream venous blood flow from the upstream location to the downstream side of the material, without the upstream venous blood flow being pumped by the pump.

In some applications, the blood-pump catheter is configured to be placed within a vena cava of the subject, such that:

the material is placed at a downstream location that is downstream of junctions of the vena cava with one or more renal veins of the subject and such as to at least partially occlude blood flow through the vena cava at the downstream location, the blood pump is configured to pump blood from a region of the vena cava that is adjacent to the junctions of the vena cava with the one or more renal veins through the blood-outlet opening defined by the material, and the blood-flow pathway passes between (a) the pathway-inlet opening, the pathway-inlet opening being disposed at an upstream location that is upstream of junctions of the vena cava and the one or more renal veins and (b) the pathway-outlet opening, the pathway-outlet opening opening to the downstream side of the material, the blood-flow pathway being configured to direct blood flow from an infrarenal vena-caval bloodstream to downstream of the material, without the infrarenal vena-caval bloodstream being pumped by the pump.

In some applications, the apparatus further includes a percutaneous left-ventricular assist device configured to assist with left-ventricular functioning of the subject.

In some applications, the blood pump includes an elongate blood-pump tube, the elongate blood-pump tube defining a blood-inlet area which is disposed within an upstream portion of the elongate blood-pump tube, a blood-outlet area that is that is disposed within a downstream portion of the elongate blood-pump tube, and an impeller configured to pump blood into the blood-inlet area, through the elongate blood-pump tube, and out of a blood-outlet area.

In some applications, the elongate blood-pump tube is configured to be disposed such that the blood-outlet area is disposed within a pulmonary artery of the subject and is configured to pump blood into the subject's pulmonary artery via the elongate tube.

In some applications, the apparatus further includes an elongate tube that extends downstream from the material and that defines suprarenal blood-inlet openings that are configured to be disposed within a suprarenal vena cava of the subject, and the blood-inlet area of the elongate blood-pump tube is configured to be disposed downstream of the suprarenal blood-inlet openings and the elongate blood-pump tube is configured to pump blood from a suprarenal vena-caval bloodstream into the subject's pulmonary artery.

In some applications, the apparatus further includes an elongate tube that is configured to extend into a pulmonary artery of the subject, and the blood pump is configured to pump blood into the subject's pulmonary artery via the elongate tube.

In some applications, the elongate tube defines suprarenal blood-inlet openings that are configured to be disposed within a suprarenal vena cava of the subject, and the blood pump is configured to be disposed downstream of the suprarenal blood-inlet openings and is configured to pump blood from a suprarenal vena-caval bloodstream into the subject's pulmonary artery.

In some applications, diameters of one or more portions of the blood-flow pathway are modulable, such that flow from the infrarenal vena-caval bloodstream to a right atrium of the subject is modulable.

In some applications, the apparatus further includes a blood pressure sensor configured to detect blood pressure of the subject, and a computer processor configured to receive the subject's blood pressure and to automatically modulate the diameters of the one or more portions of the blood-flow pathway, in response to the detected blood pressure.

In some applications, the diameters of the one or more portions of the blood-flow pathway are configured to be modulated in response to an input.

In some applications, the blood-flow pathway includes a funnel having a wide end and a narrow end, and one or more tubes, and the wide end of the funnel defines the pathway-inlet opening, and the narrow end of the funnel passes into the one or more tubes.

In some applications, the funnel and the one or more tubes include a single continuous blood-flow pathway.

In some applications, diameters of one or more portions of the blood-flow pathway are modulable, such that flow through the blood-flow pathway is modulable.

In some applications, the apparatus further includes a blood pressure sensor configured to detect blood pressure of the subject, and a computer processor configured to receive the subject's blood pressure and to automatically modulate the diameters of the one or more portions of the blood-flow pathway, in response to the detected blood pressure.

In some applications, the diameters of the one or more portions of the blood-flow pathway are configured to be modulated in response to an input.

There is further provided, in accordance with some applications of the present invention, apparatus including:
  a blood-pump-catheter including:
    a material disposed upon the blood-pump catheter and configured to at least partially occlude blood flow through a vein, the material defining a blood-outlet opening;
    a blood pump configured to pump blood through the blood-outlet opening defined by the material;
    a blood-flow pathway that passes between (a) a pathway-inlet opening disposed at a location that is proximal with respect to the material and (b) a pathway-outlet opening that opens to a location that is distal with respect to the material,
    the blood-flow pathway being configured to direct blood flow from the pathway-inlet opening to the pathway-outlet opening, without the blood flow being pumped by the pump.

There is further provided, in accordance with some applications of the present invention, a method for use with a venous system of a subject that includes tributary vessels that flow into a vein at junctions between the vein and the tributary vessels, the method including:

separating a bloodstream of a region of the vein that is adjacent to the junctions into a compartment that is separate from bloodstream within the vein that is upstream of the junctions and from bloodstream within the vein that is downstream of the junctions;

pumping blood from the compartment to downstream of the compartment, using a pump; and allowing the subject's blood to flow from a location within the vein that is upstream of the compartment to a location that is downstream of the compartment without being pumped by the pump, by directing the blood to bypass the pump.

In some applications, pumping blood from the compartment to downstream of the compartment includes pumping blood from the compartment to downstream of the compartment via an elongate blood-pump tube, the elongate blood-pump tube defining a blood-inlet area disposed within an upstream portion of the elongate blood-pump tube, a blood-outlet area that is disposed within a downstream portion of the elongate tube, and an impeller configured to pump blood into the blood-inlet area, through the elongate blood-pump tube, and out of the blood-outlet area.

In some applications, pumping blood from the compartment to downstream of the compartment includes pumping blood from the compartment to downstream of the compartment by rotating an impeller.

In some applications, the method is for use with one or more lymphatic vessels that flow into a vein, and the method includes:

separating bloodstream within a region of the vein that is adjacent to junctions of the vein with the one or more lymphatic vessels into a compartment that is separate from bloodstream within the vein downstream of the region of the vein that is adjacent to the junctions of the vein with the one or more lymphatic vessels, and from bloodstream within the vein upstream of the region of the vein that is adjacent to the junctions of the vein with the one or more lymphatic vessels;

pumping blood from the compartment to downstream of the compartment, using the pump; and allowing the subject's blood to flow from a location within the vein that is upstream of the compartment to a location that is downstream of the compartment without being pumped by the pump, by directing the blood to bypass the pump.

In some applications, the method is for use with renal veins and a vena cava of the subject, and the method includes:

separating bloodstream within a region of the vena cava that is adjacent to the junctions of the vena cava with the one or more the renal veins into a vena-caval compartment that is separate from bloodstream within the vena cava downstream of the vena-caval compartment, and from bloodstream within the vena cava upstream of the vena-caval compartment;

pumping blood from the vena-caval compartment to downstream of the vena-caval compartment, using the pump; and allowing the subject's blood to flow from a location that is upstream of the vena-caval compartment to a location that is downstream of the vena-caval compartment without being pumped by the pump, by directing the blood to bypass the pump.

In some applications, the method further includes assisting left-ventricular functioning of the subject using a percutaneous left-ventricular assist device.

In some applications, pumping blood from the vena-caval compartment to downstream of the vena-caval compartment includes pumping blood from the vena-caval compartment to downstream of the vena-caval compartment via an elongate blood-pump tube, the elongate blood-pump tube defining a blood-inlet area which is disposed within an upstream portion of the elongate blood-pump tube, a blood-outlet area that is that is disposed within a downstream portion of the elongate blood-pump tube, and an impeller configured to pump blood into the blood-inlet area, through the elongate blood-pump tube, and out of the blood-outlet area.

In some applications, pumping blood from the vena-caval compartment to downstream of the vena-caval compartment via the elongate blood-pump tube includes pumping blood into the subject's pulmonary artery via the elongate tube.

In some applications, the method further includes pumping blood from a suprarenal vena-caval bloodstream of the subject into the subject's pulmonary artery, via the elongate blood-pump tube.

In some applications, pumping blood from the vena-caval compartment to downstream of the vena-caval compartment includes pumping blood into a pulmonary artery of the subject via an elongate tube.

In some applications, the method further includes pumping blood from a suprarenal vena-caval bloodstream of the subject into the subject's pulmonary artery via the elongate tube.

In some applications, directing the blood to bypass the pump includes directing the blood to bypass the pump via a blood-flow pathway, the method further including modulating blood flow to a right atrium of the subject by modulating diameters of one or more portions of the blood-flow pathway.

In some applications, the method further includes detecting blood pressure of the subject, and modulating diameters of one or more portions of the blood-flow pathway includes automatically modulating the diameters of the one or more portions of the blood-flow pathway, in response to the detected blood pressure.

In some applications, modulating diameters of one or more portions of the blood-flow pathway includes modulating diameters of one or more portions of the blood-flow pathway in response to an input.

In some applications, directing the blood to bypass the pump includes directing the blood to bypass the pump via a blood-flow pathway, the method further including modulating blood flow through the blood-flow pathway by modulating diameters of one or more portions of the blood-flow pathway.

In some applications, the method further includes detecting blood pressure of the subject, and modulating diameters of one or more portions of the blood-flow pathway includes automatically modulating the diameters of the one or more portions of the blood-flow pathway, in response to the detected blood pressure.

In some applications, modulating diameters of one or more portions of the blood-flow pathway includes modulating diameters of one or more portions of the blood-flow pathway in response to an input.

There is further provided, in accordance with some applications of the present invention, a method for use with a venous system of a subject that includes tributary vessels that flow into a vein at junctions between the tributary vessels and the vein, the method including:

at least partially occluding blood flow through the vein by placing a downstream occluding element at a downstream location that is downstream of junctions of the vein with the tributary vessels;

pumping blood from a region of the vein that is adjacent to the junctions of the vein with the tributary vessels through the downstream occluding element, using a pump; and directing upstream venous blood flow from an upstream location that is upstream of junctions of the vein with the tributary vessels to downstream of the occluding element, without the upstream venous blood flow being pumped by the pump, by directing the upstream venous blood flow to bypass the pump.

There is further provided, in accordance with some applications of the present invention, a method for use with a venous system of a subject that includes tributary vessels that flow into a vein at junctions between the tributary vessels and the vein, the method including:

separating a bloodstream of a region of the vein that is adjacent to the junctions from bloodstream within the vein that is upstream of the region of the vein that is adjacent to the junctions and from bloodstream within the vein that is downstream of the region of the vein that is adjacent to the junctions;

allowing blood to flow from the tributary vessels to a location that is downstream of the tributary vessels, via a first flow path;

allowing the subject's blood to flow from a location within the vein that is upstream of the tributary vessels to a location within the vein that is downstream of the tributary vessels, via a second flow path; and controlling blood flow via at least one of the first and second flow paths.

There is further provided, in accordance with some applications of the present invention, apparatus for use with an arterial system of a subject that includes a main artery and one or more branching arteries that branch from the main artery at junctions between the main artery and the one or more branching arteries, the apparatus including:

a blood-pump-catheter including:
a material configured to be placed at a downstream location that is downstream of the junctions between the main artery with the branching arteries and to at least partially occlude blood flow through the main artery at the downstream location, the material defining a blood-inlet opening;
a blood pump configured to pump blood from the main artery toward the branching arteries, through the blood-inlet opening;
a funnel configured to be disposed at an upstream location that is upstream of junctions of the main artery with the branching arteries; and
a blood-flow pathway that passes between (a) a pathway-inlet opening disposed at an upstream location that is upstream of junctions of the main artery with the branching arteries and (b) a pathway-outlet opening that opens to a downstream side of the material,
the blood-flow pathway being configured to direct upstream main arterial blood flow from the upstream location to downstream of the material, without the upstream main arterial blood flow being pumped by the pump.

There is further provided, in accordance with some applications of the present invention, a method for use with an arterial system of a subject that includes a main artery and one or more branching arteries that branch from the main artery at junctions between the main artery and the one or more branching arteries, the method including:

separating bloodstream within a region of the main artery that is adjacent to the junctions into a compartment that is separate from bloodstream within the main artery that is downstream from the compartment and from bloodstream within the compartment;

pumping blood from the main artery to the branching arteries, using a pump; and allowing the subject's blood to flow from a location within the main artery that is upstream of the compartment to a location that is downstream of the compartment without being pumped by the pump, by directing the blood to bypass the pump.

There is further provided, in accordance with some applications of the present invention, a method for use with an arterial system of a subject that includes a main artery and one or more branching arteries that branch from the main artery at junctions between the main artery and the one or more branching arteries, the method including:

at least partially occluding blood flow through the main artery by placing a downstream occluding element at a downstream location that is downstream of junctions of the main artery with the branching arteries;

pumping blood from the main artery to the branching arteries, through the downstream occluding element, using a pump; and directing upstream main artery blood flow from an upstream location that is upstream of junctions of the main artery with the branching arteries to downstream of the occluding element, without the upstream main artery blood flow being pumped by the pump, by directing the upstream main artery blood flow to bypass the pump.

There is further provided, in accordance with some applications of the present invention, apparatus for use with a descending aorta of a subject, the apparatus including:

a blood-pump-catheter including:
a material configured to be placed within the descending aorta and to separate the aorta into upstream and downstream compartments by at least partially occluding blood flow through the aorta, the material defining a blood-outlet opening;
a blood pump configured to pump blood in a downstream direction through the descending aorta, through the blood-outlet opening.

There is further provided, in accordance with some applications of the present invention, a method for use with a descending aorta of a subject, the method including:

separating the descending aorta into upstream and downstream compartments by placing an occluding element into the descending aorta that at least partially occludes the descending aorta; and pumping blood from the upstream compartment to the downstream compartment using a blood pump.

There is further provided, in accordance with some applications of the present invention, apparatus including:

a blood-pump catheter configured to be placed inside a blood vessel of a subject, the blood-pump catheter including:
an impeller configured to pump blood by rotating;
an impeller housing that is configured to be disposed around the impeller;
a blood-pump-support frame configured to be disposed upstream of the impeller housing, and to at least partially align a longitudinal axis of the impeller housing with a local longitudinal axis of the blood vessel, by contacting the inner wall of the blood vessel; and
a material configured to extend from the impeller housing to the blood-pump-support frame, such as to contact the vessel wall and to occlude the blood vessel in the region of the blood vessel that surrounds the impeller, the material defining a blood-outlet opening, the impeller being configured to pump blood through the blood-outlet opening.

The present invention will be more fully understood from the following detailed description of embodiments thereof, taken together with the drawings, in which:

BRIEF DESCRIPTION OF THE DRAWINGS

FIGS. 6A, 6B, 6C, 6D, 6E, 6F, 6G, and 6H are schematic illustrations of an impeller of a blood pump or a portion thereof, in accordance with some applications of the present invention;

DETAILED DESCRIPTION OF EMBODIMENTS

Figure 1A:
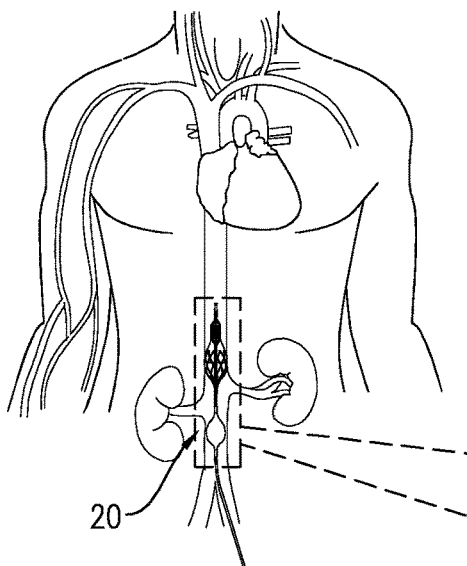
FIGS. 1A, 1B, and 1C are schematic illustrations of a blood-pump catheter placed within a subject's vena cava, in accordance with some applications of the present invention.
Figure 1A:
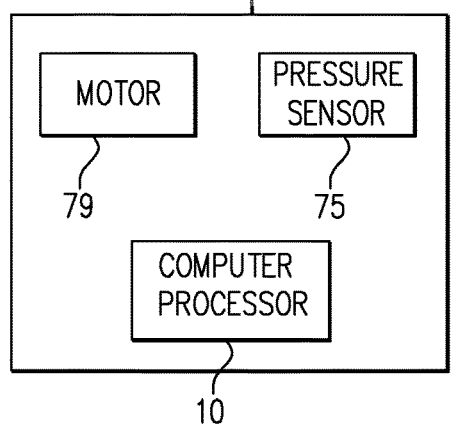
Figure 1A:
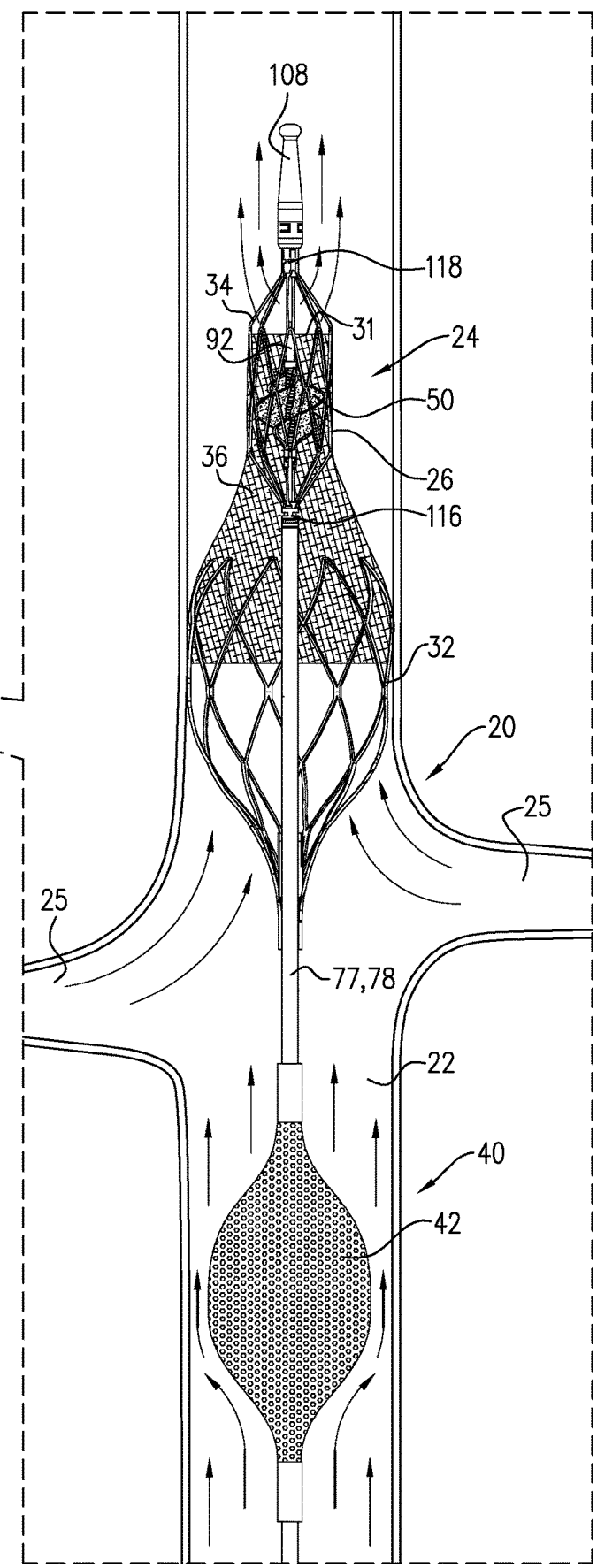
Figure 1B:
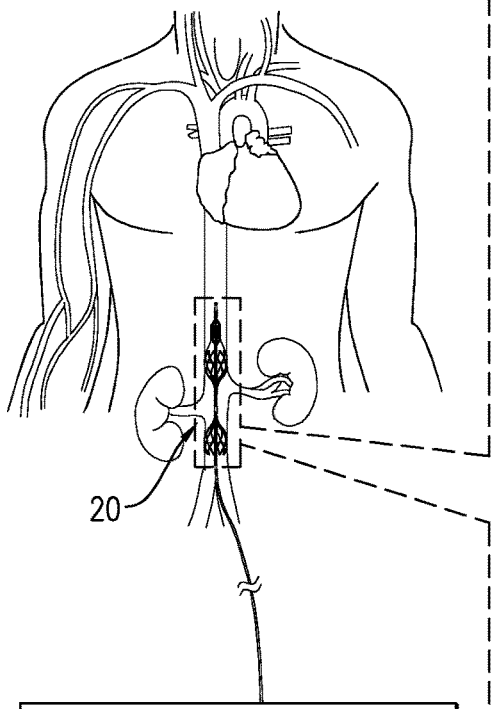
Figure 1B:
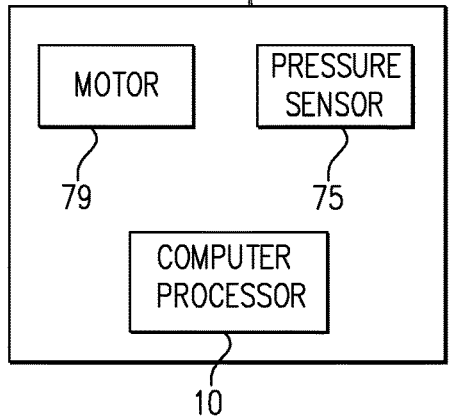
Figure 1B:
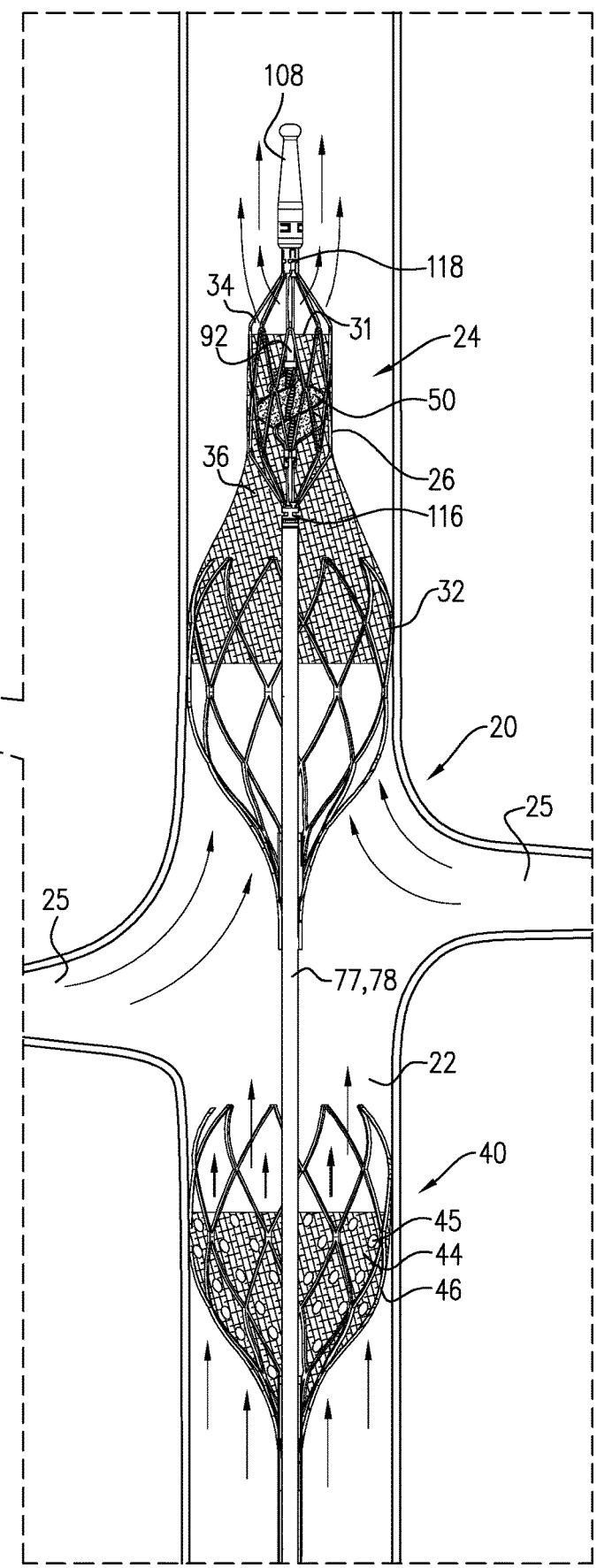
Figure 1C:
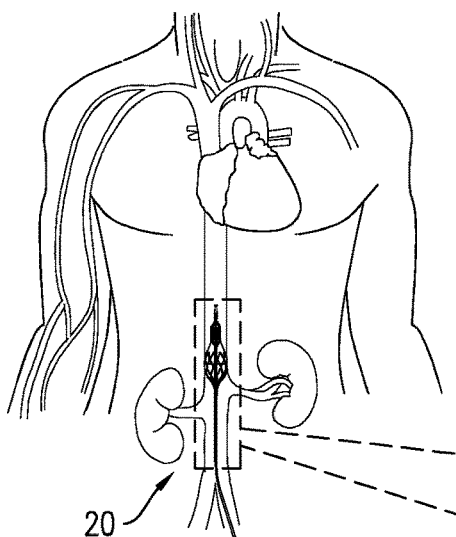
Figure 1C:
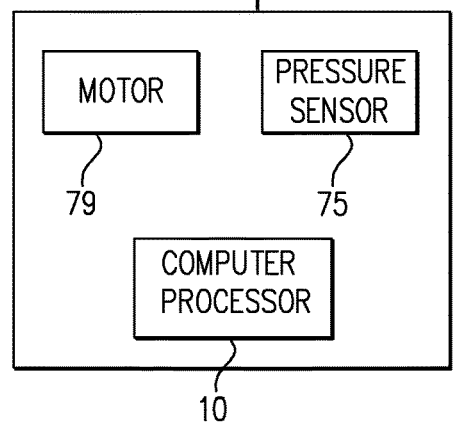
Figure 1C:
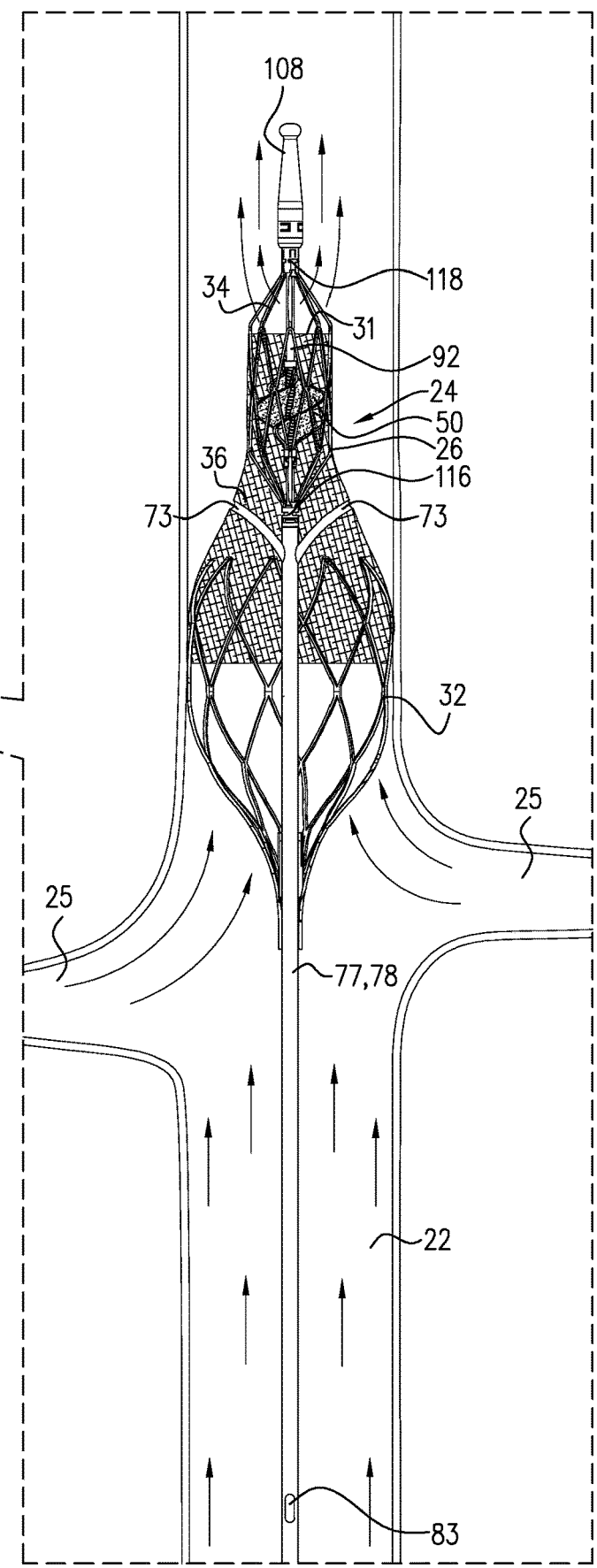

Reference is made to FIGS. 1A-C, which are schematic illustrations of a blood-pump catheter 20 placed within a subject's vena cava 22, in accordance with some applications of the present invention. Typically, the blood-pump catheter includes a blood pump 24 that includes an impeller housing 26, and an impeller 50 disposed inside the impeller housing. Impeller housing 26 (e.g., a frame 34 of the housing) typically functions to separate the inner wall of the vena cava from the impeller (e.g., in case the vena cava collapses inwardly due to intra-abdominal pressure), such that the vena cava does not become injured by the impeller and the impeller does not become deformed by pressure from the inner wall of the vena cava. Further typically, an axial shaft 92 (shown in FIG. 7) that passes through the impeller is supported by radial bearings 116, 118 disposed, respectively, at proximal and distal ends of the impeller housing.

It is noted that, for illustrative purposes, in FIGS. 1A-C (as well as in FIGS. 2A-E, 3A-H, 4A-B, and 5A-B), a three-dimensional view of blood pump 24 is shown, but cross-sectional views are shown of other elements of the blood-pump catheters.

For some such applications, a blood-pump-support frame 32 is disposed upstream of impeller housing 26, and is configured to come into contact with the inner wall of the vena cava. Blood-pump-support frame 32 is configured to align the longitudinal axis of impeller housing 26, and, in turn, impeller 50, with the local longitudinal axis of the vena cava, by contacting the inner wall of the vena cava. (It is noted that, for some applications, the blood-pump-support frame may not fully align the longitudinal axis of impeller with the local longitudinal axis of the vena cava. However, typically, the blood-pump-support frame maintains the longitudinal axis of the impeller in greater alignment with the local longitudinal axis of the vena cava, relative to alignment of the longitudinal axis of the impeller with the local longitudinal axis of the vena cava in the absence of the blood-pump-support frame.) Typically, ceteris paribus, the efficacy of the pumping of blood by impeller 50 is greater, the greater the alignment of the longitudinal axis of the impeller with the local longitudinal axis of the vena cava. It is noted that a slight misalignment of the of the longitudinal axis of the impeller with the local longitudinal axis of the vena cava (e.g., as shown in FIG. 2E), will nevertheless typically still result in efficacious pumping of blood by the impeller.

For some applications, impeller housing 26 includes a frame 34 (e.g., a rigid or semi-rigid frame) made of a shape-memory element (such as nitinol) that is at least partially covered with a material 36 (e.g., a blood-impermeable material, e.g., polyester, polyurethane, and/or a different polymer). Typically, for such applications, the stiffness of frame 34 is sufficiently great that pressure exerted upon the frame 34 by the inner wall of the vena cava does not deform the frame. Typically, material 36 extends from the impeller housing to blood-pump-support frame 32 such as to contact the vessel wall and to occlude the blood vessel in the region of the blood vessel that surrounds the impeller and/or that is upstream of the impeller. The material typically defines a hole therethrough at a distal portion of the impeller housing. The material is configured to occlude backflow of blood around the outside of the impeller, but such to allow antegrade blood flow in the central region of the vessel in the vicinity of the impeller, by the hole acting as a blood-outlet opening 31. For some applications, a portion of the impeller housing is covered (i.e., lined) on the inside of the impeller housing with an inner lining 39, e.g., as described hereinbelow with reference to FIG. 7. For some such applications, the inner lining of the impeller housing at least partially overlaps with material 36. For some applications, the inner lining extends the blood-outlet opening defined by material 36.

Figure 7:
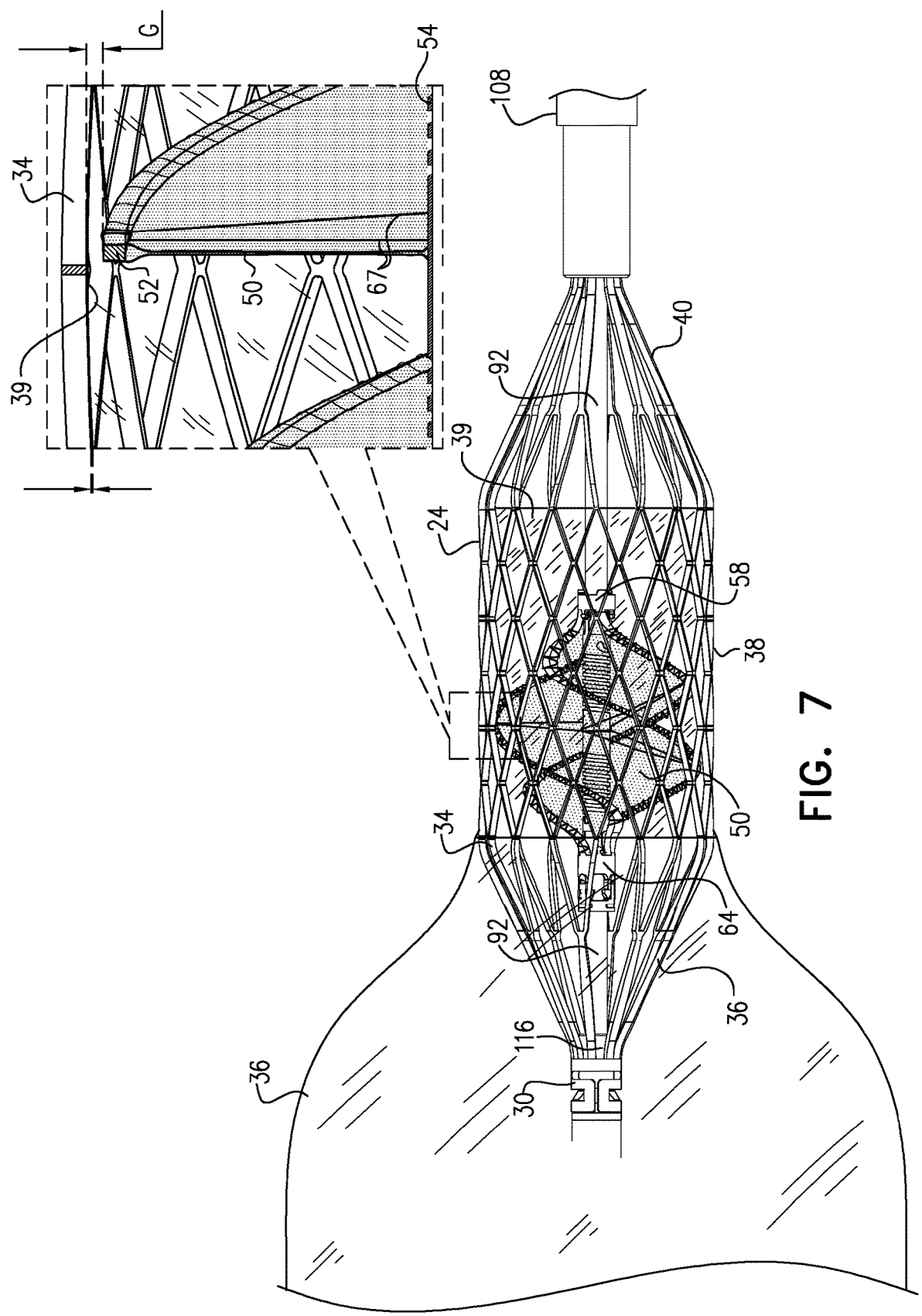
FIG. 7 is a schematic illustration of an impeller disposed inside a frame of a blood pump, in accordance with some applications of the present invention.
Figure 8A:
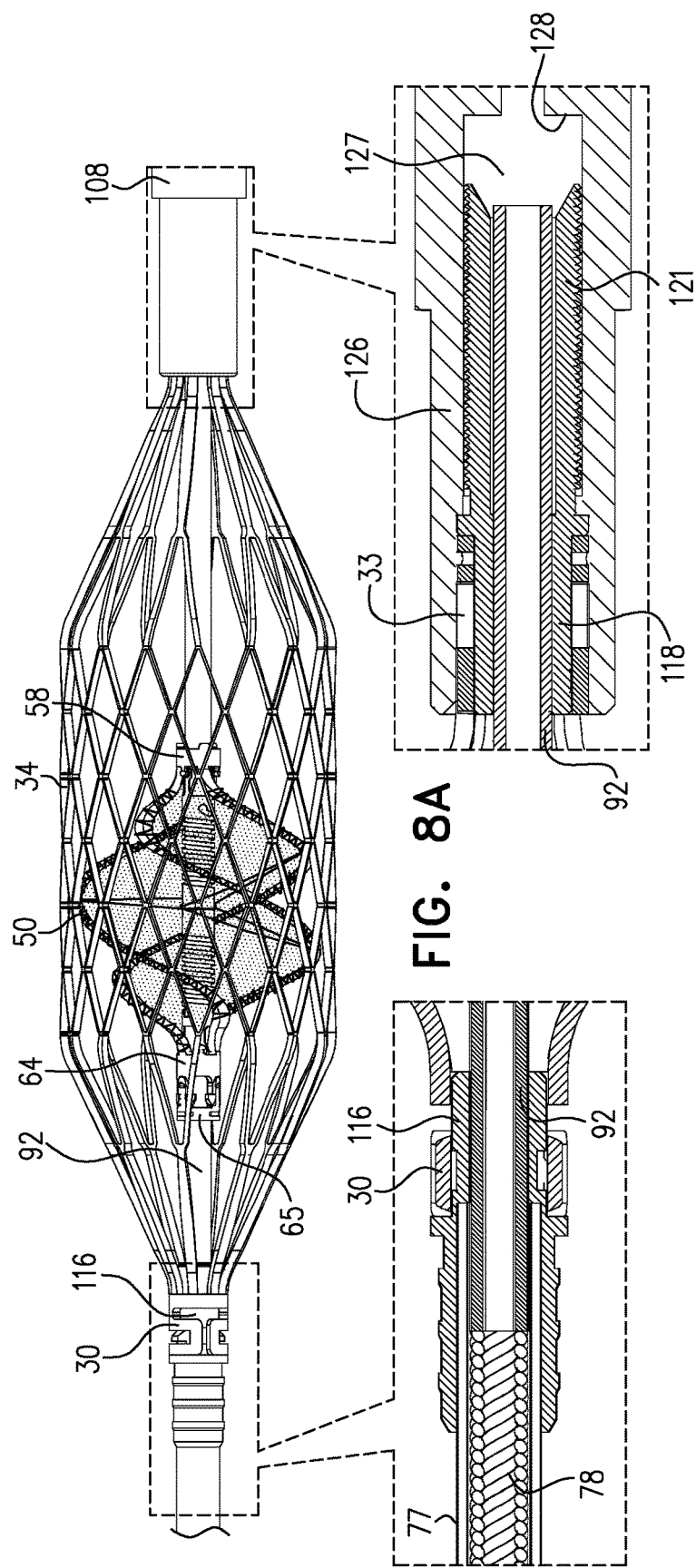
FIGS. 8A and 8B are schematic illustrations of the impeller and the frame of the blood pump, respectively, in non-radially-constrained and radially-constrained states thereof, in accordance with some applications of the present invention.

Typically, a drive cable 78 is disposed within an outer tube 77 of blood-pump catheter 20. (The drive cable is shown in FIG. 8A, for example.) Further typically, the drive cable extends from a motor 79 which is disposed outside the subject's body, to axial shaft 92 (shown in FIG. 7), upon which the impeller is disposed. The motor imparts rotational motion to the axial shaft (and thereby imparts rotational motion to the impeller), via the drive cable. Typically, the motor is controlled by a computer processor 10. For some applications, the motor is controlled based upon blood pressure measurements that are performed by a pressure sensor 75.

For some applications, the use of material 36 in the above-described manner reduces a likelihood of there being retrograde blood flow in the region of the blood vessel that surrounds the impeller, caused by turbulence that is introduced by the impeller. For some applications, the material acts to separate the suprarenal vena cava into upstream and downstream compartments, and the impeller is configured to pump blood from the upstream compartment to the downstream compartment, thereby reducing pressure in the upstream compartment, in the vicinity of the renal veins.

For some applications (not shown), blood-pump-support frame 32 and frame 34 of impeller housing 26 are formed as a single frame having an upstream portion that is configured to come into contact with the inner wall of the vena cava, and a downstream portion that is configured to house the impeller.

Typically, the maximum diameter of blood-pump-support frame 32 (i.e., the diameter of the blood-pump-support frame 32 at the longitudinal location(s) at which the diameter of the blood-pump-support frame 32 is at its maximum), when the blood-pump-support frame is in a radially non-constrained configuration thereof, is at least 1.1 times (and, for some applications, at least 1.3 times) greater than the maximum diameter of frame 34 of impeller housing 26 (i.e., the diameter of frame 34 at the longitudinal location(s) at which the diameter of frame 34 is at its maximum) when frame 34 is in a radially non-constrained configuration thereof.

Typically, blood pump 24 is placed downstream of junctions of the vena cava with the subject's renal veins 25, and is configured to pump blood in the downstream direction, such as to reduce pressure in the subject's renal veins. For some applications, blood-pump catheter 20 includes an occlusion element 40 that is configured to be placed upstream of junctions of the vena cava with the subject's renal veins, and to partially occlude the vena cava at this location. For example, the occlusion element may include a balloon 42, as shown in FIG. 1A. Alternatively or additionally, the occlusion element includes a blood-impermeable material 44 that defines holes 45 therethrough, as shown in FIG. 1B. For some applications, the material is supported by a frame 46. Typically, material 44 is configured such that there is some blood flow via the holes in the material, but the blood flow is reduced relative to in the absence of the material. Typically, the occlusion element is configured to partially occlude the subject's vena cava upstream of the junctions of the vena cava with the subject's renal veins. For some applications (not shown), a nozzle is used as the upstream occlusion element, e.g., as described in US 2019/0239998 to Tuval, which is incorporated herein by reference.

Occlusion element 40 is configured to partially occlude the subject's vena cava such that, in response to the pumping of the downstream blood pump, there is not a substantial increase of blood flow from the subject's lower body toward the subject's heart, but such that a region of low pressure within the vena cava is generated between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava.

For some applications, blood-pump catheter 20 does not include an upstream occlusion element, e.g., as shown in FIG. 1C. As described hereinabove, for some applications, material 36 acts to separate the suprarenal vena cava into upstream and downstream compartments, and impeller 50 is configured to pump blood from the upstream compartment to the downstream compartment, thereby reducing pressure in the upstream compartment, in the vicinity of the renal veins. For some applications, blood-pump catheter 20 is thereby configured to generate a region of low pressure within the vena cava, in the vicinity of the renal veins, even in the absence of an upstream occlusion element, as shown in FIG. 1C. Typically, by generating a region of low pressure, blood flow from the renal veins into the vena cava increases, thereby lowering renal blood pressure and enhancing renal perfusion.

Blood-pump catheter 20 is typically placed inside the subject's vena cava 22, and operated therein, in order to provide acute treatment of a subject suffering from cardiac dysfunction, congestive heart failure, low renal blood flow, high renal vascular resistance, arterial hypertension, diabetes, and/or kidney dysfunction. For example, the blood-pump catheter may be placed inside the subject's vena cava, and operated therein, for a period of more than one hour (e.g., more than one day), less than one week (e.g., less than four days), and/or between one hour and one week (e.g., between one day and four days). For some applications, the blood-pump catheter is chronically placed inside the subject's vena cava in order to provide chronic treatment of a subject suffering from cardiac dysfunction, congestive heart failure, low renal blood flow, high renal vascular resistance, arterial hypertension, diabetes, and/or kidney dysfunction. For some applications, a course of treatment is applied to a subject over several weeks, several months, or several years, during which the blood-pump catheter is intermittently placed inside the subject's vena cava, and the subject is intermittently treated in accordance with the techniques described herein. For example, the subject may be intermittently treated at intervals of several days, several weeks, or several months.

With respect to the catheter shown in FIGS. 1A-B, it is noted that such a catheter, which includes blood pump 24 that is disposed distally with respect to an upstream occlusion element, is suitable for placement into the vena cava from a vein that is below the junctions of the vena cava with the subject's renal veins, e.g., the femoral vein. However, the scope of the present invention includes a catheter that has a pump and an occlusion element disposed thereon, but with the upstream occlusion element disposed distally with respect to the downstream pump. Such a catheter is typically inserted via a vein that is disposed above the inferior vena cava, e.g., the subclavian vein or the jugular vein, mutatis mutandis. Similarly, a catheter as generally shown in FIG. 1C may be configured for insertion into the suprarenal vena cava via a vein that is disposed above the inferior vena cava, e.g., the subclavian vein or the jugular vein, mutatis mutandis. Typically, in such cases, the dispositions of components of the blood-pump catheter with respect to the shaft of the catheter are in the opposite direction from that shown in FIGS. 1A-C.

Typically, the blood-pump catheter is inserted under fluoroscopic imaging. Alternatively, the blood-pump catheter is inserted under ultrasound imaging, such as to reduce exposure of the subject to radiation and/or contrast agent.

As described hereinabove, typically blood-pump catheter 20 is placed inside the vena cava of a subject suffering from cardiac dysfunction, congestive heart failure, low renal blood flow, high renal vascular resistance, arterial hypertension, diabetes, and/or kidney dysfunction. Typically, operating the blood-pump catheter in the vena cava of such a subject causes a lowering and flattening of the subject's renal vein pressure profile, even though the subject's central venous pressure is elevated and has additional effects, e.g., as described with reference to FIG. 4B of US 2016/0022890 to Schwammenthal, which is incorporated herein by reference.

As described hereinabove, typically, the occlusion element is configured to partially occlude the vena cava upstream of the junctions of the vena cava with the subject's renal veins. For some applications, the diameter to which the occlusion element is expanded is controllable. For example, inflation of the balloon may be controllable, or the frame may be expandable (e.g., by heating the frame, or by applying an electrical current to the frame). For some applications, the extent to which the occlusion element occludes the vena cava is controlled by a computer processor 10 responsively to the blood pressure detected by blood pressure sensor 75, in response to an input from a different sensor (such as a flow sensor and/or an oxygen-saturation sensor, and/or a thermal flow sensor, e.g., as described with reference to FIGS. 22Ai-Cii of US 2016/0022890 to Schwammenthal, which is incorporated herein by reference), and/or in response to an input from a user. For some applications, the rate at which pump 24 pumps blood away from the renal veins (e.g., the rate at which impeller 50 of the pump is rotated), and/or the extent to which the occlusion element occludes the vena cava, is controlled by computer processor 10, responsively to the blood pressure detected by blood pressure sensor 75, in response to an input from a different sensor (such as a flow sensor and/or an oxygen-saturation sensor, and/or a thermal flow sensor, e.g., as described with reference to FIGS. 22Ai-Cii of US 2016/0022890 to Schwammenthal, which is incorporated herein by reference), and/or in response to an input from a user. For some applications, a blood pressure sensor as described hereinbelow with reference to FIGS. 1C and 2C is used in conjunction with the above-described apparatus and methods.

Although some applications of the present invention are described with reference to blood pumps, according to which the blood pumps include impellers, the scope of the present invention includes using any other type of pump for pumping blood in the manner described herein, mutatis mutandis. For example, a roller pump, an Archimedes screw pump, a centrifugal pump, a pneumatic pump, and/or a compression pump may be used.

With reference to FIGS. 1A-C, it is noted that the scope of the present invention includes applying similar apparatus and methods to any venous system of a subject that includes tributary veins that flow into a main vein. For example, similar techniques could be applied at junctions of the hepatic veins and the vena cava. For some applications, generally similar apparatus and methods are used within the subclavian vein or jugular vein, at junctions of the vein with one or more lymphatic vessels. For some such applications, blood-pump catheter 20 is configured to increase flow of lymphatic fluid from the lymphatic vessels into the vein, mutatis mutandis.

Figure 2A:
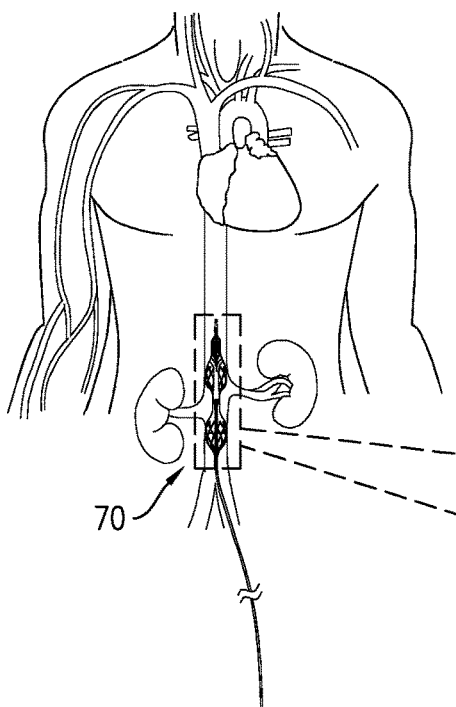
FIGS. 2A, 2B, and 2C are schematic illustrations of a blood-pump catheter placed within a subject's vena cava, in accordance with some applications of the present invention.
Figure 2A:
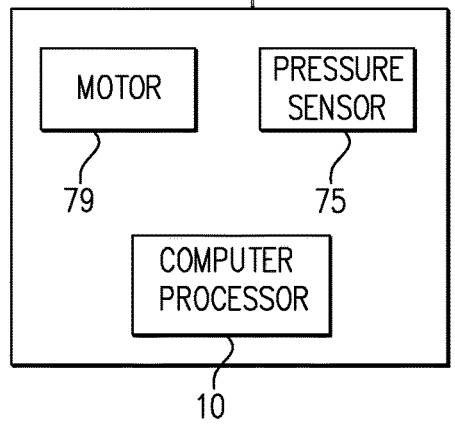
Figure 2A:
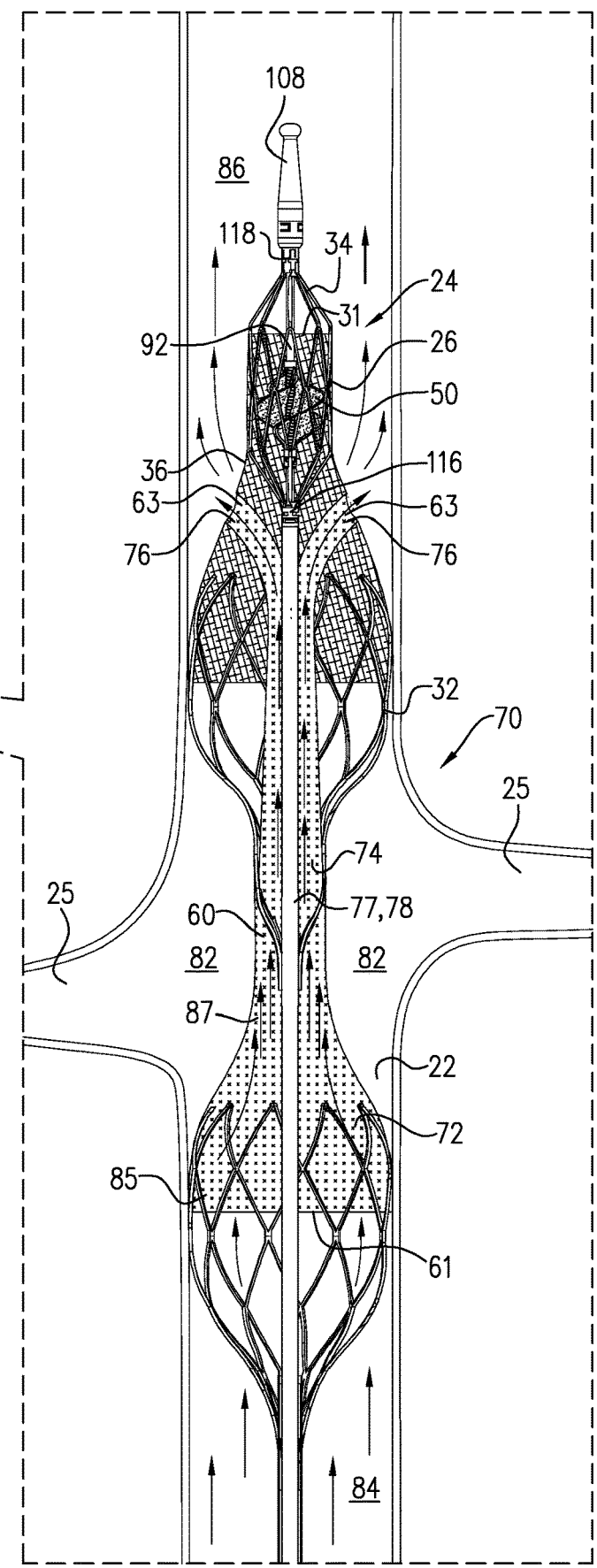
Figure 2B:
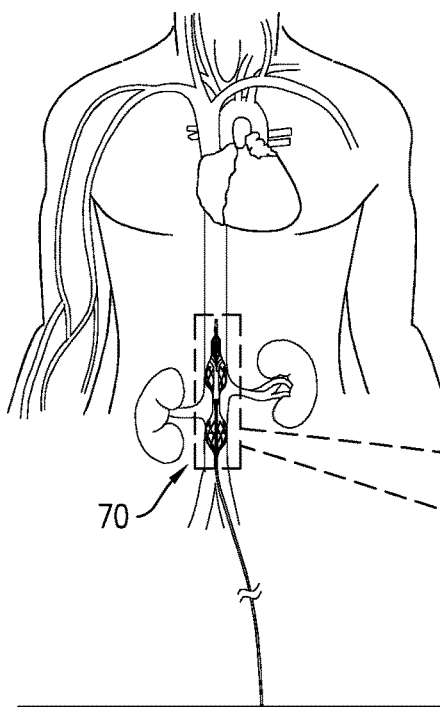
Figure 2B:
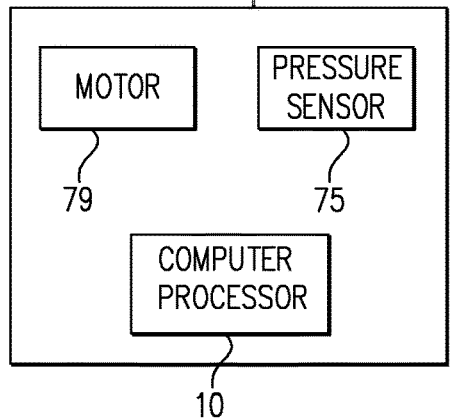
Figure 2B:
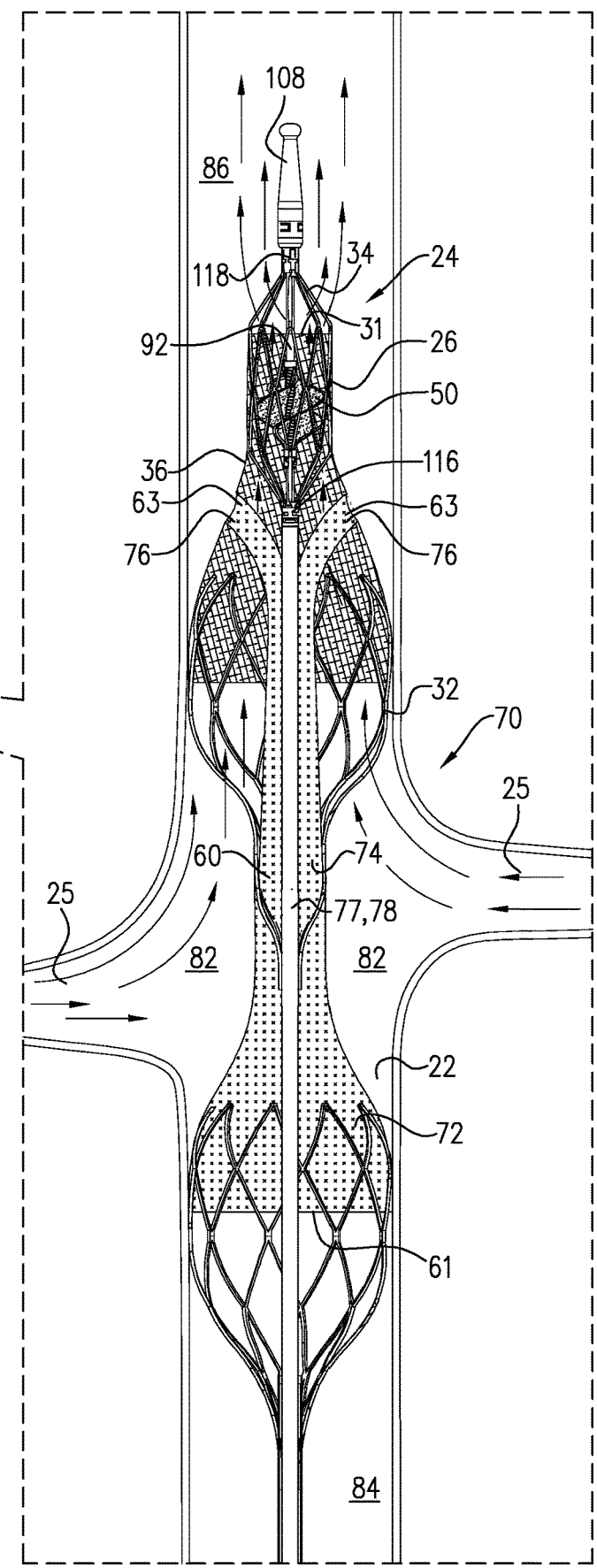
Figure 2C:
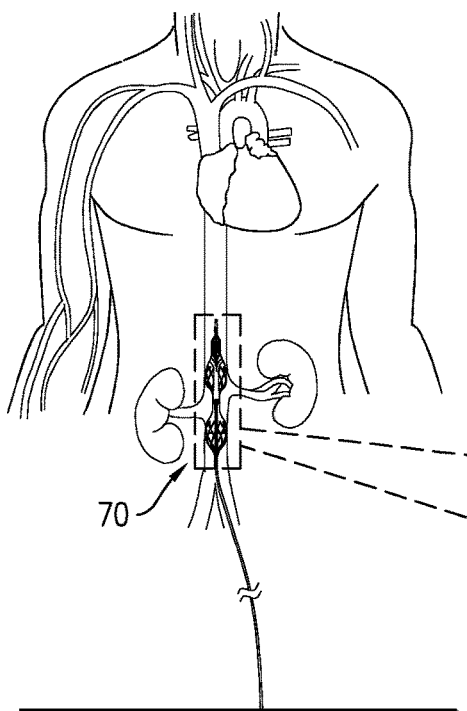
Figure 2C:
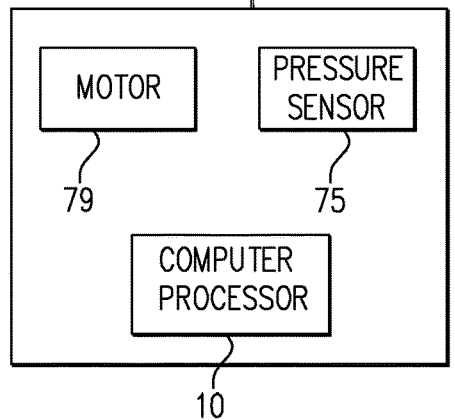
Figure 2C:
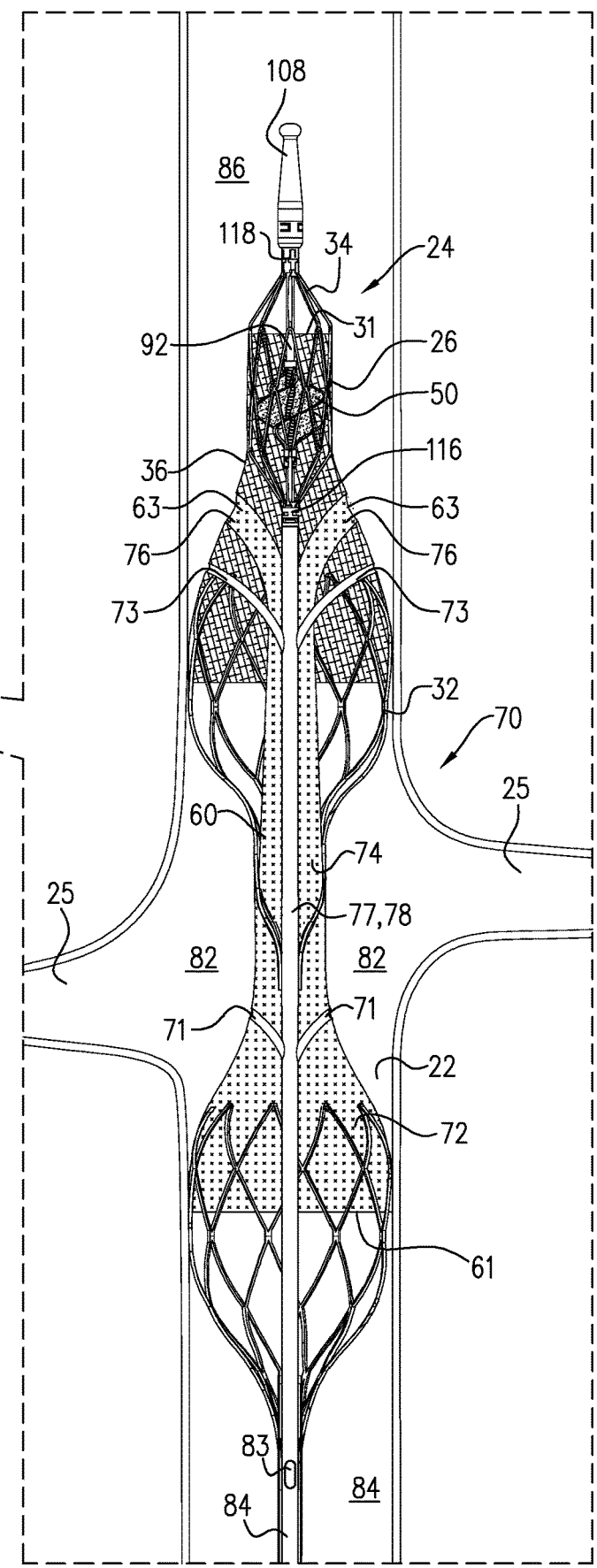

Reference is now made to FIGS. 2A and 2B, which are schematic illustrations of a blood-pump catheter 70 placed within a subject's vena cava 22, in accordance with some applications of the present invention. Typically, blood-pump catheter 70 includes blood pump 24, which typically includes impeller housing 26 and impeller 50, all of which are generally as described hereinabove. Impeller housing 26 (e.g., frame 34 of the housing) typically functions to separate the inner wall of the vena cava from the impeller (e.g., in case the vena cava collapses inwardly due to intra-abdominal pressure), such that the vena cava does not become injured by the impeller and the impeller does not become deformed by pressure from the inner wall of the vena cava. Further typically, an axial shaft 92 (shown in FIG. 7) that passes through the impeller is supported by radial bearings 116, 118 that are disposed, respectively, at proximal and distal end of the impeller housing.

For some such applications, a blood-pump-support frame 32 is disposed upstream of impeller housing 26, and is configured to come into contact with the inner wall of the vena cava. Blood-pump-support frame 32 is configured to align the longitudinal axis of impeller housing 26, and, in turn, impeller 50, with the local longitudinal axis of the vena cava, by contacting the inner wall of the vena cava. (It is noted that, for some applications, the blood-pump-support frame may not fully align the longitudinal axis of impeller with the local longitudinal axis of the vena cava. However, typically, the blood-pump-support frame maintains the longitudinal axis of the impeller in greater alignment with the local longitudinal axis of the vena cava, relative to alignment of the longitudinal axis of the impeller with the local longitudinal axis of the vena cava in the absence of the blood-pump-support frame.) Typically, ceteris paribus, the efficacy of the pumping of blood by impeller 50 is greater, the greater the alignment of the longitudinal axis of the impeller with the local longitudinal axis of the vena cava. As noted above, a slight misalignment of the of the longitudinal axis of the impeller with the local longitudinal axis of the vena cava (e.g., as shown in FIG. 2E), will nevertheless typically still result in efficacious pumping of blood by the impeller.

For some applications, impeller housing 26 includes a frame 34 (e.g., a rigid or semi-rigid frame) made of a shape-memory element (such as nitinol) that is at least partially covered with a material 36 (e.g., a blood-impermeable material, e.g., polyester, polyurethane, and/or a different polymer). Typically, for such applications, the stiffness of frame 34 is sufficiently great that pressure exerted upon the frame 34 by the inner wall of the vena cava does not deform the frame. Typically, material 36 extends from the impeller housing to blood-pump-support frame 32 such as to contact the vessel wall and to occlude the blood vessel in the region of the blood vessel that surrounds the impeller and/or that is upstream of the impeller. The material typically defines a hole therethrough at a distal portion of the impeller housing. The material is configured to occlude backflow of blood around the outside of the impeller, but such to allow antegrade blood flow in the central region of the vessel in the vicinity of the impeller, by the hole acting as a blood-outlet opening 31. For some applications, a portion of the impeller housing is covered (i.e., lined) on the inside of the impeller housing with an inner lining 39, e.g., as described hereinbelow with reference to FIG. 7. For some such applications, the inner lining of the impeller housing at least partially overlaps with material 36. For some applications, the inner lining extends the blood-outlet opening defined by material 36.

Typically, a drive cable 78 is disposed within an outer tube 77 of blood-pump catheter 70. (The drive cable is shown in FIG. 8A, for example.) Typically, the drive cable extends from motor 79 which is disposed outside the subject's body, to axial shaft 92 (shown in FIG. 7), upon which the impeller is disposed. The motor imparts rotational motion to the axial shaft (and thereby imparts rotational motion to the impeller), via the drive cable. Typically, the motor is controlled by computer processor 10. For some applications, the motor is controlled, based upon blood pressure measurements that are performed by pressure sensor 75.

For some applications, the blood-pump catheter further includes a funnel 72 that extends into a tube 74. The funnel is configured to be placed upstream of junctions of the vena cava with the subject's renal veins, and is configured to direct all blood flow from the infrarenal vena cava into tube 74. In turn, tube 74 directs the blood flow from the infrarenal location to a suprarenal location, in such a manner that this blood flows to the suprarenal location by bypassing blood pump 24 (i.e., without being pumped by blood pump 24). For example, tubes 76 may extend from tube 74 to a suprarenal location while bypassing the blood pump. As indicated by the blood flow arrows in FIG. 2A, blood thereby flows from the infrarenal vena cava to the suprarenal vena cava without being pumped by blood pump 24. By contrast, blood is pumped from a region of the vena cava that is adjacent to the junctions of the vena cava with the renal veins to the suprarenal vena cava, by blood pump 24, as indicated by the blood flow arrows in FIG. 2B.

In this manner, by deploying the blood-pump catheter 70 within the vena cava, the bloodstream of the region of the vena cava that is adjacent to the junctions of the vena cava with the renal veins is separated into a compartment 82 that is separate from the infrarenal vena-caval bloodstream 84 and the suprarenal vena-caval bloodstream 86. Blood flow from the infrarenal vena-caval bloodstream 84 to the suprarenal vena-caval bloodstream 86 occurs passively (e.g., by flowing through funnel 72, tube 74, and tubes 76). Blood is pumped actively from compartment 82 to the suprarenal bloodstream, using blood pump. In this manner, a region of low pressure within the vena cava is generated in compartment 82, within which the blood pressure is lower than the subject's central venous pressure. Typically, by generating a region of low pressure, blood flow from the renal veins into the vena cava increases, thereby lowering renal blood pressure and enhancing renal perfusion.

It is noted that the specific example of the construction of funnel 72, tube 74, and tube 76, is shown by way of example, and the scope of the present applications includes using any other construction of a blood-flow pathway 60 (i.e., blood-flow channel) to direct blood from the infrarenal vena cava to the suprarenal vena cava without being pumped by blood pump 24, mutatis mutandis. Typically, funnel 72, tube 74 and tubes 76 comprise respective portions of a single continuous blood-flow pathway. The blood-flow pathway typically passes between a pathway-inlet opening 61 disposed at an upstream location that is upstream of junctions of the vena cava with the renal veins and a pathway-outlet opening 63 that opens to a downstream side of material 36. Typically, funnel 72 defines a wide end 85 and a narrow end 87, as shown in FIG. 2A. The wide end of the funnel typically defines the inlet opening into the blood-flow pathway, and the narrow end of the funnel passes into one or more tubes (e.g., tubes 74 and 76).

Typically, blood flow from the infrarenal vena-caval bloodstream 84 to the suprarenal vena-caval bloodstream 86 is substantially unchanged relative to the blood flow from the infrarenal vena-caval bloodstream 84 to the suprarenal vena-caval bloodstream 86 in the absence of the blood-pump catheter. For some applications, the diameters of one or more portions of blood-flow pathway 60 are controlled such as to control blood flow from the infrarenal vena-caval bloodstream 84 to the suprarenal vena-caval bloodstream 86. For example, the diameters of one or more portions of the blood-flow pathway (e.g., funnel 72, tube 74, and/or tube(s) 76) may be modulated (e.g., using an inflatable/deflatable component that is disposed inside or outside one of these elements). In this manner, preload to the right atrium may be controlled, for example.

For some applications, blood flow from the infrarenal vena-caval bloodstream 84 to the suprarenal vena-caval bloodstream 86 is controlled responsively (e.g., automatically in response) to one or more pressure measurements, for example, pressure measurements that are performed as described herein. Alternatively or additionally, blood flow from the infrarenal vena-caval bloodstream 84 to the suprarenal vena-caval bloodstream 86 may be modulated periodically (e.g., in the above-described manner). For example, a healthcare professional (or another person) may periodically modulate blood flow from the infrarenal vena-caval bloodstream 84 to the suprarenal vena-caval bloodstream 86 (e.g., in the above-described manner), in response to changes in the subject's condition.

For some applications, the diameters of one more portions of blood-flow pathway 60 (e.g., funnel 72, tube 74, and tubes 76) are not modulable, but the diameter of at least a portion of the blood-flow pathway is such that blood flow from the infrarenal vena-caval bloodstream 84 to the suprarenal vena-caval bloodstream 86 is reduced (relative to the level of blood flow that would occur in the absence of these components), such as to reduce preload to the right atrium.

Reference is now made to FIG. 2C, which is a schematic illustration of blood-pump catheter 70, the blood-pump catheter including blood-pressure measurement tubes 71, 73, in accordance with some applications of the present invention. Reference is also again made to FIG. 1C, which shows blood-pump catheter 20 including blood-pressure measurement tubes 73, in accordance with some applications of the present invention.

For some applications, at least one blood-pressure-measurement tube 71 is configured to extend to at least an outer surface of funnel 72 and/or tube 74, such that an opening at the distal end of the blood-pressure-measurement tube is in direct fluid communication with the patient's bloodstream outside funnel 72 and/or tube 74 (i.e., the renal venous bloodstream). Pressure sensor 75 measures pressure of blood within the blood-pressure-measurement tube. Typically, by measuring pressure of blood within the blood-pressure-measurement tube, the pressure sensor thereby measures the subject's blood pressure outside funnel 72 and/or tube 74, which is indicative of the renal venous blood pressure. Typically, blood-pressure-measurement tube 71 extends from outside the subject's body to an opening at the distal end of the tube, and the pressure sensor is disposed toward a proximal end of the tube, e.g., outside the subject's body. For some applications, computer processor 10, receives an indication of the measured blood pressure and controls the pumping of blood by the impeller, in response to the measured blood pressure.

For some applications of blood-pump catheter 20, blood-pump catheter 70, or blood-pump catheter 90 (described hereinbelow), at least one blood-pressure-measurement tube 73 is configured to extend to at least an outer surface of material 36, such that an opening at the distal end of the blood-pressure-measurement tube is in direct fluid communication with the patient's bloodstream outside material 36 (e.g., the suprarenal vena-caval blood pressure). Pressure sensor 75 measures pressure of blood within the blood-pressure-measurement tube. Typically, by measuring pressure of blood within the blood-pressure-measurement tube, the pressure sensor thereby measures the subject's blood pressure outside material 36, which is indicative of the suprarenal vena-caval blood pressure, in the example shown in FIGS. 1C and 2C. Typically, blood-pressure-measurement tube 73 extends from outside the subject's body to an opening at the distal end of the tube, and the pressure sensor is disposed toward a proximal end of the tube, e.g., outside the subject's body. For some applications, computer processor 10, receives an indication of the measured blood pressure and controls the pumping of blood by the impeller, in response to the measured blood pressure. For some applications (e.g., when used in conjunction with blood-pump catheter 70), the computer processor modulates blood flow from the infrarenal vena-caval bloodstream 84 to the suprarenal vena-caval bloodstream 86 (e.g., as described hereinabove), in response to the measured blood pressure. For some applications (e.g., when used in conjunction with blood-pump catheter 20, as shown in FIGS. 1A and 1B), the computer processor modulates the diameter to which occlusion element 40 is expanded, in response to the measured blood pressure.

As described hereinabove, typically, a drive cable 78 is disposed within an outer tube 77 of blood-pump catheters 20, 70, and 90. (The drive cable is shown in FIG. 7A, for example.) Typically, the drive cable extends from motor 79 which is disposed outside the subject's body, to axial shaft 92, upon which the impeller is disposed. The motor imparts rotational motion to the axial shaft (and thereby imparts rotational motion to the impeller), via the drive cable. For some applications, the one or more blood-pressure measurement tubes 71, 73 are disposed within outer tube 77, surrounding the drive cable, along at least a portion of the lengths of the blood-pressure measurement tubes.

As shown in FIG. 1C and FIG. 2C, for some applications of blood-pump catheter 20 or blood-pump catheter 70, infrarenal vena-caval blood pressure is measured using at least one blood-pressure-measurement tube that defines an opening 83 in outer tube 77 at its distal end. The blood-pressure-measurement tube is configured to extend from outside the subject's body to an outer surface of outer tube 77 within the subject's infrarenal vena cava, such that the opening at the distal end of the blood-pressure-measurement tube is in direct fluid communication with the subject's infrarenal-vena-caval bloodstream. Pressure sensor 75 is configured to measure the subject's infrarenal vena-caval blood pressure by measuring blood pressure within the blood-pressure-measurement tube. For some applications (e.g., when used with blood-pump catheter 20 as shown in FIGS. 1A-1C), renal venous pressure is measured in a generally similar manner (e.g., via a blood-pressure-measurement tube that defines an opening that is disposed in a vicinity of junctions of the renal veins with the vena cava). For some applications, computer processor 10, receives an indication of the measured blood pressure and controls the pumping of blood by the impeller, in response to the measured blood pressure. For some applications (e.g., when used in conjunction with blood-pump catheter 70), the computer processor modulates blood flow from the infrarenal vena-caval bloodstream 84 to the suprarenal vena-caval bloodstream 86 (e.g., as described hereinabove), in response to the measured blood pressure. For some applications (e.g., when used in conjunction with blood-pump catheter 20, as shown in FIGS. 1A and 1B), the computer processor modulates the diameter to which occlusion element 40 is expanded, in response to the measured blood pressure.

It is typically the case that there is a relationship between the amount of power that is required to power the rotation of the impeller at a given rotation rate and the pressure difference that the impeller generates. (Typically, the impeller lowers the pressure in the region of the vena cava that is upstream of material 36, by pumping blood to the region of the vena cava that is downstream of material 36, thereby lowering the blood pressure in the upstream region and generating a pressure difference between the upstream region and the downstream region.) For some applications, calibration measurements are performed, such that the relationship between (a) power consumption by the motor that is required to rotate the impeller at a given rotation rate and (b) the pressure difference that is generated by the impeller, is known.

For some applications, blood pressure upstream of impeller 50 and covering material 36 is measured, for example, using the blood-pressure-measurement tube that defines opening 83 in outer tube 77 at its distal end, and/or using a pressure sensor that is disposed within the vena cava at an infrarenal location (e.g., a piezo-electric pressure sensor, and/or an optical sensor). For some such applications, blood pressure downstream of impeller 50 and covering material 36 is then calculated by the computer processor, based upon (a) the measured upstream blood pressure, (b) the power consumption by the motor that is required to rotate the impeller at a given rotation rate at that time, and (c) the predetermined relationship between power consumption by the motor that is required to rotate the impeller at a given rotation rate and the pressure difference that is generated by the impeller. For some applications, the above-described technique is performed while maintaining the rotation rate of the impeller at a constant rate. Alternatively or additionally, the rotation rate of the impeller is varied, and the variation of the rotation rate of the impeller is accounted for in the above-described calculations.

Typically, blood-outlet opening 31 in material 36 has a known cross-sectional area. For some applications, the flow through the blood-outlet opening that is generated by the impeller is determined based on the determined pressure difference that is generated by the impeller, and the known cross-sectional area of the opening. For some applications, such flow calculations incorporate calibration parameters in order to account for factors such as flow resistance that are specific to the blood-pump catheter (or type of blood-pump catheter) upon which the calculations are performed.

For some applications, the above-described apparatus and methods for measuring blood pressure are used in conjunction with blood-pump catheter 20 described hereinabove with reference to FIGS. 1A-C, in conjunction with blood-pump catheter 70 described hereinabove with reference to FIGS. 2A-F, in conjunction with blood-pump catheter 90 described hereinbelow with reference to FIGS. 3A-B, and/or in conjunction with blood-pump catheter 20 described hereinbelow with reference to FIGS. 4A-B, mutatis mutandis.

Figure 2D:
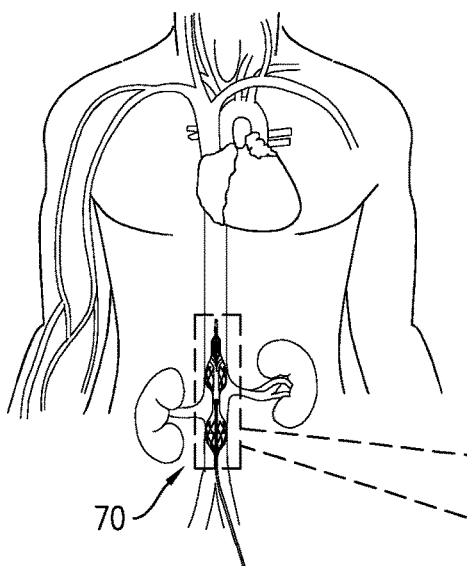
FIG. 2D is a schematic illustration of a blood-pump catheter placed within a subject's vena cava, the blood pump having a non-axisymmetric outflow tube, in accordance with some applications of the present invention.
Figure 2D:
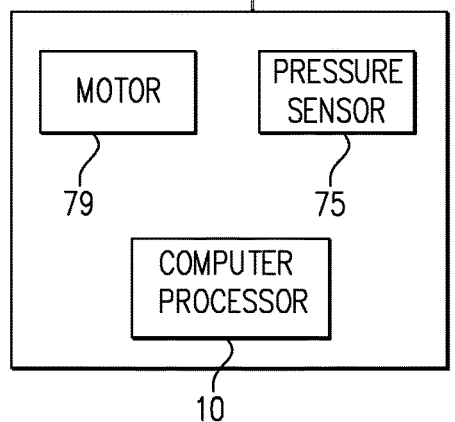
Figure 2D:
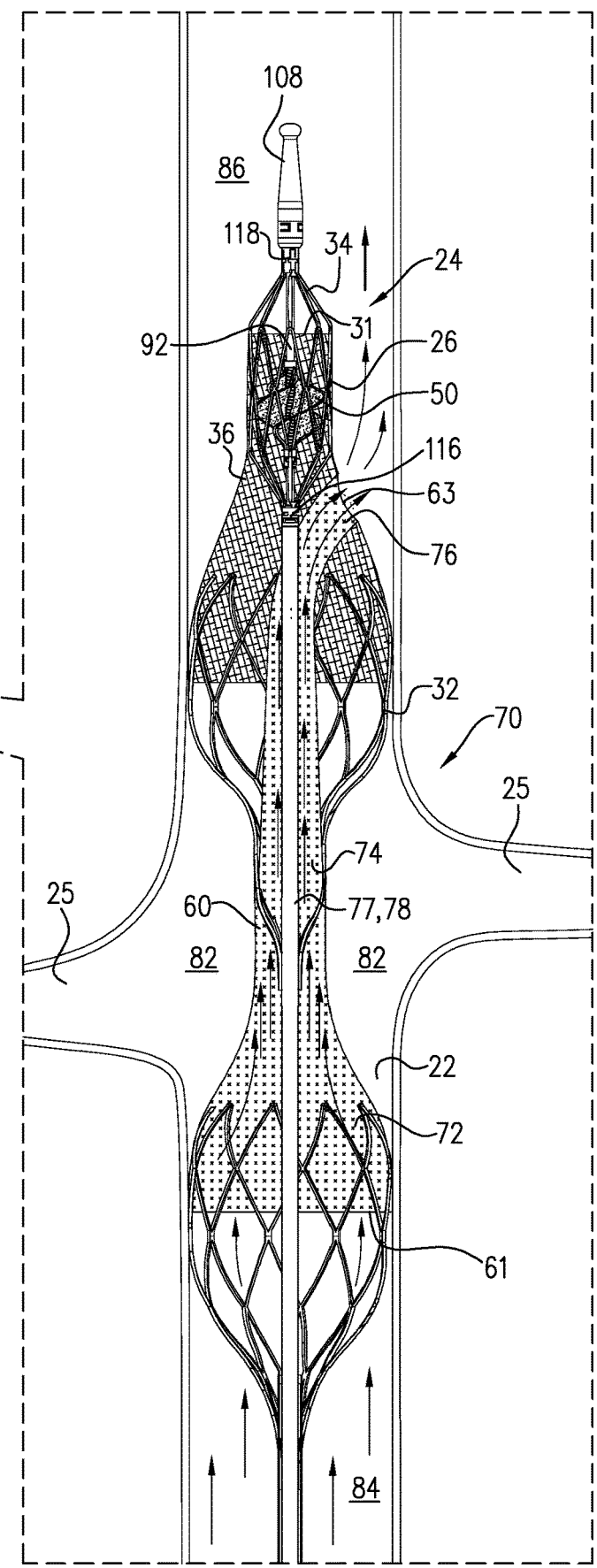
Figure 2E:
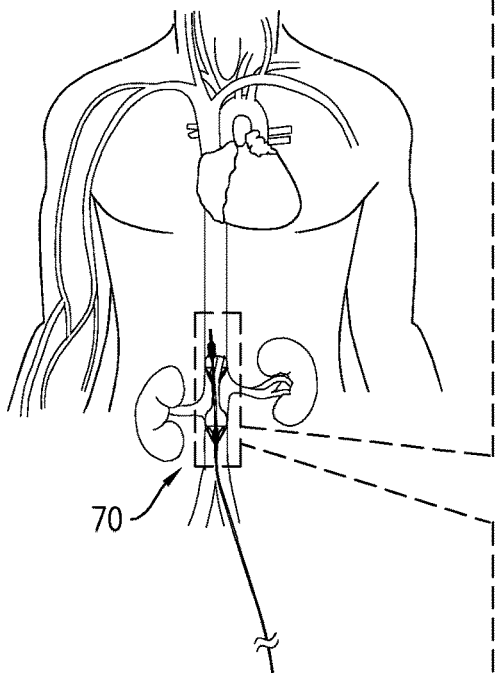
FIG. 2E is a schematic illustration of a blood-pump catheter placed within a subject's vena cava, the blood pump having a non-axisymmetric outflow tube and a non-axisymmetric impeller, in accordance with some applications of the present invention.
Figure 2E:
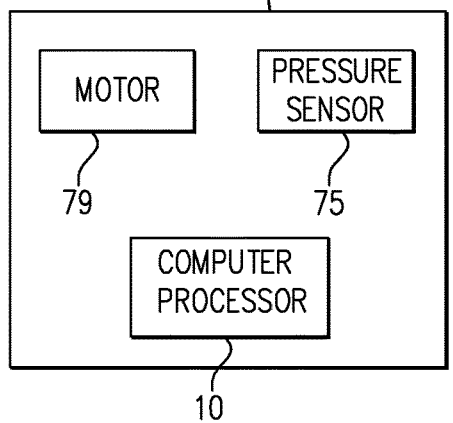
Figure 2E:
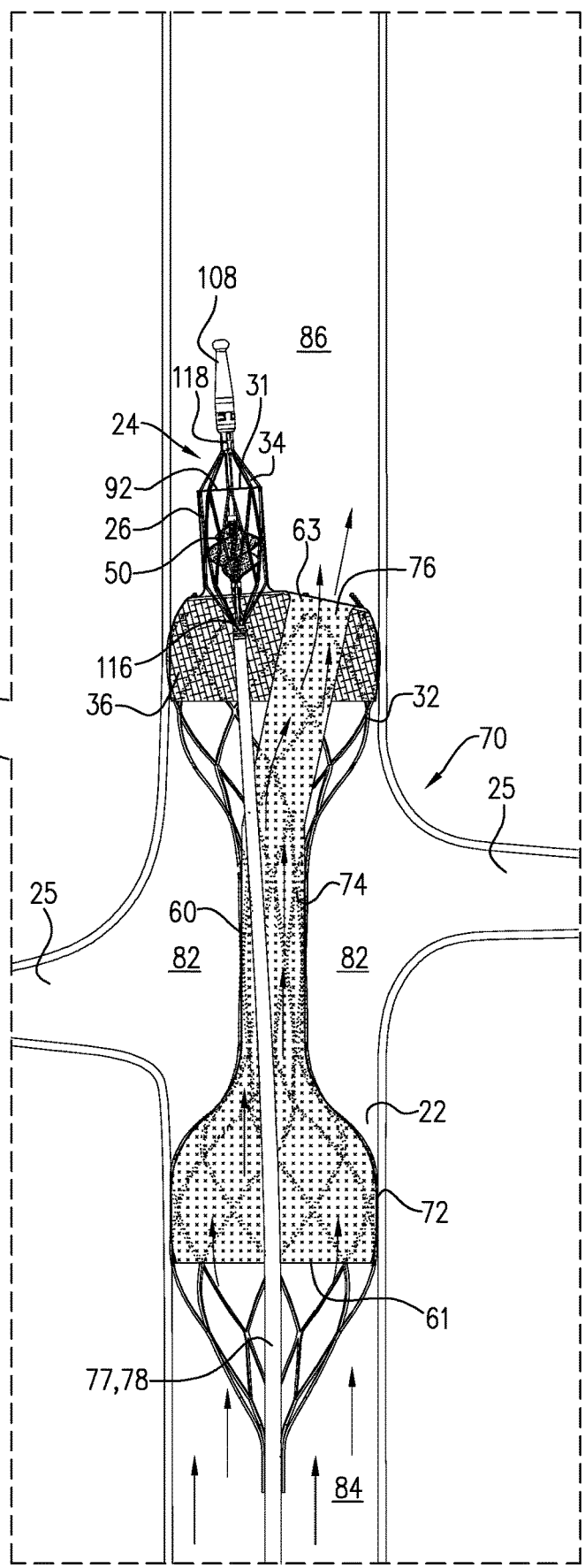

Reference is now made to FIG. 2D, which is a schematic illustration of blood-pump catheter 70 placed within the subject's vena cava 22, the blood pump having a non-axisymmetric outflow tube 76, in accordance with some applications of the present invention. Blood-pump catheter 70 as shown in FIG. 2D is generally similar to that shown and described with reference to FIGS. 2A-C. However, in the example shown in FIGS. 2A-C, the blood-pump catheter included two tubes 76 disposed on respective sides of the longitudinal axis of the blood-pump catheter, and extending from tube 74 to a suprarenal location, while bypassing blood pump 24. By contrast, in the example shown in FIG. 2D, the blood-pump catheter includes only a single tube 76 disposed on one side of the longitudinal axis of the blood-pump catheter, and extending from tube 74 to a suprarenal location, while bypassing blood pump 24, in accordance with some applications of the present invention. In other respects, blood-pump catheter 70 as shown in FIG. 2D is generally similar to that shown in and described with reference to FIGS. 2A-C. For some applications (not shown), blood-pump catheter includes more than two tubes 76 disposed at respective locations around the longitudinal axis of the blood-pump catheter, and extending from tube 74 to a suprarenal location, while bypassing blood pump 24.

Figure 2F:
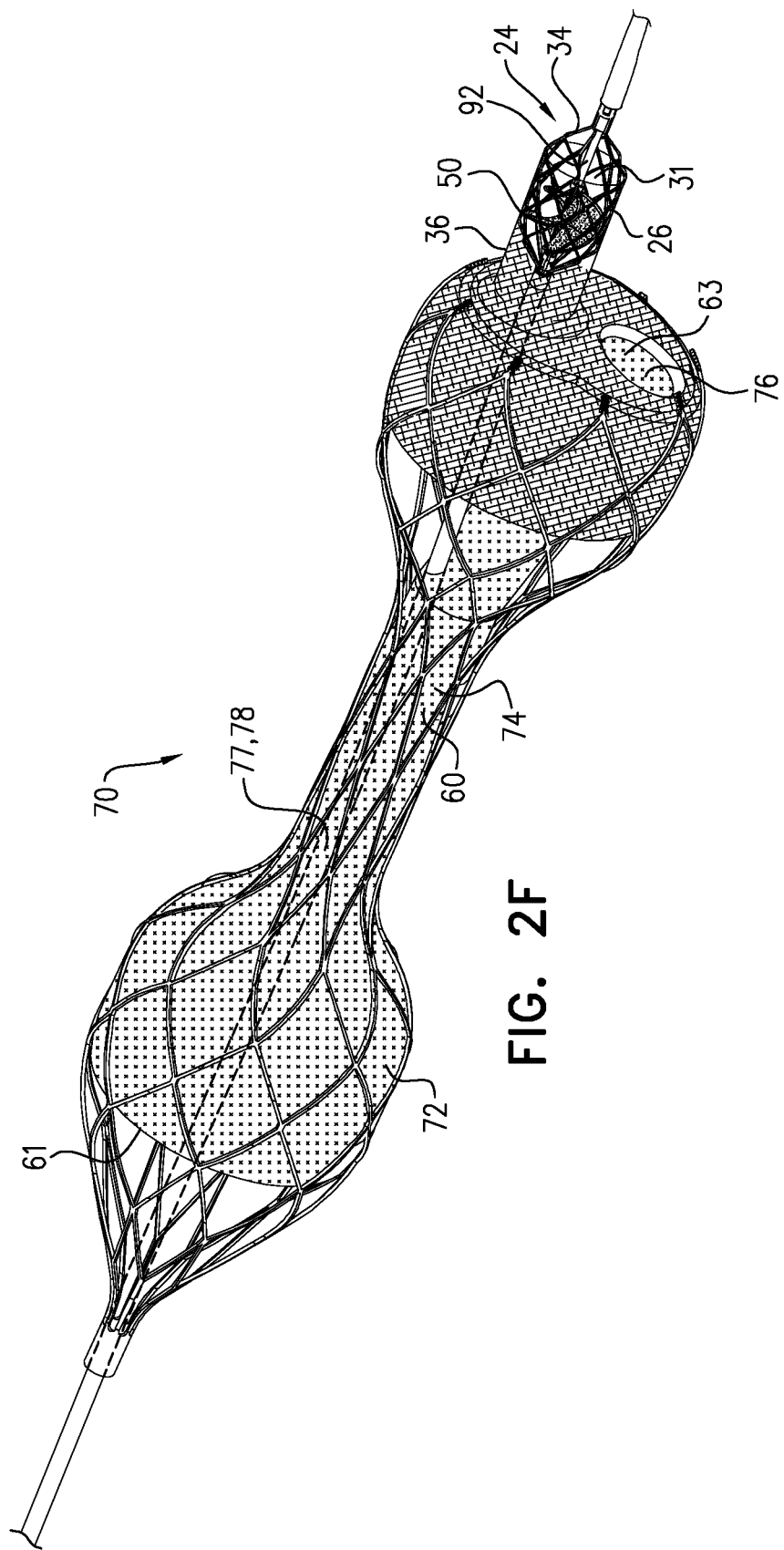
FIG. 2F is a schematic illustration of the blood-pump catheter of FIG. 2E in the absence of the subject's anatomy, in accordance with some applications of the present invention.

Reference is now made to FIG. 2E, which is a schematic illustration of blood-pump catheter 70 placed within the subject's vena cava 22, the blood pump having a non-axisymmetric outflow tube 76 and a non-axisymmetric blood pump 24, in accordance with some applications of the present invention. Reference is also made to FIG. 2F, which is a schematic illustration of the blood-pump catheter of FIG. 2E in the absence of the subject's anatomy, in accordance with some applications of the present invention. As described hereinabove with reference to FIG. 2D, for some applications, the blood-pump catheter includes only a single tube 76 disposed on one side of the longitudinal axis of the blood-pump catheter, and extending from tube 74 to a suprarenal location, while bypassing blood pump 24. For some such applications, blood pump 24 is disposed in a non-axisymmetric orientation on the opposite side of the longitudinal axis of the blood-pump catheter, as shown. In other respects, blood-pump catheter 70 as shown in FIGS. 2E and 2F is generally similar to that shown in and described with reference to FIGS. 2A-D.

For some applications, techniques as described with reference to FIGS. 2A-E are performed in the absence of blood pump 24. That is, the bloodstream within a region of the vena cava that is adjacent to junctions of the vena cava with the renal veins is separated into a compartment 82 that is separate from the infrarenal vena-caval bloodstream 84 and the suprarenal vena-caval bloodstream 86, in the absence of blood pump 24. For some such applications, blood flow from the infrarenal vena-caval bloodstream 84 to the suprarenal vena-caval bloodstream 86 is then controlled passively (e.g., as described hereinabove), without affecting blood flow from the renal veins to the suprarenal vena-caval bloodstream 86. Alternatively or additionally, blood flow from the renal veins to the suprarenal vena-caval bloodstream 86 is controlled passively, without affecting blood flow from the infrarenal vena-caval bloodstream 84 to the suprarenal vena-caval bloodstream 86.

With reference to FIGS. 2A-E, it is noted that the scope of the present invention includes applying similar apparatus and methods to any venous system of a subject that includes tributary veins that flow into a main vein. For example, similar techniques could be applied at junctions of the hepatic veins and the vena cava. Typically, such methods include separating bloodstream within the region of the main vein that is adjacent to junctions of the main vein with the tributary veins from bloodstream within the main vein upstream and downstream thereto, pumping blood from the region of the main vein that is adjacent to junctions of the vein with the tributary veins to a location within the main vein that is downstream of the tributary veins, using a pump, and allowing the subject's blood to flow from a location within the main vein that is upstream of the tributary veins to the location within the main vein that is downstream of the tributary veins without being pumped by the pump, by directing the blood to bypass the pump. For some applications, generally similar apparatus and methods are used within the subclavian vein or jugular vein, at junctions of the vein with a lymph duct. For some such applications, blood-pump catheter 70 is configured to increase flow of lymphatic fluid from the lymph duct into the vein, mutatis mutandis. In general, the scope of some applications of the present invention further includes apparatus and methods for use with a venous system of a subject that includes tributary vessels (e.g., lymphatic vessels) that flow into a vein. Typically, such methods include separating flow within a region of the vein that is adjacent to junctions of the vein with the tributary vessels from bloodstream within the vein upstream and downstream thereto, pumping blood from the region of the vein that is adjacent to junctions of the vein with the tributary vessels to a location within the vein that is downstream of the region, using a pump, and allowing the subject's blood to flow from a location within the vein that is upstream of the tributary vessels to the location within the vein that is downstream of the tributary vessels without being pumped by the pump, by directing the blood to bypass the pump.

For some applications, such methods include at least partially occluding blood flow through a vein by placing a downstream occluding element (such as material 36) at a downstream location that is downstream of junctions of the vein with tributary vessels, pumping blood from the region of the vein that is adjacent to junctions of the vein with the tributary vessels and through the downstream occluding element, using a pump, directing upstream venous blood flow from an upstream location that is upstream of junctions of the vein with the tributary vessels to downstream of the occluding element, without the upstream venous blood flow being pumped by the pump, by directing the upstream venous blood flow to bypass the pump. Typically, such methods are performed using a blood-pump catheter (such as, blood-pump catheter 70), which includes material 36, which is configured to be placed at a downstream location that is downstream of junctions of the vein with the tributary vessel and to at least partially occlude blood flow through the vein at the downstream location, the material defining blood-outlet opening 31. Blood pump 24 is typically configured to pump blood from the region of the vein that is adjacent to junctions of the vein with the tributary vessels through the blood-outlet opening defined by the material. Blood-flow pathway 60 typically passes between a pathway-inlet opening 61 disposed at an upstream location that is upstream of junctions of the vein with the tributary vessels and a pathway-outlet opening 63 that opens to a downstream side of material 36. For some applications, the blood-flow pathway comprises funnel 72 and one or more tubes (e.g., tubes 74 and 76). Funnel 72 is configured to be disposed at an upstream location that is upstream of junctions of the vein with the tributary vessel, and one or more tubes 74, 76 are configured to extend from the funnel to a downstream side of the material. The funnel and the one or more tubes (or alternative blood-flow pathway) are configured to direct upstream venous blood flow from the upstream location to downstream of the material, without the upstream venous blood flow being pumped by the pump. Typically, funnel 72 defines a wide end 85 and a narrow end 87, as shown in FIG. 2A. The wide end of the funnel typically defines the inlet opening into the blood-flow pathway, and the narrow end of the funnel passes into one or more tubes (e.g., tubes 74 and 76).

Reference is now made to FIGS. 3A, 3B, 3C, 3D, 3E, 3F, 3G, and 3H, which are schematic illustrations of blood-pump catheter 70, in accordance with some further applications of the present invention. Blood-pump catheter 70 as shown and described with reference to FIGS. 3A-H is generally similar to that described with reference to FIGS. 2A-F, except for the differences described hereinbelow. It is noted that, as shown in FIGS. 3A-H, the blood-pump catheter has a generally similar design to that shown in FIGS. 2E and 2F (in that (a) only a single tube 76 is disposed on one side of the longitudinal axis of the blood-pump catheter, and extends from tube 74 to a suprarenal location, while bypassing blood pump 24, and (b) blood pump 24 is disposed in a non-axisymmetric orientation on the opposite side of the longitudinal axis of the blood-pump catheter). However, the scope of the present application includes combining features of blood-pump catheter 70 described with reference to FIGS. 3A-H with any one of the designs of blood-pump catheter 70 described hereinabove with reference to FIGS. 2A-D, mutatis mutandis.

Figure 3A:
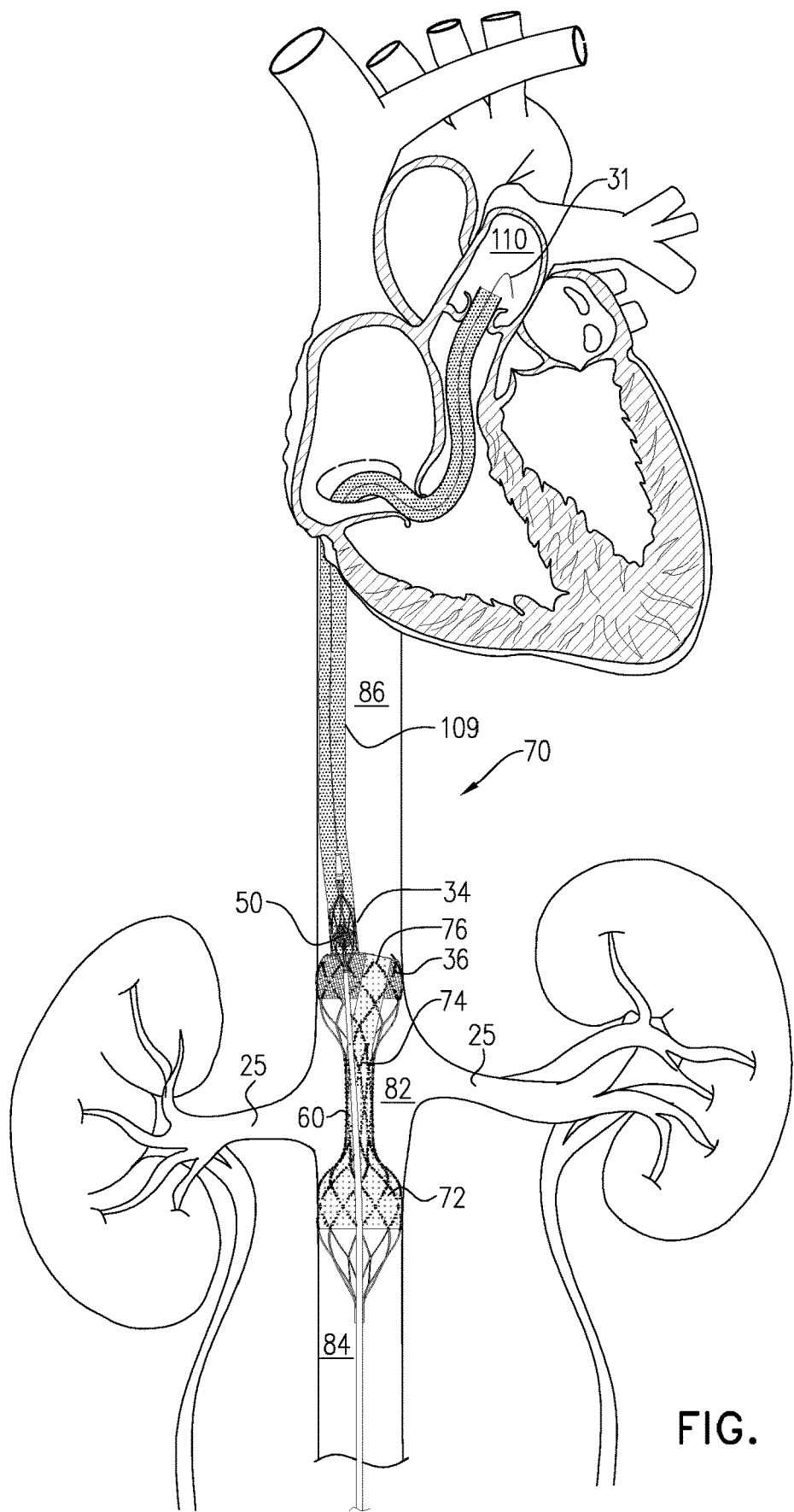
FIGS. 3A, 3B, 3C, 3D, 3E, 3F, 3G, and 3H are schematic illustrations of a blood-pump catheter, in accordance with some further applications of the present invention.

Referring now to FIG. 3A, for some applications, an elongate tube 109 extends from frame 34 to the subject's pulmonary artery 110, such that blood-outlet opening 31 is disposed in the pulmonary artery. (It is noted that, for some applications, material 36 defines a blood-outlet opening, and elongate tube extends from the blood-outlet opening defined by the material to the blood-outlet opening disposed within the pulmonary artery.) Tube 109 is typically made of a blood-impermeable material. For example, tube 109 may include polyurethane, polyester, and/or silicone. Alternatively or additionally, the tube is made of polyethylene terephthalate (PET) and/or polyether block amide (e.g., PEBAX®). Blood-pump catheter is configured to pump blood directly from compartment 82 into the subject's pulmonary artery. In this manner, the blood-pump catheter reduces renal venous pressure without increasing preload on the subject's right atrium. In accordance with the description of FIGS. 2A-F, typically, blood flow from the infrarenal vena-caval bloodstream 84 to the suprarenal vena-caval bloodstream 86 bypasses the elongate tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3B:
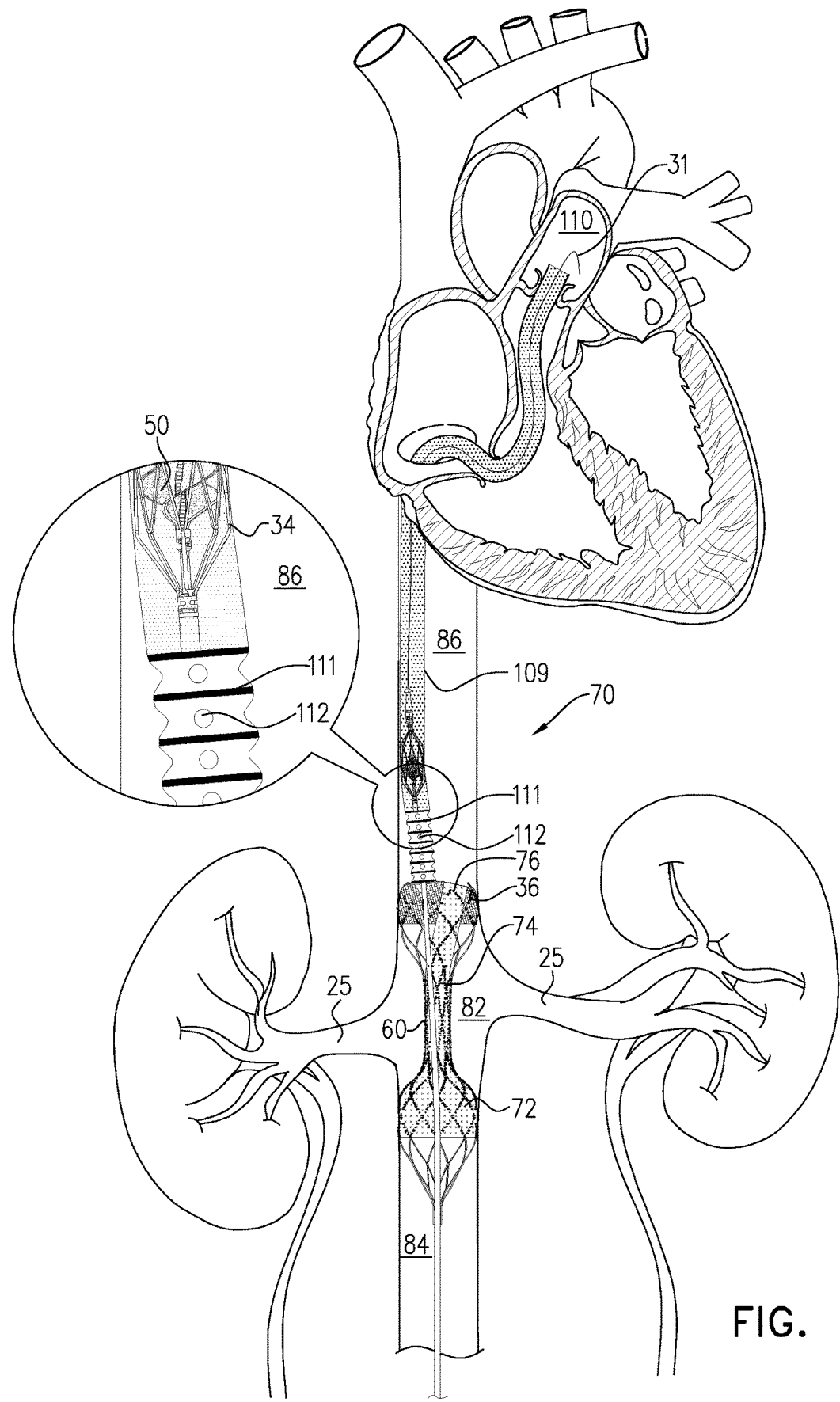

Referring to FIG. 3B, for some applications, elongate tube 109 includes a portion 111 that is disposed within suprarenal vena-caval bloodstream 86 and that defines suprarenal blood-inlet openings 112. Impeller 50 and frame 34 are typically disposed downstream of the suprarenal blood-inlet openings, and in addition to pumping blood into elongate tube 109 from compartment 82, the impeller is configured to pump blood into elongate tube 109 from the suprarenal vena-caval bloodstream, via blood-inlet openings 112. As described with reference to FIG. 3A, typically, elongate tube 109 extends from frame 34 to the subject's pulmonary artery 110, such that blood-outlet opening 31 is disposed in the pulmonary artery. Blood-pump catheter 70 as configured in FIG. 3B is typically configured to reduce renal venous pressure (by pumping blood from the compartment 82) and to assist with the subject's right heart function, by pumping blood from the suprarenal vena-caval bloodstream to the pulmonary artery. In accordance with the description of FIGS. 2A-F, typically, blood flow from the infrarenal vena-caval bloodstream 84 to the suprarenal vena-caval bloodstream 86 bypasses the elongate tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3C:
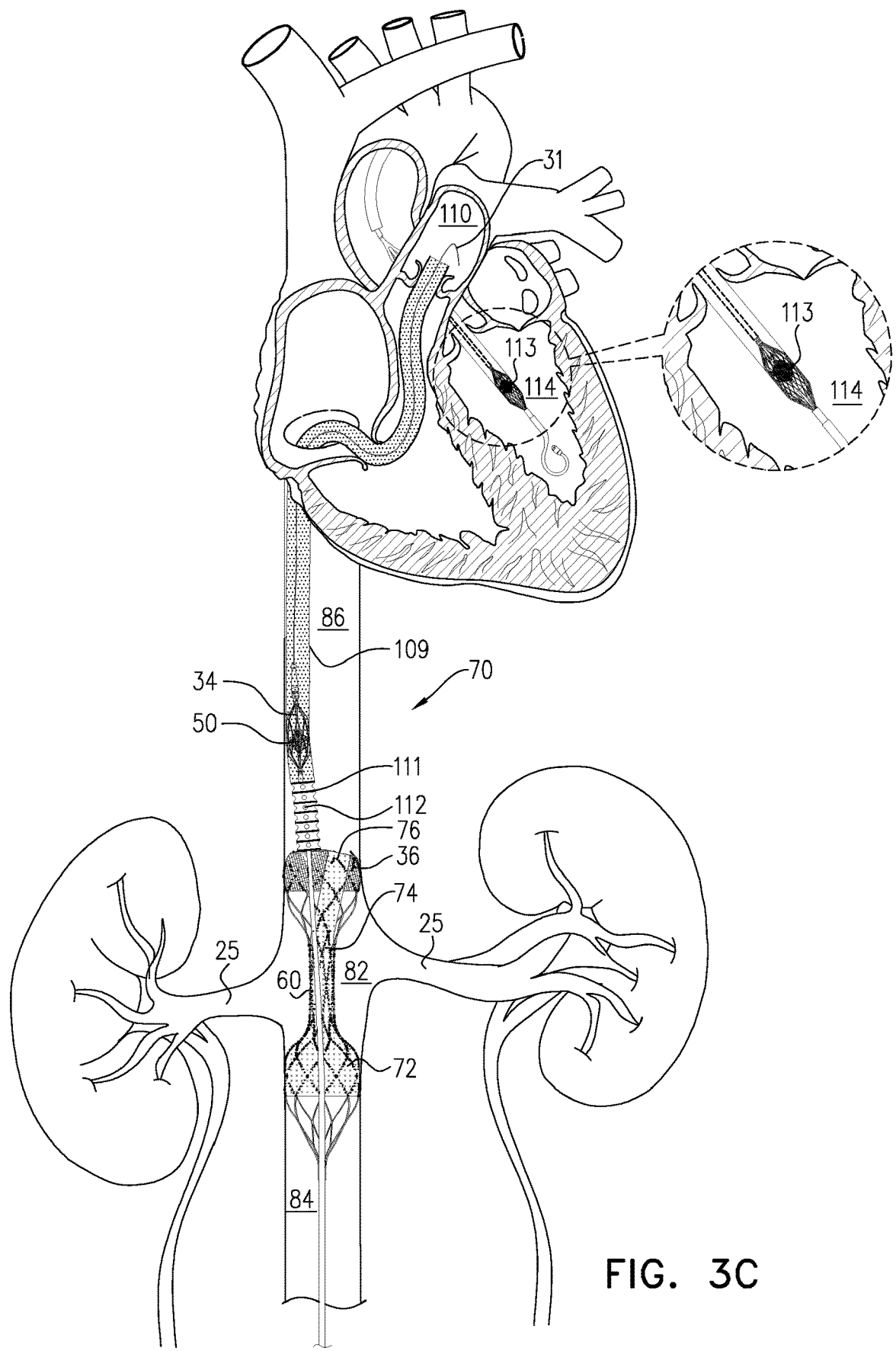

Referring to FIG. 3C, for some applications, in addition to using blood-pump catheter 70 to reduce renal venous pressure (and, optionally, to assist with right heart function, as described with reference to FIG. 3B), a left-ventricular assist device 113 is deployed within the subject's left ventricle 114, in order to assist with the subject's left heart function. For some applications, the left-ventricular assist device is a left-ventricular assist device as described in U.S. Ser. No. 16/750,354 to Tuval (filed Jan. 23, 2020, entitled "Distal tip element for a ventricular assist device"), US 2019/0209758 to Tuval, and/or US 2019/0175806 to Tuval, all of which applications are incorporated herein by reference. For some applications, the left-ventricular assist device includes a left-ventricular assist device manufactured by Abiomed® (Massachusetts, USA), such as Impella 2.5®, Impella CP®, Impella 5.5®, and/or Impella 5.0®. It is noted that although left-ventricular assist device 113 is shown as being used in combination with the example of blood-pump catheter 70 shown in FIG. 3B, the scope of the present application includes using left-ventricular assist device 113 in combination with any of the examples of blood-pump catheter 70 described herein.

Figure 3D:
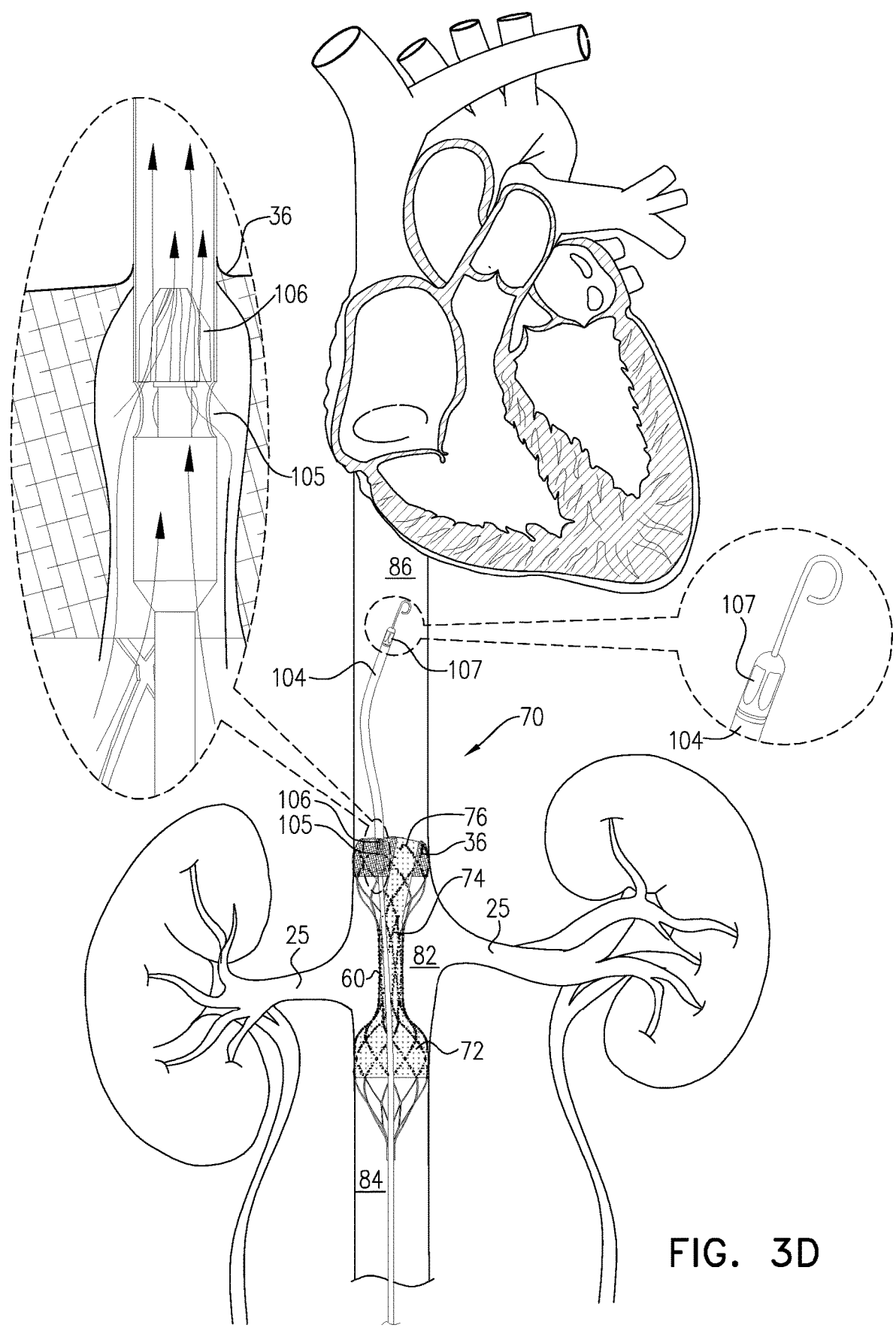

Referring now to FIG. 3D, for some applications, in place of impeller 50 and frame 34, an elongate blood-pump tube 104 (which typically includes an impeller), is disposed within the blood-outlet opening in covering material 36. Typically, covering material 36 and/or inner lining 39 (FIG. 7) is sealingly coupled to the outer surface of the elongate blood-pump tube. For example, the elongate blood-pump tube may include an Impella RP®, manufactured by Abiomed® (Massachusetts, USA). Typically, the elongate blood-pump tube includes a blood-inlet area 105 (disposed within an upstream portion of the elongate blood-pump tube), which is disposed at an inferior (i.e., upstream) position with respect to covering material 36 and/or inner lining 39 (FIG. 7). An impeller 106 (which is typically disposed distally and in close proximity to the blood-inlet area) pumps blood from compartment 82 into the blood-inlet area, through the elongate blood-pump tube, and out of a blood-outlet area 107 (disposed within a downstream portion of the elongate blood-pump tube). In the example shown in FIG. 3A, the blood-outlet area is disposed in the suprarenal vena cava, such that blood is pumped into suprarenal vena-caval bloodstream 86. In accordance with the description of FIGS. 2A-F, typically, blood flow from the infrarenal vena-caval bloodstream 84 to the suprarenal vena-caval bloodstream 86 bypasses the elongate blood-pump tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3E:
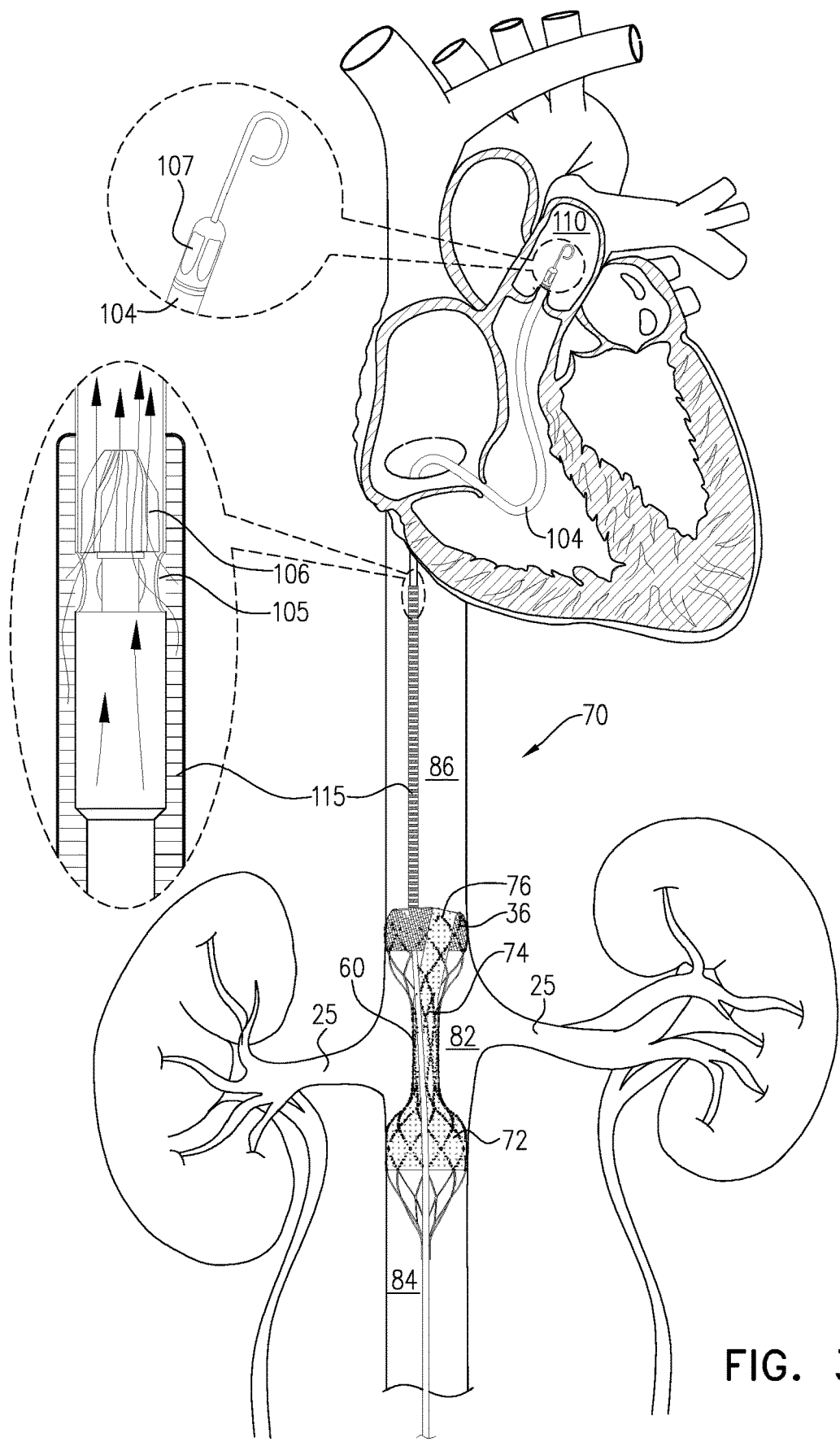

Referring to FIG. 3E, for some applications, elongate blood-pump tube 104 is disposed such that the blood-inlet area 105 and impeller 106 are disposed within the suprarenal vena cava. For some such applications, a reinforced tube 115 (e.g., a tube made of a polymer supported by a shape-memory-material (e.g., nitinol) frame and/or a shape-memory-material (e.g., nitinol) braid) extends from the outlet opening of covering material 36 and/or inner lining 39 (FIG. 7) to the blood-inlet area of the elongate blood-pump tube, and forms a seal between covering material 36 and/or inner lining 39 and the blood-inlet area of the elongate blood-pump tube. In this manner, impeller 106 draws blood from compartment 82 into blood-inlet area 105. Typically, the elongate blood-pump tube extends from the blood-inlet area to blood-outlet area 107, which is disposed in the subject's pulmonary artery 110. In some alternative applications (not shown), the elongate blood-pump tube itself extends from upstream of covering material 36 until pulmonary artery 110 (i.e., in the absence of reinforced tube 115). Elongate blood-pump tube is configured to pump blood from compartment 82 into the subject's pulmonary artery. In this manner, blood-pump catheter 70 reduces renal venous pressure without increasing preload on the subject's right atrium. In accordance with the description of FIGS. 2A-F, typically, blood flow from the infrarenal vena-caval bloodstream 84 to the suprarenal vena-caval bloodstream 86 bypasses the elongate blood-pump tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3F:
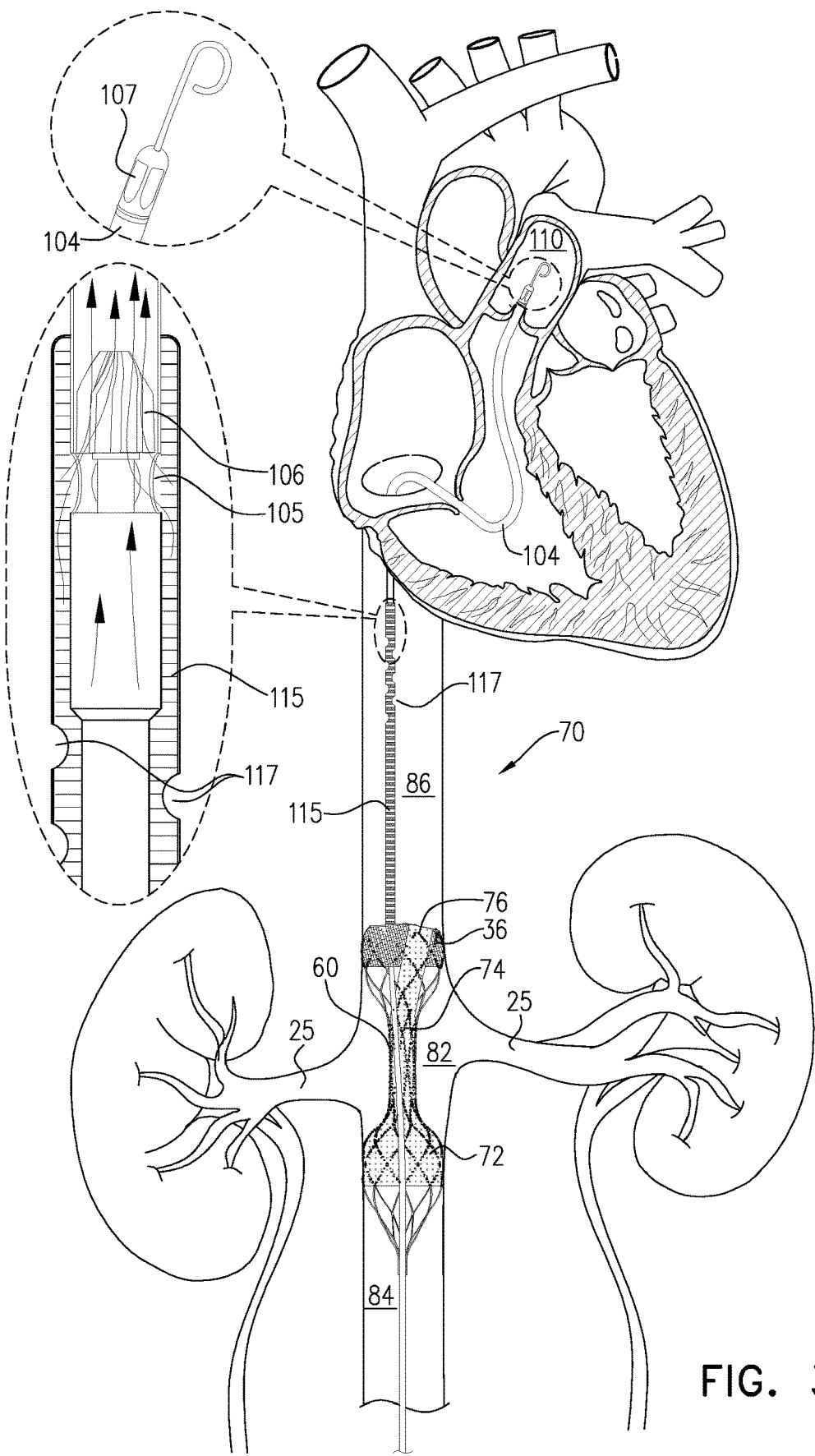

Referring now to FIG. 3F, for some applications, reinforced tube 115 defines blood-inlet openings 117, which are disposed in the suprarenal vena cava. Impeller 106 and blood-inlet area 105 are typically disposed downstream of blood-inlet openings 117, and in addition to pumping blood into elongate blood-pump tube 104, the impeller is configured to pump blood into elongate blood-pump tube 104 from the suprarenal vena-caval bloodstream, via blood-inlet openings 117. As described with reference to FIG. 3E, typically, elongate blood-pump tube 104 extends from the suprarenal vena cava to the subject's pulmonary artery 110, such that blood-outlet area 107 is disposed in the pulmonary artery. Blood-pump catheter 70 as configured in FIG. 3F is typically configured to reduce renal venous pressure (by pumping blood from the compartment 82) and to assist with the subject's right heart function, by pumping blood from the suprarenal vena-caval bloodstream to the pulmonary artery. In accordance with the description of FIGS. 2A-F, typically, blood flow from the infrarenal vena-caval bloodstream 84 to the suprarenal vena-caval bloodstream 86 bypasses the elongate blood-pump tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3G:
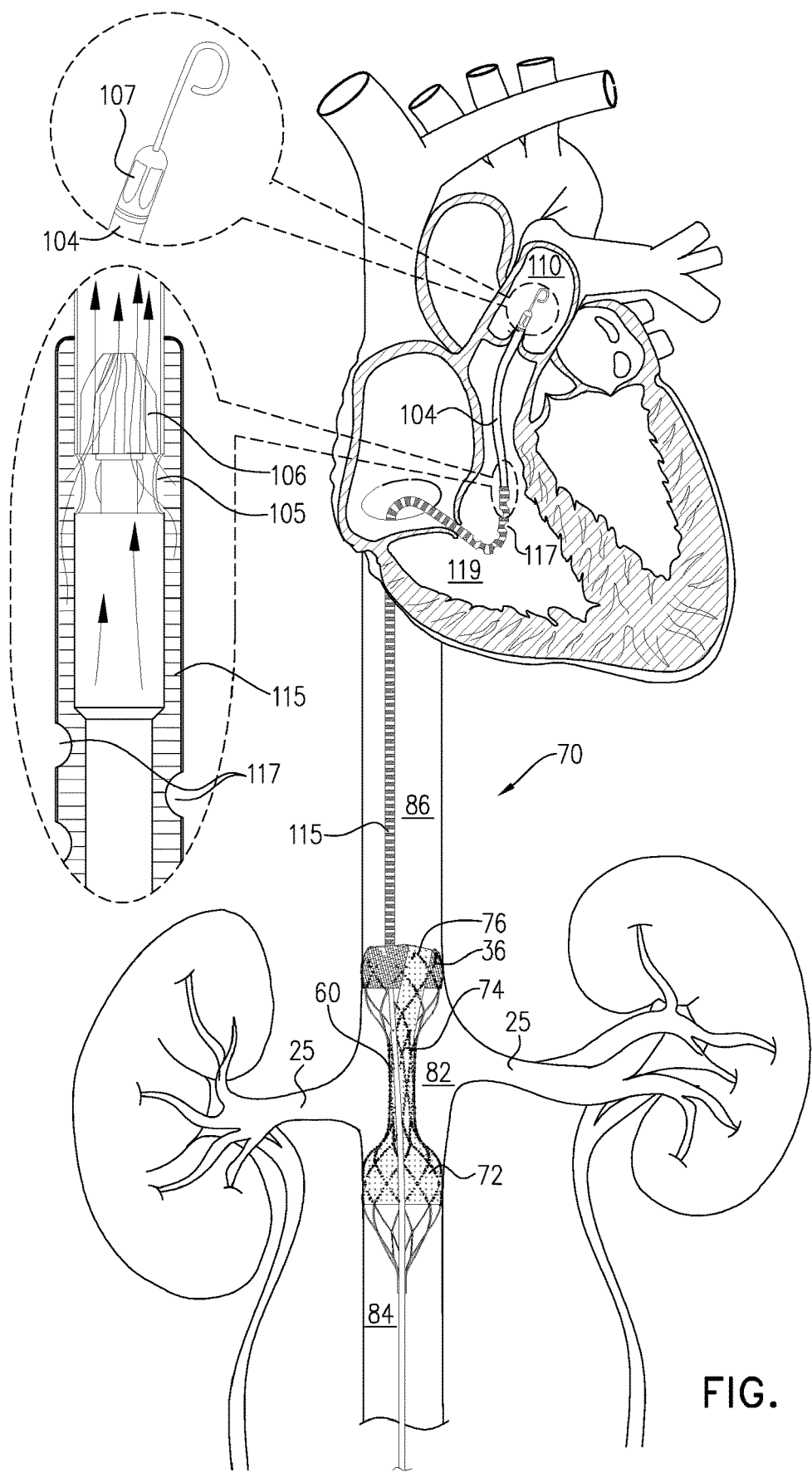

Referring now to FIG. 3G, for some applications, blood-inlet openings 117 are disposed in the subject's right ventricle 119, and impeller 106 and blood-inlet area 105 are disposed downstream of the blood-inlet openings. In addition to pumping blood into elongate blood-pump tube 104, the impeller is configured to pump blood into elongate blood-pump tube 104 from the right ventricle, via blood-inlet openings 117. Typically, elongate blood-pump tube 104 extends from the right ventricle to the subject's pulmonary artery 110, such that blood-outlet area 107 is disposed in the pulmonary artery. Blood-pump catheter 70 as configured in FIG. 3G is typically configured to reduce renal venous pressure (by pumping blood from the compartment 82) and to assist with the subject's right heart function, by pumping blood from the right ventricle to the pulmonary artery. In accordance with the description of FIGS. 2A-F, typically, blood flow from the infrarenal vena-caval bloodstream 84 to the suprarenal vena-caval bloodstream 86 bypasses the elongate blood-pump tube. Typically, blood flow from the infrarenal vena-caval bloodstream 84 to the suprarenal vena-caval bloodstream 86 occurs passively, by flowing through blood-flow pathway 60 (e.g., funnel 72, tube 74, and tube(s) 76).

Figure 3H:
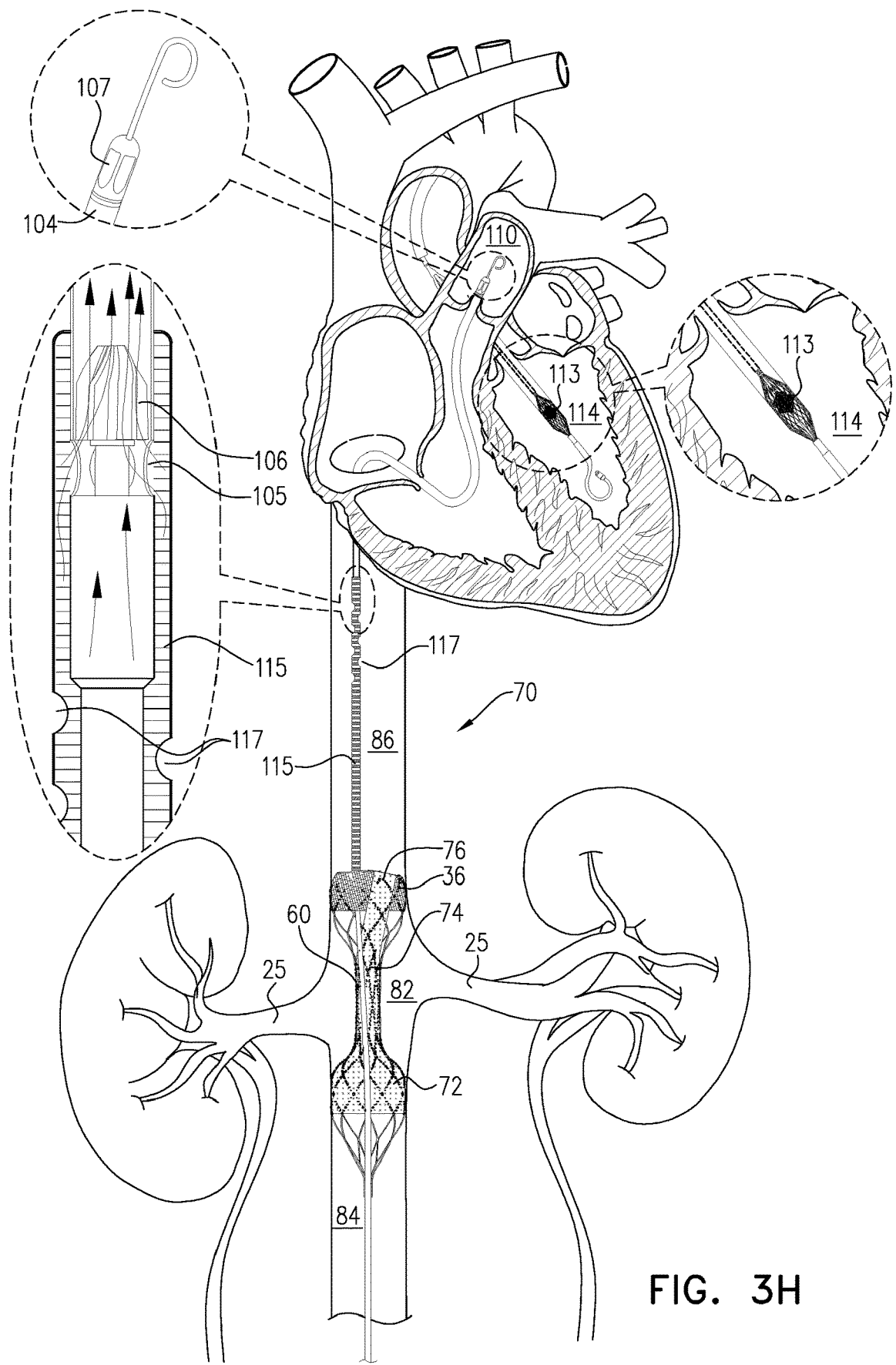

Referring now to FIG. 3H, for some applications, blood-pump catheter 70 includes elongate blood-pump tube 104 (e.g., in accordance with any one of the examples described with reference to FIGS. 3D-G), and the blood-pump catheter is used in conjunction with left-ventricular assist device 113, which is deployed within the subject's left ventricle 114, in order to assist with the subject's left heart function (e.g., as described hereinabove with reference to FIG. 3C). For some applications, the left-ventricular assist device is a left-ventricular assist device as described in U.S. Ser. No. 16/750,354 to Tuval (filed Jan. 23, 2020, entitled "Distal tip element for a ventricular assist device"), US 2019/0209758 to Tuval, and/or US 2019/0175806 to Tuval, all of which applications are incorporated herein by reference. For some applications, the left-ventricular assist device includes a left-ventricular assist device manufactured by Abiomed® (Massachusetts, USA), such as Impella 2.5®, Impella CP®, Impella 5.5®, and/or Impella 5.0®. It is noted that although left-ventricular assist device 113 is shown as being used in combination with the example of blood-pump catheter 70 shown in FIG. 3F, the scope of the present application includes using left-ventricular assist device 113 in combination with any of the examples of blood-pump catheter 70 described herein.

Figure 4A:
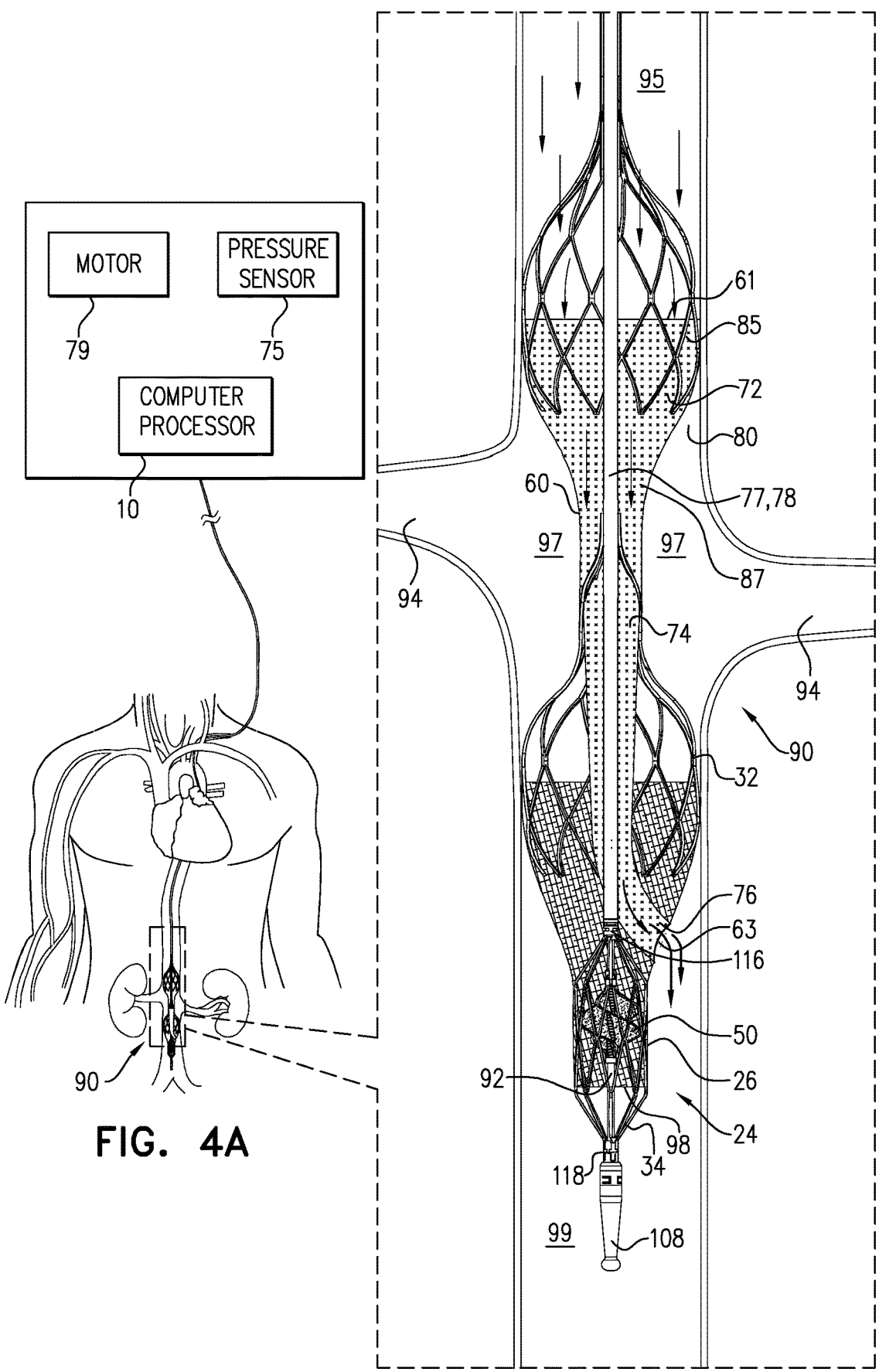
FIGS. 4A and 4B are schematic illustrations of a blood-pump catheter placed within a subject's descending aorta in the vicinity of a subject's renal arteries, in accordance with some applications of the present invention.
Figure 4B:
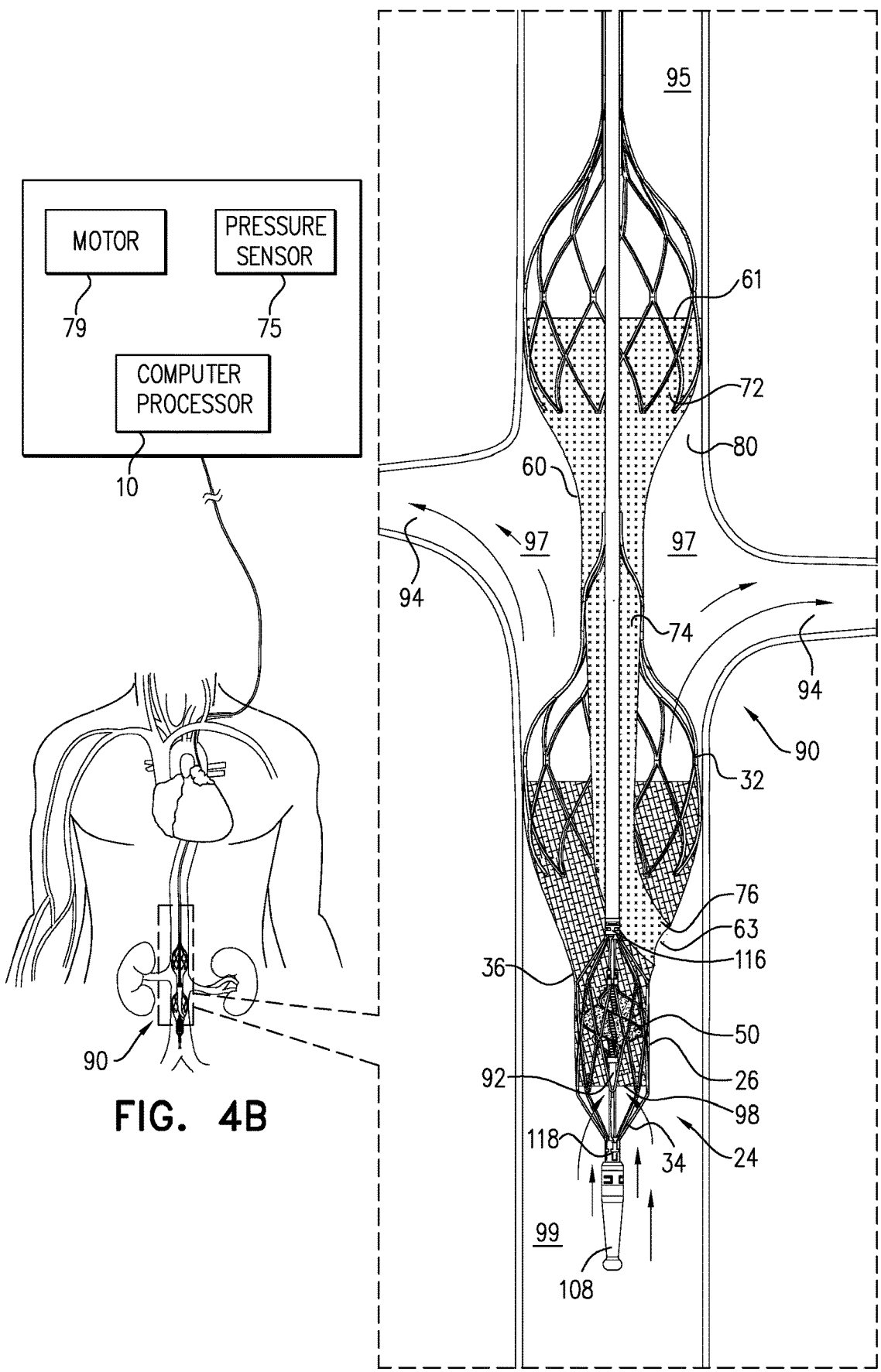

Reference is now made to FIGS. 4A and 4B, which are schematic illustrations of a blood-pump catheter 90 placed within a subject's descending aorta 80 in the vicinity of a subject's renal arteries 94, in accordance with some applications of the present invention. The structure of blood-pump catheter 90 is generally similar to that of blood-pump catheter 70 described hereinabove with reference to FIGS. 2A-F. However, blood pump 24 of blood-pump catheter 90 is typically configured to pump blood in the upstream direction, such as to enhance perfusion of an organ (such as a kidney) as described in further detail hereinbelow.

Typically, blood-pump catheter 90 includes blood pump 24, which typically includes impeller housing 26 and impeller 50, all of which are generally as described hereinabove. Impeller housing 26 (e.g., frame 34 of the housing) typically functions to separate the inner wall of the aorta from the impeller, such that the aorta does not become injured by the impeller and the impeller does not become deformed by pressure from the inner wall of the aorta. Further typically, an axial shaft 92 (show in FIG. 7) that passes through the impeller is supported by radial bearings 116, 118 disposed, respectively, at the proximal and distal ends of the impeller housing.

For some such applications, a blood-pump-support frame 32 is disposed upstream of impeller housing 26, and is configured to come into contact with the inner wall of the aorta. Blood-pump-support frame 32 is configured to align the longitudinal axis of impeller housing 26, and, in turn, impeller 50, with the local longitudinal axis of the aorta, by contacting the inner wall of the aorta. (It is noted that, for some applications, the blood-pump-support frame may not fully align the longitudinal axis of the impeller with the local longitudinal axis of the aorta. However, typically, the blood-pump-support frame maintains the longitudinal axis of the impeller in greater alignment with the local longitudinal axis of the aorta, relative to alignment of the longitudinal axis of the impeller with the local longitudinal axis of the aorta in the absence of the blood-pump-support frame.) Typically, ceteris paribus, the efficacy of the pumping of blood by impeller 50 is greater, the greater the alignment of the longitudinal axis of the impeller with the local longitudinal axis of the aorta. As noted above, a slight misalignment of the of the longitudinal axis of the impeller with the local longitudinal axis of the blood vessel in which it is placed (e.g., as shown in FIG. 2E), will nevertheless typically still result in efficacious pumping of blood by the impeller.

For some applications, impeller housing 26 includes a frame 34 (e.g., a rigid or semi-rigid frame) made of a shape-memory element (such as nitinol) that is at least partially covered with a material 36 (e.g., a blood-impermeable material, e.g., polyester, polyurethane, and/or a different polymer). Typically, for such applications, the stiffness of frame 34 is sufficiently great that pressure exerted upon the frame 34 by the inner wall of the aorta does not deform the frame. Typically, material 36 extends from the impeller housing to blood-pump-support frame 32 such as to contact the vessel wall and to occlude the blood vessel in the region of the blood vessel that surrounds the impeller and/or that is upstream of the impeller. The material typically defines a hole therethrough at a distal portion of the impeller housing. The hole is configured to act as a blood-inlet opening 98, during pumping of blood by the impeller. For some applications, a portion of the impeller housing is covered (i.e., lined) on the inside of the impeller housing with an inner lining 39, e.g., as described hereinbelow with reference to FIG. 7. For some such applications, the inner lining of the impeller housing at least partially overlaps with material 36. For some applications, the inner lining extends the blood-inlet opening defined by material 36.

Typically, a drive cable 78 is disposed within an outer tube 77 of blood-pump catheter 90. (The drive cable is shown in FIG. 8A, for example.) Typically, the drive cable extends from motor 79 which is disposed outside the subject's body, to axial shaft 92 (shown in FIG. 7), upon which the impeller is disposed. The motor imparts rotational motion to the axial shaft (and thereby imparts rotational motion to the impeller), via the drive cable. Typically, the motor is controlled by computer processor 10. For some applications, the motor is controlled, based upon blood pressure measurements that are performed by pressure sensor 75.

For some applications, the blood-pump catheter further includes a blood-flow pathway 60. For some applications, blood-flow pathway 60 includes funnel 72 that extends into tube 74. The funnel is configured to be placed upstream of junctions of the aorta with the subject's renal arteries, and is configured to direct all blood flow from the suprarenal aorta into tube 74. In turn, tube 74 directs the blood flow from the suprarenal aortic location to an infrarenal aortic location, in such a manner that this blood flows to the infrarenal location by bypassing blood pump 24 (i.e., without being pumped by blood pump 24). For example, one or more tubes 76 may extend from tube 74 to an infrarenal location while bypassing the blood pump. As indicated by the blood flow arrows in FIG. 4A, blood thereby flows from the suprarenal aorta to the infrarenal aorta without being pumped by blood pump 24. By contrast, blood is pumped from the infrarenal aorta to the renal arteries 94, by blood pump 24, as indicated by the blood flow arrows in FIG. 4B. Typically, the pumping of blood into the renal arteries enhances renal perfusion.

In this manner, by deploying the blood-pump catheter 90 the bloodstream within a region of the aorta that is adjacent to junctions of the aorta with the renal arteries is separated into a compartment 97 that is separate from the suprarenal aortic bloodstream 95 and the infrarenal aortic bloodstream 99. Blood flow from the suprarenal aortic bloodstream 95 to the infrarenal aortic bloodstream 99 occurs passively (e.g., by flowing through blood-flow pathway 60). Blood is pumped actively from infrarenal aortic bloodstream 99 to compartment 97, using blood pump.

It is noted that the specific example of the construction of funnel 72, tube 74, and tube 76, is shown by way of example, and the scope of the present applications includes using any other construction of blood-flow pathway to direct blood from the suprarenal aortic bloodstream to the infrarenal aortic bloodstream without being pumped by blood pump 24, mutatis mutandis. For some applications, funnel 72, tube 74 and tube 76 comprise respective portions of a single continuous blood-flow pathway. The blood-flow pathway typically passes between pathway-inlet opening 61 disposed at an upstream location that is upstream of junctions of the aorta with the renal arteries and pathway-outlet opening 63 that opens to a downstream side of material 36. Typically, funnel 72 defines wide end 85 and narrow end 87. The wide end of the funnel typically defines the inlet opening into the blood-flow pathway, and the narrow end of the funnel passes into one or more tubes (e.g., tubes 74 and 76).

Typically, blood flow from the suprarenal aortic bloodstream 95 to the infrarenal aortic bloodstream 99 is substantially unchanged relative to the blood flow from the suprarenal aortic bloodstream 95 to the infrarenal aortic bloodstream 99 in the absence of the blood-pump catheter. For some applications, the diameters of one or more portions of the blood-flow pathway are controlled, such as to control blood flow from the suprarenal aortic bloodstream 95 to the infrarenal aortic bloodstream 99. For example, the diameters of one or more portions of the blood-flow pathway (e.g., funnel 72, tube 74, and/or tube(s) 76) may be modulated (e.g., using an inflatable/deflatable component that is disposed inside or outside one of these portions). In this manner, blood supply to the lower body may be controlled, for example.

With reference to FIGS. 4A-B, it is noted that the scope of the present invention includes applying similar apparatus and methods to any arterial system of a subject that includes a main artery that flows into branching arteries (which typically supply an organ). For example, similar techniques could be applied at junctions of the aorta with the hepatic arteries (which supply the liver). Typically, such methods include separating bloodstream within a region of the main artery that is adjacent to junctions of the main artery with the branching arteries from bloodstream within the main artery upstream and downstream thereto, enhancing perfusion of the organ, by pumping blood from the main artery to the region of the main artery that is adjacent to junctions of the main artery with the branching arteries, using a pump, and allowing the subject's blood to flow from a location within the main artery that is upstream of the branching arteries to a location within the main artery that is downstream of the branching arteries without being pumped by the pump, by directing the blood to bypass the pump. For some applications, such methods include at least partially occluding blood flow through the main artery by placing a downstream occluding element (e.g., material 36) at a downstream location that is downstream of junctions of the main artery with the branching arteries, enhancing perfusion of the organ, by pumping blood from the region of the main artery that is adjacent to junctions of the main artery with the branching arteries and through the downstream occluding element, using a pump (e.g., blood pump 24), and directing upstream main artery blood flow from an upstream location that is upstream of junctions of the main artery with the branching arteries to downstream of the occluding element, without the upstream main artery blood flow being pumped by the pump, by directing the upstream main artery blood flow to bypass the pump. Typically, a blood-pump catheter such as blood-pump catheter 90 is used, the blood-pump catheter including material 36 configured to be placed at a downstream location that is downstream of junctions of the main artery with the branching arteries and to at least partially occlude blood flow through the main artery at the downstream location, the material defining blood-inlet opening 98. Blood pump 24 is typically configured to pump blood from the main artery toward the region of the main artery that is adjacent to junctions of the main artery with the branching arteries, through the blood-inlet opening. Blood-flow pathway 60 typically passes between pathway-inlet opening 61 disposed at an upstream location that is upstream of junctions of the main artery with the branching arteries and pathway-outlet opening 63 that opens to a downstream side of material 36. For some applications, the blood-flow pathway comprises funnel 72 and one or more tubes (e.g., tubes 74 and 76). Funnel 72 is configured to be disposed at an upstream location that is upstream of junctions of the main artery with the branching arteries, and one or more tubes 74, 76 (or alternative blood-flow pathways) are configured to extend from the funnel to a downstream side of the material. The funnel and the one or more tubes (or alternative blood-flow pathway) are typically configured to direct upstream main arterial blood flow from the upstream location to downstream of the material, without the upstream main arterial blood flow being pumped by the pump. Typically, funnel 72 defines wide end 85 and narrow end 87. The wide end of the funnel typically defines the inlet opening into the blood-flow pathway, and the narrow end of the funnel passes into one or more tubes (e.g., tubes 74 and 76).

Figure 5A:
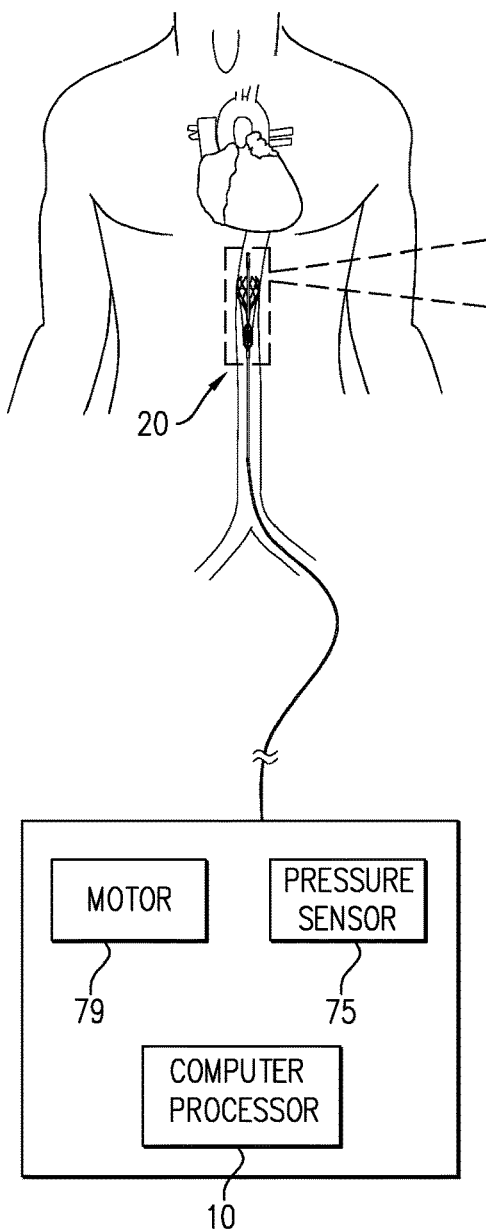
FIGS. 5A and 5B are schematic illustrations of a blood-pump catheter placed within a subject's descending aorta (e.g., the thoracic aorta or the abdominal aorta), in accordance with some applications of the present invention.
Figure 5A:
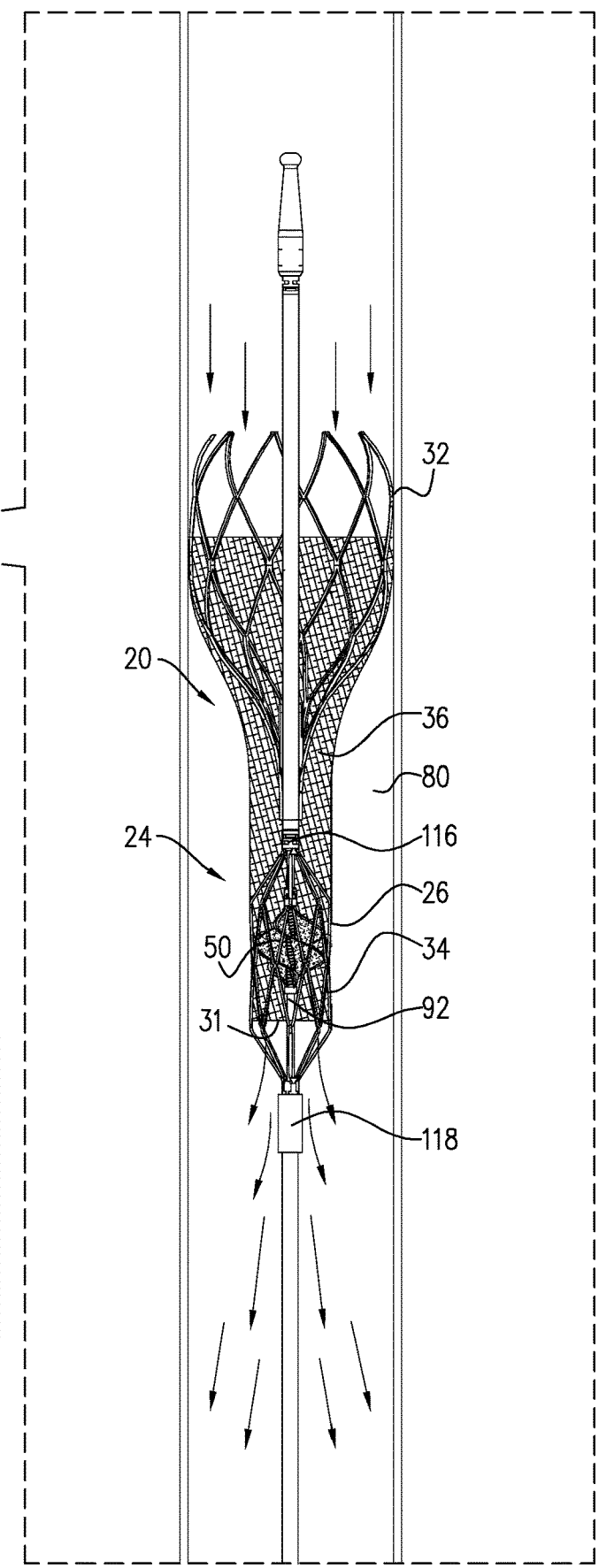
Figure 5B:
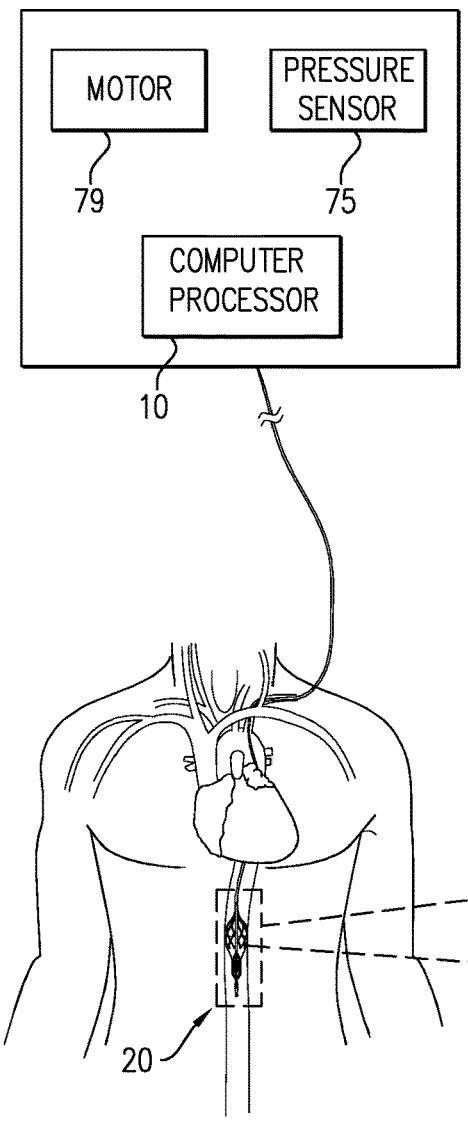
Figure 5B:
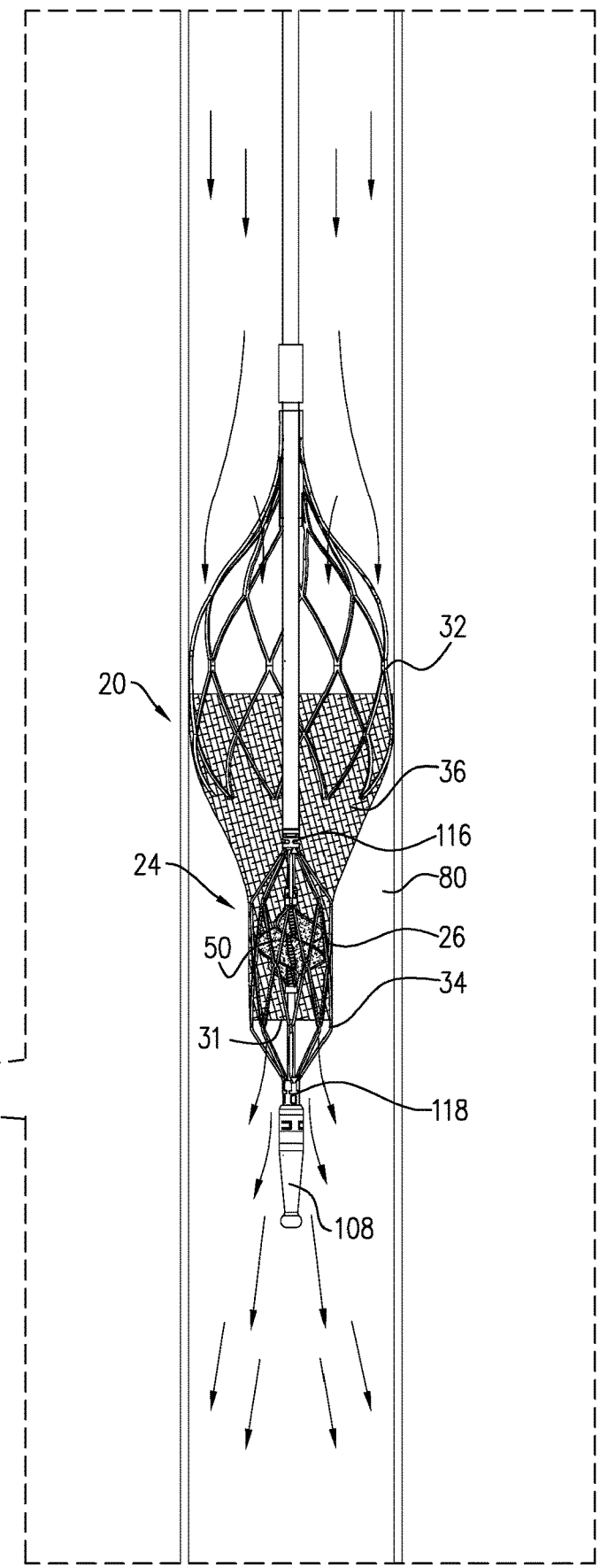

Reference is now made to FIGS. 5A-B, which are schematic illustrations of blood-pump catheter 20 placed in a subject's descending aorta 80, in accordance with some applications of the present invention. Typically, blood-pump catheter 20 is generally as described hereinabove, the blood-pump catheter including blood pump 24, which typically includes impeller housing 26 and impeller 50, all of which are generally as described hereinabove. Impeller housing 26 (e.g., frame 34 of the housing) typically functions to separate the inner wall of the aorta from the impeller, such that the aorta does not become injured by the impeller and the impeller does not become deformed by pressure from the inner wall of the aorta. Further typically, axial shaft 92 (shown in FIG. 7) that passes through the impeller is supported by radial bearings 116, 118 that are disposed, respectively, at proximal and distal ends of the impeller housing.

For some such applications, a blood-pump-support frame 32 is disposed upstream of impeller housing 26, and is configured to come into contact with the inner wall of the aorta. Blood-pump-support frame 32 is configured to align the longitudinal axis of impeller housing 26, and, in turn, impeller 50, with the local longitudinal axis of the aorta, by contacting the inner wall of the aorta. (It is noted that, for some applications, the blood-pump-support frame may not fully align the longitudinal axis of the impeller with the local longitudinal axis of the aorta. However, typically, the blood-pump-support frame maintains the longitudinal axis of the impeller in greater alignment with the local longitudinal axis of the aorta, relative to what the alignment of the longitudinal axis of the impeller with the local longitudinal axis of the aorta would be in the absence of the blood-pump-support frame.) Typically, ceteris paribus, the efficacy of the pumping of blood by impeller 50 is greater, the greater the alignment of the longitudinal axis of the impeller with the local longitudinal axis of the aorta.

For some applications, impeller housing 26 includes a frame 34 (e.g., a rigid or semi-rigid frame) made of a shape-memory element (such as nitinol) that is at least partially covered with a material 36 (e.g., a blood-impermeable material, e.g., polyester, polyurethane, and/or a different polymer). Typically, for such applications, the stiffness of frame 34 is sufficiently great that pressure exerted upon the frame 34 by the inner wall of the aorta does not deform the frame 34. Typically, material 36 extends from the impeller housing to blood-pump-support frame 32 to the impeller housing such as to contact the vessel wall and to occlude the blood vessel in the region of the blood vessel that surrounds the impeller and/or that is upstream of the impeller. The material typically defines a hole therethrough at a distal portion of the impeller housing. The material is configured to occlude backflow of blood around the outside of the impeller, but such to allow antegrade blood flow in the central region of the vessel in the vicinity of the impeller, by the hole acting as a blood-outlet opening 31. For some applications, a portion of the impeller housing is covered (i.e., lined) on the inside of the impeller housing with an inner lining 39, e.g., as described hereinbelow with reference to FIG. 7. For some such applications, the inner lining of the impeller housing at least partially overlaps with material 36. For some applications, the inner lining extends the blood-outlet opening defined by material 36.

Typically, a drive cable 78 is disposed within an outer tube 77 of blood-pump catheter 90. (The drive cable is shown in FIG. 8A, for example.) Typically, the drive cable extends from motor 79 which is disposed outside the subject's body, to axial shaft 92 (shown in FIG. 7), upon which the impeller is disposed. The motor imparts rotational motion to the axial shaft (and thereby imparts rotational motion to the impeller), via the drive cable. Typically, the motor is controlled by computer processor 10. For some applications, the motor is controlled, based upon blood pressure measurements that are performed by pressure sensor 75. Covering material 36 effectively separates the descending aorta into two compartments, and the blood pump pumps blood from the upstream compartment to the downstream compartment. In this manner, the blood pump typically augments aortic blood flow and/or reduces left ventricular afterload.

Referring to FIG. 5A, for some applications, the blood pump is inserted into the descending aorta via an artery that is below the descending aorta, such as the femoral artery. Alternatively or additionally, the blood pump is inserted into the descending aorta via an artery that is above the descending aorta, e.g., via the radial artery, or the subclavian artery, as shown in FIG. 5B. For some applications, the blood-pump catheter is inserted into the subject's aortic arch, rather than the descending aorta, mutatis mutandis.

For some applications, impeller 50, impeller housing 26, frame 34, and/or other components of the blood pump catheters described herein have similar characteristics to components described in U.S. Ser. No. 16/750,354 to Tuval (filed Jan. 23, 2020, entitled "Distal tip element for a ventricular assist device"), US 2019/0209758 to Tuval, US 2019/0239998 to Tuval, and/or US 2019/0175806 to Tuval, all of which applications are incorporated herein by reference. For example, some of these characteristics are described hereinbelow with reference to FIG. 6A-8C.

Reference is now made to FIGS. 6A-C, which are schematic illustrations of impeller 50 or portions thereof, in accordance with some applications of the present invention. Typically, the impeller includes at least one outer helical elongate element 52, which winds around a central axial spring 54, such that the helix defined by the helical elongate element is coaxial with the central axial spring. Typically, the impeller includes two or more helical elongate elements (e.g., three helical elongate elements, as shown in FIGS. 6A-C). For some applications, the helical elongate elements and the central axial spring are made of a shape-memory material, e.g., a shape-memory alloy such as nitinol. Typically, each of the helical elongate elements and the central axial spring support a film 56 of a material (e.g., an elastomer, such as polyurethane, and/or silicone) therebetween. For some applications, the film of material includes pieces of nitinol embedded therein, for example in order to strengthen the film of material. For illustrative purposes, the impeller is shown in the absence of the material in FIG. 6A. FIGS. 6B and 6C show respective views of the impeller with the material supported between the helical elongate elements and the spring.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 6B and 6C) are wound around the helical elongate elements, e.g., as described in US 2016/0022890 to Schwammenthal, which is incorporated herein by reference. Typically, the sutures are configured to facilitate bonding between the film of material (which is typically an elastomer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol).

Enlargements A and B of FIG. 6C show two alternative ways in which the sutures are tied around helical elongate elements 52. For some applications, the sutures are tied around the outer surface of the helical elongate elements, as shown in enlargement A. Alternatively, the helical elongate elements define grooves 48 on their outer surfaces, and the sutures are embedded within the grooves, as shown in enlargement B. By embedding the sutures within the grooves, the sutures typically do not add to the outer profile of the impeller, and the outer profile of the impeller is defined by the outer surfaces of the helical elongate elements.

Typically, proximal ends of spring 54 and helical elongate elements 52 extend from a proximal bushing (i.e., sleeve bearing) 64 of the impeller, such that the proximal ends of spring 54 and helical elongate elements 52 are disposed at a similar radial distance from the longitudinal axis of the impeller, as each other. Similarly, typically, distal ends of spring 54 and helical elongate elements 52 extend from a distal bushing 58 of the impeller, such that the distal ends of spring 54 and helical elongate elements 52 are disposed at a similar radial distance from the longitudinal axis of the impeller, as each other. Typically, spring 54, as well as proximal bushing 64 and distal bushing 58 of the impeller, define a lumen 62 therethrough (shown in FIG. 6C).

Reference is now made to FIG. 7, which is a schematic illustration of impeller 50 disposed inside frame 34 of blood-pump catheter 20, 70 or 90, in accordance with some applications of the present invention. For some applications, within at least a portion of frame 34, inner lining 39 lines the frame. In accordance with respective applications, the inner lining partially overlaps or fully overlaps with covering material 36 over the portion of the frame that the inner lining lines. In the application shown in FIG. 7, the inner lining lines (i.e., covers) the inside of a cylindrical portion 38 of the frame and covering material 36 does not cover the cylindrical portion of the frame. For such applications, the inner lining extends the blood-inlet opening or the blood-outlet opening of the blood pump.

As shown in FIG. 7, typically there is a gap G, between the outer edge of impeller 50 and inner lining 39, even at a location at which the span of the impeller is at its maximum. For some applications, it is desirable that the gap between the outer edge of the blade of the impeller and the inner lining 39 be relatively small, in order for the impeller to efficiently pump blood. However, it is also desirable that a gap between the outer edge of the blade of the impeller and inner lining 39 be maintained substantially constant throughout the rotation of the impeller within frame 34, for example, in order to reduce the risk of hemolysis.

For some applications, when the impeller and frame 34 are both disposed in non-radially-constrained configurations, gap G between the outer edge of the impeller and the inner lining 39, at the location at which the span of the impeller is at its maximum, is greater than 0.05 mm (e.g., greater than 0.1 mm), and/or less than 1 mm (e.g., less than 0.4 mm), e.g., 0.05-1 mm, or 0.1-0.4 mm. For some applications, when the impeller is disposed in its non-radially-constrained configuration, the outer diameter of the impeller at the location at which the outer diameter of the impeller is at its maximum is more than 7 mm (e.g., more than 8 mm), and/or less than 10 mm (e.g., less than 9 mm), e.g., 7-10 mm, or 8-9 mm. For some applications, when frame 34 is disposed in its non-radially-constrained configuration, the inner diameter of cylindrical portion 38 of frame 34 (as measured from the inside of inner lining 39 on one side of the frame to the inside of inner lining on the opposite side of the frame) is greater than 7.5 mm (e.g., greater than 8.5 mm), and/or less than 10.5 mm (e.g., less than 9.5 mm), e.g., 7.5-10.5 mm, or 8.5-9.5 mm. For some applications, when the frame is disposed in its non-radially-constrained configuration, the outer diameter of cylindrical portion 38 of frame 34 is greater than 8 mm (e.g., greater than 9 mm), and/or less than 13 mm (e.g., less than 12 mm), e.g., 8-13 mm, or 9-12 mm.

Typically, axial shaft 92 passes through the axis of impeller 50, via lumen 62 of the impeller. Further typically, the axial shaft is rigid, e.g., a rigid tube. For some applications, proximal bushing 64 of the impeller is coupled to the shaft such that the axial position of the proximal bushing with respect to the shaft is fixed, and distal bushing 58 of the impeller is slidable with respect to the shaft. The axial shaft itself is radially stabilized via proximal radial bearing 116 and distal radial bearing 118. (It is noted that in FIG. 7, distal radial bearing 118 is not visible since it is disposed under distal-tip element 108. However, the distal radial bearing is visible in embodiments shown in other figures, e.g., FIGS. 1A-C, 2A-E, and 4A-B.) In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 6A-C, for some applications, the impeller includes a plurality of elongate elements 67 extending radially from central axial spring 54 to outer helical elongate elements 52. The elongate elements are typically flexible but are substantially non-stretchable along the axis defined by the elongate elements. Further typically, each of the elongate elements is configured not to exert force upon the helical elongate element, unless force is acting upon the impeller that is causing the helical elongate element to move radially outward, such that (in the absence of the elongate element) a separation between the helical elongate element and the central axial spring would be greater than a length of the elongate element. For example, the elongate elements may include strings (such as polyester, and/or another polymer or a natural material that contains fibers) and/or wires (such as nitinol wires, and/or wires made of a different alloy, or a metal).

For some applications, the elongate elements 67 maintain the helical elongate element (which defines the outer edge of the impeller blade) within a given distance with respect to the central axial spring. In this manner, the elongate elements are configured to prevent the outer edge of the impeller from being forced radially outward due to forces exerted upon the impeller during the rotation of the impeller. The elongate elements are thereby configured to maintain the gap between the outer edge of the blade of the impeller inner lining 39 of frame 34, during rotation of the impeller. Typically, more than one (e.g., more than two) and/or fewer than eight (e.g., fewer than four) elongate elements 67 are used in the impeller, with each of the elongate elements typically being doubled (i.e., extending radially from central axial spring 54 to an outer helical elongate element 52, and then returning from the helical elongate element back to the central axial spring). For some applications, a plurality of elongate elements, each of which extends from the spring to a respective helical elongate element and back to the spring, are formed from a single piece of string or a single wire, as described in further detail hereinbelow.

For some applications, the impeller is manufactured in the following manner. Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements are defined by the shape-memory material, e.g., using generally similar techniques to those described in US 2016/0022890 to Schwammenthal. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

For some applications, subsequent to spring 54 being inserted into the cut and shape-set tube, elongate elements 67, as described hereinabove, are placed such as to extend between the spring and one or more of the helical elongate elements, for example, in the following manner. A mandrel (e.g., a polyether ether ketone (PEEK) and/or a polytetrafluoroethylene (PTFE) mandrel) is inserted through the lumen defined by the spring and the bushings. A string or a wire is then threaded such that it passes (a) from the mandrel to a first one of the helical elongate elements, (b) back from the first of the helical elongate elements to the mandrel, (c) around the mandrel, and to a second one of the helical elongate elements, (d) back from the second one of the helical elongate elements to the mandrel, etc. Once the string or the wire has been threaded from the mandrel to each of the helical elongate elements and back again, the ends of the string or the wire are coupled to each other, e.g., by tying them to each other. For some applications, sutures 53 (e.g., polyester sutures) are wound around the helical elongate elements, in order to facilitate bonding between the film of material (which is typically an elastomer, such as polyurethane, or silicone) and the helical elongate elements (which is typically a shape-memory alloy, such as nitinol), in a subsequent stage of the manufacture of the impeller. For some applications, sutures (e.g., polyester sutures, not shown) are wound around spring 54. Typically, the sutures are configured to facilitate bonding between the film of material (which is typically an elastomer, such as polyurethane, or silicone) and the spring (which is typically a shape-memory alloy, such as nitinol), in the subsequent stage of the manufacture of the impeller.

Typically, at this stage, a structure 59 has been assembled that is as shown in FIG. 6A. The structure includes the cut and shape-set tube that defines the proximal and distal bushings, the helical elongate elements, and the spring (and, optionally, the elongate elements, and the sutures). This structure is dipped into the material that defines film 56. For some applications, the assembled structure is dipped into the material with the mandrel disposed through the lumen defined by the spring and the bushings, although it is noted that the mandrel is not shown in FIG. 6A. Typically, the material from which the film is made is silicone and/or polyurethane (and/or a similar elastomer), and the assembled structure is dipped into the material, while the material is in an uncured, liquid state. Subsequently, the material is cured such that it solidifies, e.g., by being left to dry. Once the material has dried, the mandrel is typically removed from the lumen defined by the bushings and the spring.

The result of the process described above is typically that there is a continuous film of material extending between each of the helical elongate elements to the spring, and also extending along the length of the spring, such as to define a tube, with the spring embedded within the tube. The portions of the film that extend from each of the helical elongate elements to the spring define the impeller blades. For applications in which the impeller includes elongate elements 67, the elongate elements are typically embedded within these portions of the film.

Typically, impeller 50 is inserted into the subject's body, while impeller 50 is in a radially-constrained configuration. In the radially-constrained configuration, both helical elongate elements 52 and central axial spring 54 become axially elongated, and radially constrained. Typically film 56 of the material (e.g., silicone and/or polyurethane) changes shape to conform to the shape changes of the helical elongate elements and the axial support spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

For some applications, proximal bushing 64 of impeller 50 is coupled to axial shaft 92 such that the axial position of the proximal bushing with respect to the shaft is fixed, and distal bushing 58 of the impeller is slidable with respect to the shaft. For some applications, when the impeller is radially constrained for the purpose of inserting the impeller into the subject's body or for the purpose of withdrawing the impeller from the subject's body, the impeller axially elongates by the distal bushing sliding along the axial shaft distally. Subsequent to being released inside the subject's body, the impeller assumes its non-radially-constrained configuration (in which the impeller is typically disposed during operation of the impeller), as shown in FIGS. 6A-C.

It is noted that, for illustrative purposes, in some of the figures, impeller 50 is shown without including all of the features of the impeller as shown and described with respect to FIGS. 6A-C. The scope of the present application includes using an impeller with any of the features shown and described with respect to FIGS. 6A-C in combination with any of the apparatus and methods described herein.

Figure 6D:
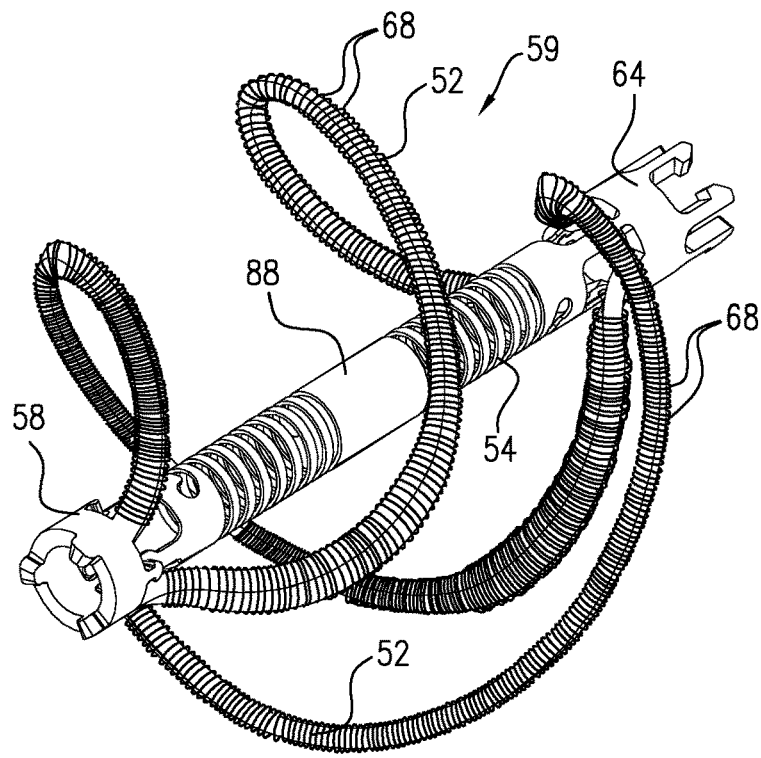
Figure 6E:
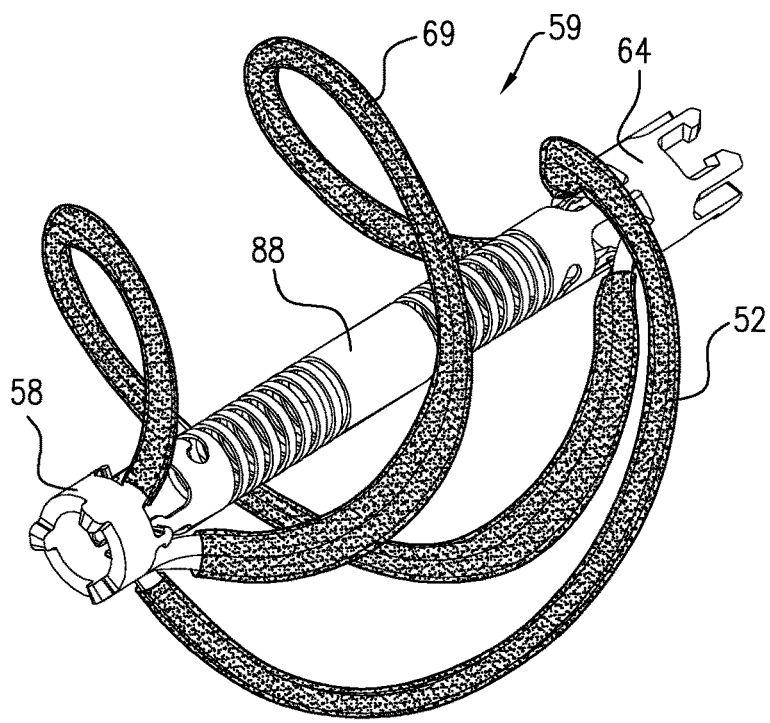
Figure 6F:
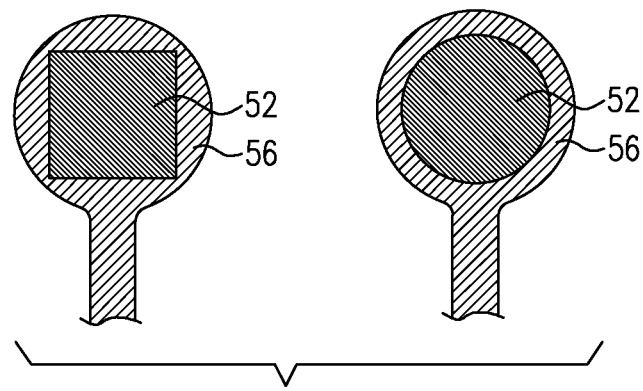

Reference is now made to FIGS. 6D, 6E, and 6F, which are schematic illustration of impeller 50 or portions thereof, in accordance with some applications of the present invention. As described hereinabove, for some applications, impeller 50 includes sutures 53. Sutures 53 are wound around the helical elongate elements 52 and are configured to facilitate bonding between the film of material (which is typically an elastomer, such as polyurethane, or silicone) and the helical elongate element (which is typically a shape-memory alloy, such as nitinol).

As an alternative or in addition to sutures 53, for some applications, coils 68 are wound around (or placed over) the helical elongate elements, as shown in FIG. 6D. For example, a tightly-wound coil (e.g., a tightly-wound nitinol coil) may be wound around (or placed around) each of the helical elongate elements. The coil typically facilitates bonding between the film of material and the helical elongate element by increasing the surface area to which the material bonds at the interface between the material and the helical elongate element. For some applications, structure 59 is formed modularly (e.g., as described hereinbelow with reference to FIG. 6F.) For some such applications, the coils are placed around each of the elongate elements 52 (e.g., by sliding the entire coil over the elongate element in a single action), prior to the elongate elements being coupled to the proximal and distal bushings of the impeller.

As a further alternative to or in addition to sutures 53, for some applications, sleeves 69 are placed around the helical elongate elements, as shown in FIG. 6E. For example, such sleeves may be made of a polymer, such as polyester. The sleeves typically facilitate bonding between the film of material and the helical elongate elements by increasing the surface area to which the material bonds at the interfaces between the material and the helical elongate elements. For some applications, the sleeve acts as a mediator between a material from which the elongate elements are made, which typically has a relatively high stiffness (and is typically nitinol), and the material from which film 56 is made, which is typically an elastomer having a relatively low stiffness. The sleeve thereby enhances the strength of the coupling between the material and the helical elongate elements, when the material dries. For some applications, sleeves 69 are applied to structure 59. For some such applications, longitudinal slits are formed in the sleeves in order to allow the sleeves to be placed around the helical elongate elements 52. Subsequent to being placed around helical elongate elements 52 the slits are closed (e.g., by suturing or adhering the slits closed). For some applications, structure 59 is formed modularly (e.g., as described hereinbelow with reference to FIG. 6F.) For some such applications, the sleeves are placed around elongate elements 52, prior to the elongate elements being coupled to the proximal and distal bushings of the impeller.

As yet a further alternative to or in addition to sutures 53, for some applications, elongate elements 52 are shaped to have a rounded (e.g., a circular) cross section, as shown in the right portion of FIG. 6F (which shows a cross-sectional view of an elongate element having a rounded cross-section). The left portion of FIG. 6F shows a cross-sectional view of elongate element 52 with material of film 56 coupled to the elongate element, in a case in which the elongate element has a non-rounded cross section (e.g., a square or a rectangular cross section). As shown, it is sometimes the case that the material (e.g., the silicone and/or the polyurethane) from which the film is made forms a thinner layer at the corners of an elongate element having a non-rounded cross-section. By contrast as shown in the left portion of FIG. 6F, when the elongate element has a rounded cross section, the material typically forms a layer having a substantially uniform thickness at the interface with the elongate element. Therefore, for some applications, the elongate elements have rounded cross sections.

For some applications, proximal and distal bushings 64, 58 and elongate elements 52 are cut from an alloy tube, e.g., as described hereinabove. For such applications, after the tube is cut, the elongate elements typically have non-rounded edges. Therefore, for some applications, subsequent to the tube being cut, the edges of the elongate elements are rounded, for example, using grinding, sandblasting, tumble finishing, etching, plasma, surface-charging, and/or by adding rounded edges to the elongate elements. Alternatively, the proximal and distal bushings and the elongate elements may be formed in a modular manner, and may subsequently be coupled to each other (e.g., via welding, and/or swaging). For some such applications, the elongate elements that are coupled to the proximal and distal bushings have rounded cross sections. As described hereinabove with reference to FIG. 6E, for some applications, sleeves 69 are placed on the elongate elements prior to the elongate elements being coupled to the proximal bushing and/or prior to the elongate elements being coupled to the distal bushing.

For some applications, alternative or additional techniques are used to facilitate bonding between the film of material and the helical elongate elements. For example, the helical elongate elements may be treated using a surface treatment (such as, grinding, sandblasting, tumble finishing, etching, plasma, surface-charging, etc.), in order to roughen the outer surface of the helical elongate elements.

In accordance with the above description of FIGS. 6A-F, for some applications of the present invention, impeller 50 is manufactured by forming a structure having first and second bushings 64, 58 at proximal and distal ends of the structure, the first and second bushings being connected to one another by at least one elongate element 52. The at least one elongate element is made to radially expand and form at least one helical elongate element, at least partially by axially compressing the structure. An elastomeric material is coupled to the at least one helical elongate element, such that the at least one helical elongate element with the elastomeric material coupled thereto defines a blade of the impeller. Typically, the coupling is performed such that a layer of the material is disposed around a radially outer edge of the at least one helical elongate element, the layer of material forming the effective edge of the impeller blade (i.e., the edge at which the impeller's blood-pumping functionality substantially ceases to be effective). Further typically, the method includes performing a step to enhance bonding of the elastomeric material to the at least one helical elongate element in a manner that does not cause a protrusion from the effective edge of the impeller blade. For example, sutures 53 may be placed within grooves defined by the at least one helical elongate element, such that the sutures do not protrude from the radially outer edge of the helical elongate element, the sutures being configured to enhance bonding of the elastomeric material to the at least one helical elongate element. Alternatively or additionally, tightly-wound coil 68 may be placed around the at least one helical elongate element, such that the elastomeric material forms a substantially smooth layer along a radially outer edge of the coil, the coil being configured to enhance bonding of the elastomeric material to the at least one helical elongate element. Further alternatively or additionally, sleeve 69 may be placed around the at least one helical elongate element, such that the elastomeric material forms a substantially smooth layer along a radially outer edge of the sleeve, the sleeve being configured to enhance bonding of the elastomeric material to the at least one helical elongate element. For some applications, a rounded cross section is provided to the at least one helical elongate element, such that the elastomeric material forms a layer having a substantially uniform thickness at an interface of the elastomeric material with the helical elongate element. As noted hereinabove, it is typically desirable that gap G between the outer edge of the blade of the impeller and the inner lining 39 (shown in FIG. 7) be relatively small. Therefore, it is desirable that there be no protrusion from the effective edge of the impeller blade, since this would occupy some of the gap between the outer edge of the impeller blade (thereby requiring a larger gap), without increasing the effectiveness of the blood-pumping functionality of the impeller.

Figure 6G:
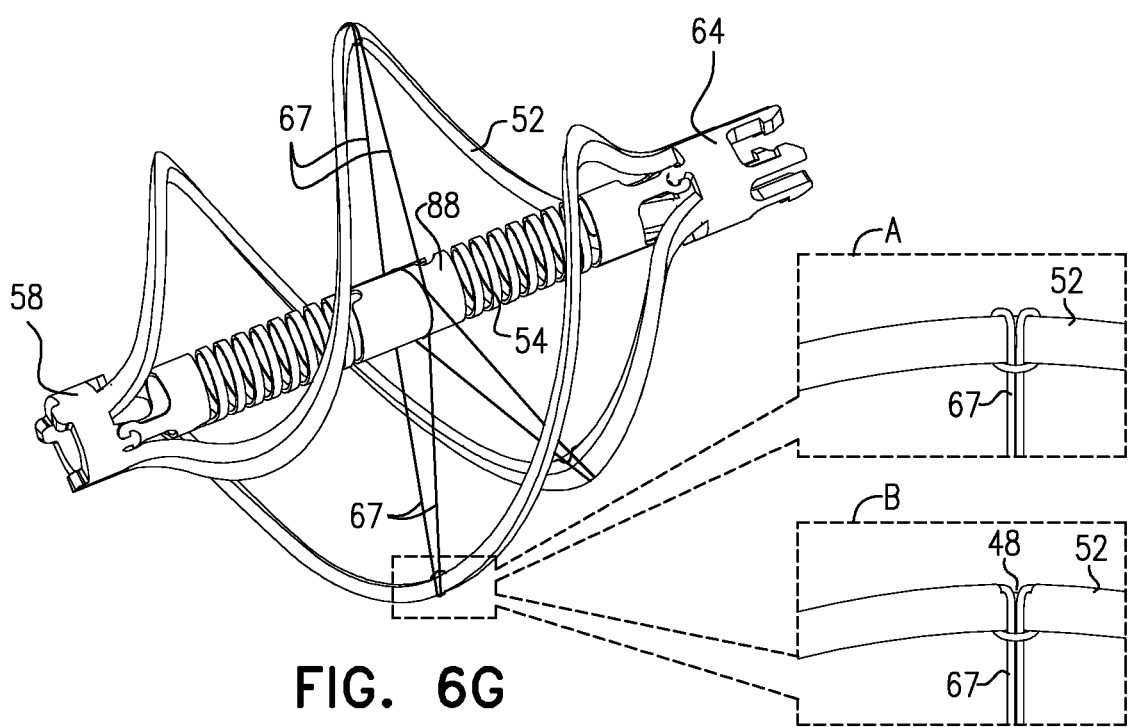
Figure 6H:
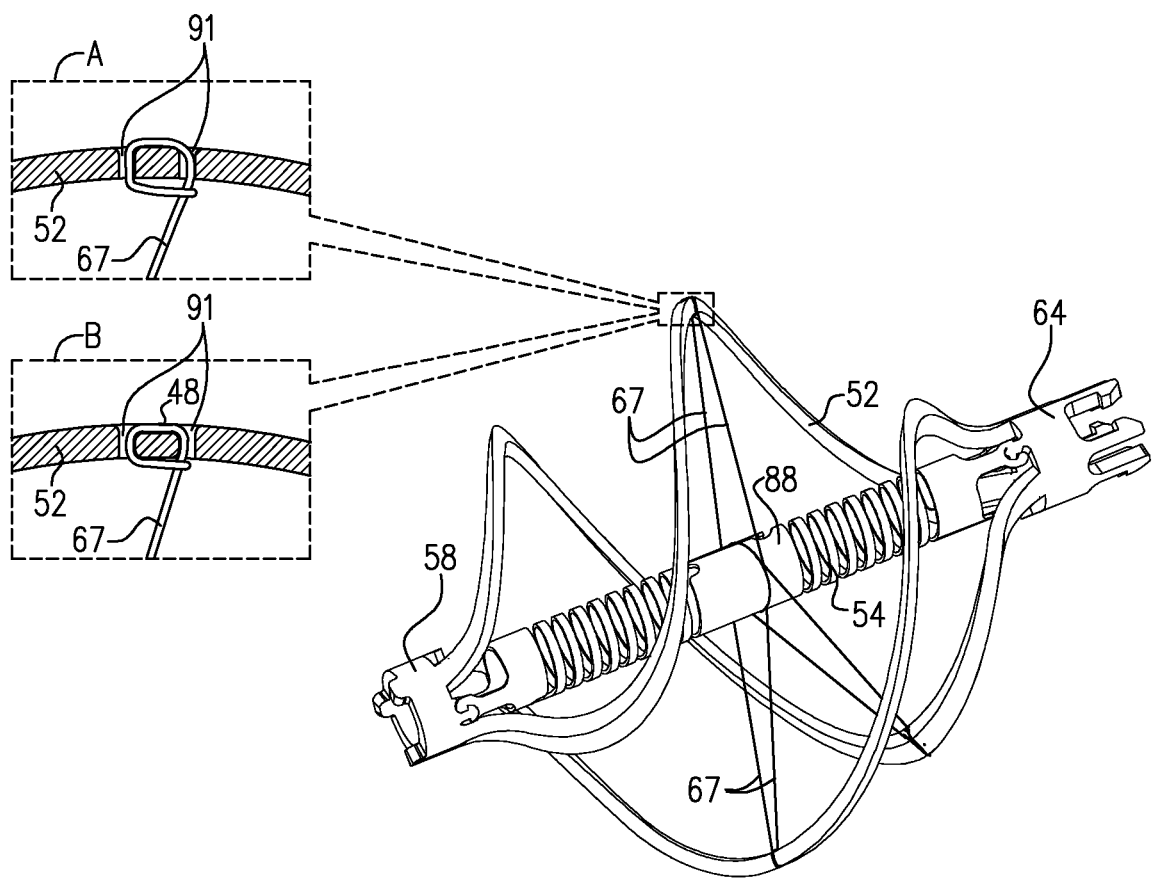

Reference is now made to FIGS. 6G and 6H, which are schematic illustrations of elongate elements 67 extending between each of the helical elongate elements 52 and spring 54, in accordance with some applications of the present invention. For some applications, a respective looped elongate element 67 extends between each of the helical elongate elements and the spring. Typically, the looped elongate elements are closed loops that have predefined lengths and are (substantially) non-stretchable. The lengths of the looped elongate elements are typically predefined, such as to maintain the helical elongate element (which defines the outer edge of the impeller blade) within a given distance with respect to the central axial spring, and to thereby maintain the gap between the outer edge of the blade of the impeller and the inner surface of frame 34, during rotation of the impeller, as described hereinabove. For some applications, the impeller is formed by looping first ends of the looped elongate elements around each of the helical elongate elements as indicated in the enlarged portions of FIGS. 6G and 6H. Subsequently, spring 54 is inserted through proximal and distal bushings 64, 58, and through second ends of the looped helical elongate elements.

For some applications, at a longitudinally-central location of spring 54, the spring is shaped to define a tube 88 (i.e., without windings), as shown in FIGS. 6G and 6H. Typically, the second ends of the looped elongate elements loop around the tube at the longitudinally-central location of the spring. Typically, this reduces a risk of the looped elongate elements tearing, relative to if the second ends of the looped elongate elements were to loop around windings of the spring. For some applications (not shown), the tube defines a groove therein and the second ends of the looped elongate elements are configured to be held within the groove.

For some applications, the looped elongate element is looped around the body of the helical elongate element, as shown in the enlarged portions of FIG. 6G. Enlargements A and B of FIG. 6G show two alternative ways in which the looped elongate element is looped around the body of the helical elongate element. For some applications, the looped elongate element is looped around the outer surface of the helical elongate element, as shown in enlargement A. Alternatively, the helical elongate elements define grooves 48 on their outer surfaces, and the looped elongate element is looped around a groove 48 (such as to become embedded within the groove), as shown in enlargement B. By embedding the looped elongate element within the grooves, the looped elongate element typically does not add to the outer profile of the impeller, and the outer profile of the impeller is defined by the outer surfaces of the helical elongate elements.

For some applications, the helical elongate element is shaped to define two holes 91 disposed in close proximity to each other, and the looped elongate element may be looped through the holes, as shown in the enlarged portions of FIG. 6H. Enlargements A and B of FIG. 6H show two alternative ways in which the looped elongate element is looped through holes 91. For some applications, the looped elongate element is looped around the outer surface of the helical elongate element and through holes 91, as shown in enlargement A. Alternatively, the helical elongate elements define grooves 48 on their outer surfaces, and the looped elongate element is looped around groove 48 and through holes 91 (such as to become embedded within the groove), as shown in enlargement B. By embedding the looped elongate element within the grooves, the looped elongate element typically does not add to the outer profile of the impeller, and the outer profile of the impeller is defined by the outer surfaces of the helical elongate elements.

Figure 8B:
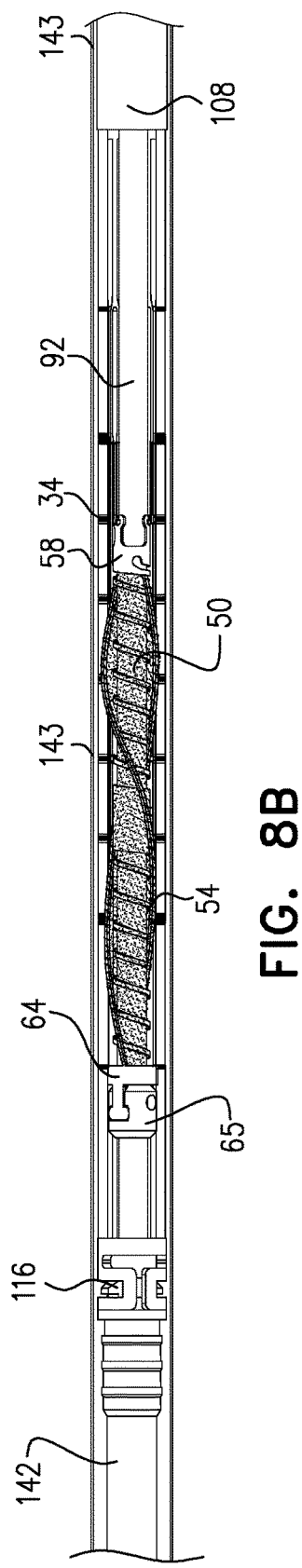

Reference is now made to FIGS. 8A and 8B, which are schematic illustrations of impeller 50 and frame 34 of blood-pump catheter 20, 70, or 90, respectively in non-radially-constrained and radially-constrained states thereof, in accordance with some applications of the present invention. The impeller and the frame are typically disposed in radially-constrained states during the transcatheteral insertion of the impeller and the frame into the subject's body, and are disposed in non-radially-constrained states during operation of the blood-pump catheter. As described hereinabove, typically covering material 36 extends from frame 34. However, for illustrative purposes, the frame and the impeller are shown in the absence of covering material 36 in FIGS. 8A-B. As indicated in FIG. 8B, the frame and the impeller are typically maintained in radially-constrained configurations by a delivery catheter 143.

Figure 8C:
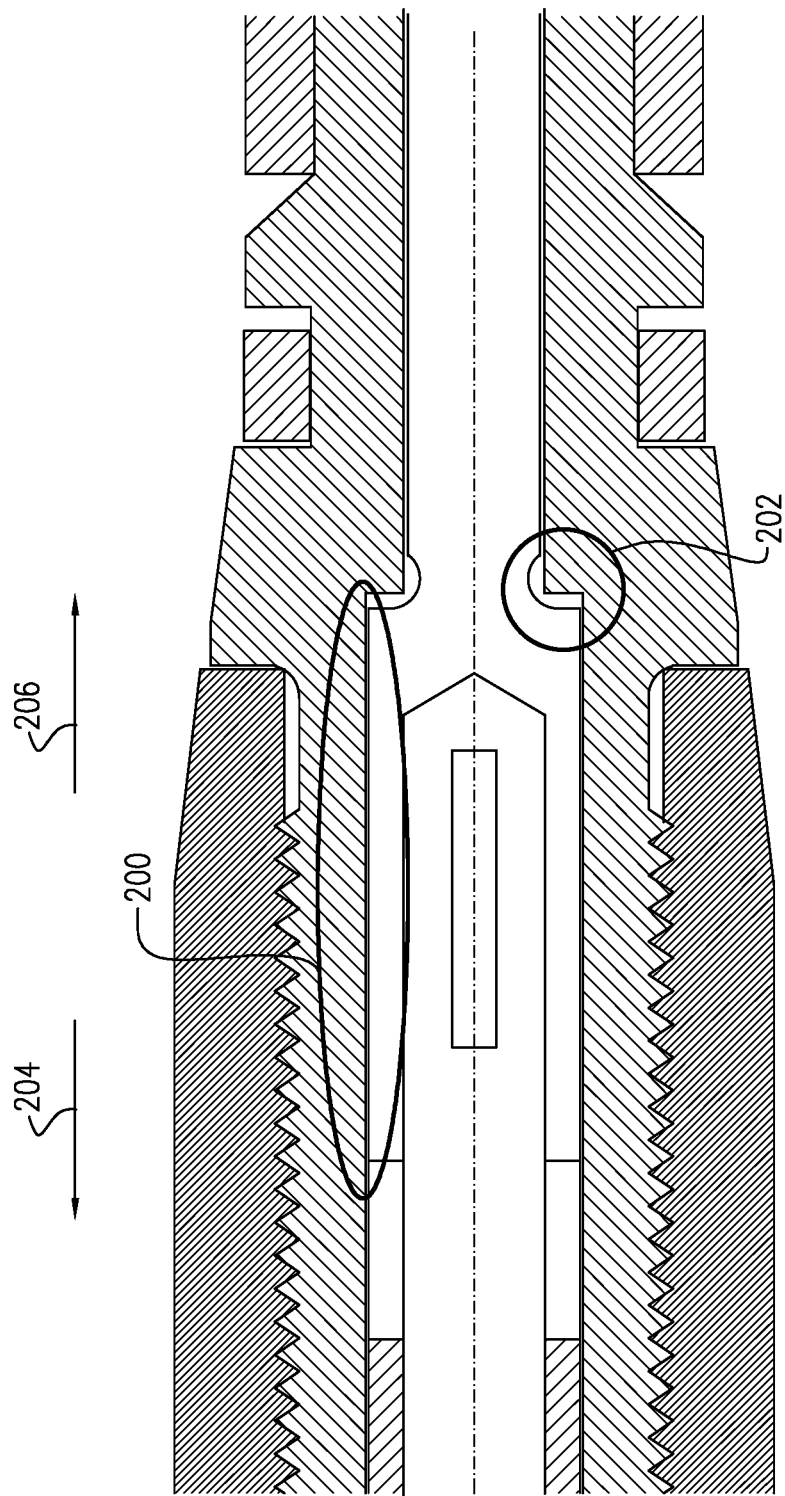
FIG. 8C is a schematic illustration of a typical bearing assembly that is used in prior art axial impeller-based blood pumps.

Reference is also made to FIG. 8C, which shows a typical bearing assembly that is used in prior art axial impeller-based blood pumps. FIG. 8C is shown for the purpose of acting as a point of reference for some of the applications of the invention described herein. As shown in FIG. 8C, a bearing assembly typically includes a radial bearing (indicated by ellipse 200) and a thrust bearing (indicated by circle 202). The radial bearing is configured to reduce radial motion of the impeller, by maintaining the axis of the impeller at a given radial position. In response to an impeller pumping blood in a first direction, forces acting upon the impeller typically push the impeller to move in the opposite direction to the first direction. The purpose of a thrust bearing is to oppose such motion of the impeller and to maintain the axial position of the impeller. In the example shown in FIG. 8C, in response to the impeller pumping blood in the direction of arrow 204, the impeller gets pushed in the direction of arrow 206, and the thrust bearing opposes this motion. Typically, due to the frictional forces that are exerted upon them, bearings undergo a substantial amount of heating and wear. Thrust bearings are typically exposed to substantial heating and wear, due to the fact that the frictional forces that are exerted upon them are typically spread over opposing surfaces having a smaller contact area between them, than is the case for radial bearings.

As described hereinabove, typically, axial shaft 92 passes through the axis of impeller 50, via lumen 62 of the impeller. Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. The axial shaft itself is radially stabilized via proximal radial bearing 116 and distal radial bearing 118.

Typically, a coupling portion 30 of frame 34 is coupled to proximal radial bearing 116, for example, via snap-fit coupling, and/or via welding. Typically, at the distal end of frame 34 distal strut junctions 33 are placed into grooves defined by the outer surface of distal radial bearing 118, the grooves being shaped to conform with the shapes of the distal strut portions. The proximal end of a distal-tip element 108 typically holds the distal strut portions in their closed configurations around the outside of distal radial bearing 118, as shown. For some applications, the device includes a distal extension 121 that extends distally from the distal radial bearing. Typically, the extension is configured to stiffen a region of the distal-tip element into which the distal end of shaft 92 moves.

As described above, axial shaft 92 is radially stabilized via proximal radial bearing 116 and distal radial bearing 118. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 or inner lining 39 (e.g., a gap that is as described above) is maintained, during rotation of the impeller, as described hereinabove. For some applications, axial shaft 92 is made of stainless steel, and proximal bearing 116 and/or distal bearing 118 are made of hardened steel. Typically, when crimping (i.e., radially constraining) the impeller and the frame for the purpose of inserting the impeller and the frame into the subject's body, distal bushing 58 of the impeller is configured to slide along the axial shaft in the distal direction, such that the impeller becomes axially elongated, while the proximal bushing remains in an axially fixed position with respect to the axial shaft. More generally, the impeller changes from its radially-constrained configuration to its non-radially-constrained configuration, and vice versa, by the distal bushing sliding over the axial shaft, while the proximal bushing remains in an axially fixed position with respect to the axial shaft.

Typically, the impeller itself is not directly disposed within any radial bearings or thrust bearings. Rather, bearings 116 and 118 act as radial bearings with respect to the axial shaft. Typically, the blood-pump catheter does not include any thrust bearing that is configured to be disposed within the subject's body and that is configured to oppose thrust generated by the rotation of the impeller. For some applications, one or more thrust bearings are disposed outside the subject's body (e.g., within a motor unit), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet that is disposed at the proximal end of the drive cable may be configured to maintain the impeller within a given range of axial positions.

For some alternative applications of the present invention, a thrust bearing is used to maintain the axial position of the impeller, and the thrust bearing is disposed within a portion of the blood-pump catheter that is proximal to the impeller, such that the thrust bearing does not come into contact with the subject's blood. For example, the thrust bearing may be disposed within an outer tube in which the drive shaft of the impeller is disposed. Alternatively or additionally, the thrust bearing may be disposed outside the subject's body. For some such applications, since the thrust bearing is disposed outside the subject's body, the thrust bearing's dimensions are not constrained by virtue of needing to be deployed within a small anatomical location. Therefore, in such cases, the contact area between the two opposing surfaces of the thrust bearing is typically greater than 20 square mm. For some applications (not shown), the thrust bearing is disposed distally to the impeller and in contact with the subject's blood, such that the thrust bearing is cooled by the subject's blood.

Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 10 is typically a hardware device programmed with computer program instructions to produce a special-purpose computer. For example, when programmed to perform the techniques described herein, computer processor 10 typically acts as a special-purpose, blood-pump computer processor.

The scope of the present invention includes combining any of the apparatus and methods described herein with any of the apparatus and methods described in one or more of the following applications, all of which are incorporated herein by reference:

U.S. Ser. No. 16/750,354 to Tuval, filed Jan. 23, 2020, entitled "Distal tip element for a ventricular assist device;"

U.S. 2019/0209758 to Tuval, which is a continuation of International Application No. PCT/IB2019/050186 to Tuval (published as WO 19/138350), entitled "Ventricular assist device, filed Jan. 10, 2019, which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018;

U.S. 2019/0269840 to Tuval, which is the U.S. national phase of International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

U.S. 2019/0175806 to Tuval, which is a continuation of International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

U.S. 2019/0239998 to Tuval, which is the U.S. national phase of International Patent Application PCT/IL2017/051092 to Tuval (published as WO 18/061002), filed Sep. 28, 2017, entitled "Blood vessel tube," which claims priority from U.S. Provisional Patent Application 62/401,403 to Tuval, filed Sep. 29, 2016;

U.S. 2018/0169313 to Schwammenthal, which is the U.S. national phase of International Patent Application PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump;"

U.S. 2017/0100527 to Schwammenthal, which is the U.S. national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

U.S. Pat. No. 10,039,874 to Schwammenthal, which is the U.S. national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the U.S. national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a venous system of a subject that includes one or more tributary vessels that flow into a vein at junctions between the vein and the one or more tributary vessels, the apparatus comprising:
    a blood-pump-catheter comprising:
        a material configured to be placed at a downstream location that is downstream of the junctions and to at least partially occlude blood flow through the vein at the downstream location, the material defining a blood-outlet opening;
        a blood pump that comprises an impeller that is disposed within a frame, the impeller being configured to pump blood from a region of the vein that is adjacent to the junctions, and through the blood-outlet opening defined by the material, by the impeller rotating within the frame;
        a blood-flow pathway that passes between (a) a pathway-inlet opening disposed at an upstream location that is upstream of the junctions and (b) a pathway-outlet opening that opens to a downstream side of the material,
        the blood-flow pathway being configured to direct upstream venous blood flow from the upstream location to downstream of the material, without the upstream venous blood flow being pumped by the pump.

2. The apparatus according to claim 1, wherein the blood pump comprises an elongate blood-pump tube, the elongate blood-pump tube defining a blood-inlet area which is disposed within an upstream portion of the elongate blood-pump tube, a blood-outlet area that is that is disposed within a downstream portion of the elongate blood-pump tube, and wherein the impeller is configured to pump blood into the blood-inlet area, through the elongate blood-pump tube, and out of the blood-outlet area.

3. The apparatus according to claim 1, wherein the blood-pump catheter is configured for use with one or more lymphatic vessels that flow into a vein, and wherein the blood-pump catheter is configured to be placed within the vein, such that:
    the material is placed at a downstream location that is downstream of junctions of the vein with the one or more lymphatic vessels and such as to at least partially occlude blood flow through the vein at the downstream location,
    the impeller is configured to pump blood from a region of the vein that is adjacent to the junctions of the vein with the one or more lymphatic vessels, and through the blood-outlet opening defined by the material, and
    the blood-flow pathway passes between (a) the pathway-inlet opening, the pathway-inlet opening being disposed at an upstream location that is upstream of the region of the vein that is adjacent to the junctions of the vein and the one or more lymphatic vessels and (b) the pathway-outlet opening, the pathway-outlet opening opening to the downstream side of the material,
    the blood-flow pathway being configured to direct upstream venous blood flow from the upstream location to the downstream side of the material, without the upstream venous blood flow being pumped by the impeller.

4. The apparatus according to claim 1, wherein the blood-pump catheter is configured to be placed within a vena cava of the subject, such that:
    the material is placed at a downstream location that is downstream of junctions of the vena cava with one or more renal veins of the subject and such as to at least partially occlude blood flow through the vena cava at the downstream location,
    the impeller is configured to pump blood from a region of the vena cava that is adjacent to the junctions of the vena cava with the one or more renal veins through the blood-outlet opening defined by the material, and
    the blood-flow pathway passes between (a) the pathway-inlet opening, the pathway-inlet opening being disposed at an upstream location that is upstream of junctions of the vena cava and the one or more renal veins and (b) the pathway-outlet opening, the pathway-outlet opening opening to the downstream side of the material, the blood-flow pathway being configured to direct blood flow from an infrarenal vena-caval bloodstream to downstream of the material, without the infrarenal vena-caval bloodstream being pumped by the impeller.

5. The apparatus according to claim 4, further comprising a percutaneous left-ventricular assist device configured to assist with left-ventricular functioning of the subject.

6. The apparatus according to claim 4, wherein the blood pump comprises an elongate blood-pump tube, the elongate blood-pump tube defining a blood-inlet area which is disposed within an upstream portion of the elongate blood-pump tube, a blood-outlet area that is that is disposed within a downstream portion of the elongate blood-pump tube, and wherein the impeller is configured to pump blood into the blood-inlet area, through the elongate blood-pump tube, and out of the blood-outlet area.

7. The apparatus according to claim 6, wherein the elongate blood-pump tube is configured to be disposed such that the blood-outlet area is disposed within a pulmonary artery of the subject and the impeller is configured to pump blood into the subject's pulmonary artery via the elongate tube.

8. The apparatus according to claim 6, further comprising an elongate tube that extends downstream from the material and that defines suprarenal blood-inlet openings that are configured to be disposed within a suprarenal vena cava of the subject, wherein the blood-inlet area of the elongate blood-pump tube is configured to be disposed downstream of the suprarenal blood-inlet openings and the impeller is configured to pump blood from a suprarenal vena-caval bloodstream into the subject's pulmonary artery.

9. The apparatus according to claim 4, further comprising an elongate tube that is configured to extend into a pulmonary artery of the subject, wherein the blood pump is configured to pump blood into the subject's pulmonary artery via the elongate tube.

10. The apparatus according to claim 9, wherein the elongate tube defines suprarenal blood-inlet openings that are configured to be disposed within a suprarenal vena cava of the subject, wherein the impeller is configured to be disposed downstream of the suprarenal blood-inlet openings and is configured to pump blood from a suprarenal vena-caval bloodstream into the subject's pulmonary artery.

11. The apparatus according to claim 4, wherein diameters of one or more portions of the blood-flow pathway are modulable, such that flow from the infrarenal vena-caval bloodstream to a right atrium of the subject is modulable.

12. The apparatus according to claim 11, further comprising a blood pressure sensor configured to detect blood pressure of the subject, and a computer processor configured to receive the subject's blood pressure and to automatically modulate the diameters of the one or more portions of the blood-flow pathway, in response to the detected blood pressure.

13. The apparatus according to claim 11, wherein the diameters of the one or more portions of the blood-flow pathway are configured to be modulated in response to an input.

14. The apparatus according to claim 1, wherein the blood-flow pathway comprises a funnel having a wide end and a narrow end, and one or more tubes, wherein the wide end of the funnel defines the pathway-inlet opening, and the narrow end of the funnel passes into the one or more tubes.

15. The apparatus according to claim 14, wherein the funnel and the one or more tubes comprise a single continuous blood-flow pathway.

16. The apparatus according to claim 1, wherein diameters of one or more portions of the blood-flow pathway are modulable, such that flow through the blood-flow pathway is modulable.

17. The apparatus according to claim 16, further comprising a blood pressure sensor configured to detect blood pressure of the subject, and a computer processor configured to receive the subject's blood pressure and to automatically modulate the diameters of the one or more portions of the blood-flow pathway, in response to the detected blood pressure.

18. The apparatus according to claim 16, wherein the diameters of the one or more portions of the blood-flow pathway are configured to be modulated in response to an input.

19. An apparatus comprising:
a blood-pump-catheter comprising:
a material disposed upon the blood-pump catheter and configured to at least partially occlude blood flow through a vein, the material defining a blood-outlet opening;
a blood pump that comprises an impeller that is disposed within a frame, the impeller being configured to pump blood through the blood-outlet opening defined by the material, by the impeller rotating within the frame;
a blood-flow pathway that passes between (a) a pathway-inlet opening disposed at a location that is proximal with respect to the material and (b) a pathway-outlet opening that opens to a location that is distal with respect to the material,
the blood-flow pathway being configured to direct blood flow from the pathway-inlet opening to the pathway-outlet opening, without the blood flow being pumped by the pump.

20. An apparatus for use with an arterial system of a subject that includes a main artery and one or more branching arteries that branch from the main artery at junctions between the main artery and the one or more branching arteries, the apparatus comprising:
a blood-pump-catheter comprising:
a material configured to be placed at a downstream location that is downstream of the junctions between the main artery with the branching arteries and to at least partially occlude blood flow through the main artery at the downstream location, the material defining a blood-inlet opening;
a blood pump that comprises an impeller that is disposed within a frame, the impeller being configured to pump blood from the main artery toward the branching arteries, through the blood-inlet opening, by the impeller rotating within the frame;
a funnel configured to be disposed at an upstream location that is upstream of junctions of the main artery with the branching arteries; and
a blood-flow pathway that passes between (a) a pathway-inlet opening disposed at an upstream location that is upstream of junctions of the main artery with the branching arteries and (b) a pathway-outlet opening that opens to a downstream side of the material,
the blood-flow pathway being configured to direct upstream main arterial blood flow from the upstream location to downstream of the material, without the upstream main arterial blood flow being pumped by the pump.

* * * * *